US010066203B2

(12) United States Patent
Fryer et al.

(10) Patent No.: US 10,066,203 B2
(45) Date of Patent: Sep. 4, 2018

(54) METHODS, SURFACE MODIFIED PLATES AND COMPOSITIONS FOR CELL ATTACHMENT, CULTIVATION AND DETACHMENT

(75) Inventors: Benjamin Fryer, Skillman, NJ (US); Shelley Nelson, Skillman, NJ (US); Villy Nielsen, Roskilde (DK); Tina Kristensen Marwood, Hvalsø (DK); Thomas Brevig, Jyllinge (DK)

(73) Assignees: Janssen Biotech Inc., Horsham, PA (US); Nunc A/S, Horsham, PA (US)

( * ) Notice: Subject to any disclaimer, the term of this patent is extended or adjusted under 35 U.S.C. 154(b) by 935 days.

(21) Appl. No.: 12/388,930

(22) Filed: Feb. 19, 2009

(65) Prior Publication Data
US 2009/0215177 A1 Aug. 27, 2009

Related U.S. Application Data

(60) Provisional application No. 61/030,544, filed on Feb. 21, 2008.

(51) Int. Cl.
*C12N 5/00* (2006.01)
*C12N 5/0735* (2010.01)

(52) U.S. Cl.
CPC ........ *C12N 5/0606* (2013.01); *C12N 2501/70* (2013.01); *C12N 2509/00* (2013.01); *C12N 2533/00* (2013.01)

(58) Field of Classification Search
CPC .................................................. C12N 5/0606
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 * | 9/2003 | Bryhan et al. ............. 435/283.1 |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS (Ginis et al, Developmental Biology, 269: 360-380, 2004).*
(Guilak et al (Stem Cell, 5:17-26, 2009).*
van Kooten et al (Biomaterials 25: 1735-1747, 2004).*
Kang et al (AATCC Review, pp. 29-33, 2004).*
Abe, et al., Evidence That PI3K, Rac, Rho, and Rho Kinase Are Involved in Basic Fibroblast Growth Factor—Stimulated Fibroblast—Collagen Matrix Contraction, Journal of Cellular Biochemistry, 2007, pp. 1290-1299, vol. 102.
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.

(Continued)

*Primary Examiner* — Anoop K Singh
*Assistant Examiner* — Magdalene K Sgagias
(74) *Attorney, Agent, or Firm* — Lois A. Gianneschi

(57) ABSTRACT

The present invention relates to the field of mammalian cell culture, and provides methods and compositions for cell attachment to, cultivation on and detachment from a solid substrate surface containing from at least about 0.5% N, a sum of O and N of greater than or equal to 17.2% and a contact angle of at least about 13.9 degrees, lacking a feeder cell layer and lacking an adlayer. In one embodiment of the present invention, the cells are treated with a compound capable of inhibiting Rho kinase activity. In another embodiment, the cells are treated with a compound capable of inhibiting Rho activity.

22 Claims, 46 Drawing Sheets

(56) References Cited

U.S. PATENT DOCUMENTS

| | | |
|---|---|---|
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,873 B2 | 3/2009 | Mistry |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 2002/0072117 A1 | 7/2002 | Xu |
| 2002/0151053 A1* | 10/2002 | Carpenter et al. ............ 435/366 |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0118148 A1 | 6/2005 | Stein et al. |
| 2005/0148070 A1 | 7/2005 | Thomson et al. |
| 2005/0158852 A1 | 7/2005 | Wang et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003313 A1 | 1/2006 | D'Amour et al. |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0141702 A1 | 6/2007 | Revazova et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0159994 A1 | 7/2008 | Mantalaris et al. |
| 2008/0241107 A1 | 10/2008 | Copland, III et al. |
| 2008/0260700 A1 | 10/2008 | Accil et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0053182 A1 | 2/2009 | Ichim et al. |
| 2009/0087907 A1* | 4/2009 | Pebay .................. C07K 14/78 435/395 |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0189777 A1 | 7/2013 | Rezania |
| 2013/0224156 A1 | 8/2013 | Takahashi et al. |
| 2014/0186953 A1 | 7/2014 | Rezania |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 92302 B1 | 1/1988 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 2359030 C1 | 6/2009 |
| RU | 2359671 C2 | 6/2009 |

(56) References Cited

FOREIGN PATENT DOCUMENTS

| | | |
|---|---|---|
| WO | WO199219759 A2 | 2/1992 |
| WO | 1996040172 A1 | 12/1996 |
| WO | 199847892 A1 | 10/1998 |
| WO | WO199920741 A1 | 4/1999 |
| WO | 200029549 A1 | 5/2000 |
| WO | 200123528 A1 | 4/2001 |
| WO | WO200151616 A2 | 7/2001 |
| WO | WO200181549 A3 | 11/2001 |
| WO | 200246183 A2 | 6/2002 |
| WO | 200246197 A1 | 6/2002 |
| WO | 2002086107 A2 | 10/2002 |
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | WO2003050249 A1 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | WO2003102134 A2 | 12/2003 |
| WO | 2004016747 A2 | 2/2004 |
| WO | WO2004011621 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 A1 | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO 2005/014799 A1 | 2/2005 |
| WO | 2005058301 A1 | 6/2005 |
| WO | 2005063971 A1 | 7/2005 |
| WO | WO 2005/065354 A2 | 7/2005 |
| WO | WO 2005/065354 A3 | 7/2005 |
| WO | 2005080551 A2 | 9/2005 |
| WO | WO 2005/086845 A2 | 9/2005 |
| WO | WO 2005/086845 A3 | 9/2005 |
| WO | 2005097977 A2 | 10/2005 |
| WO | 2005097980 A2 | 10/2005 |
| WO | WO2005116073 A3 | 12/2005 |
| WO | 2006020919 A2 | 2/2006 |
| WO | 2006088867 A2 | 2/2006 |
| WO | WO2006016999 A1 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006126574 A1 | 11/2006 |
| WO | WO 2006/114098 A2 | 11/2006 |
| WO | WO 2006/114098 A3 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | WO 2007/030870 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A1 | 9/2007 |
| WO | 2007127927 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008015682 A2 | 2/2008 |
| WO | 2008036447 A2 | 3/2008 |
| WO | WO 2008/035110 A1 | 3/2008 |
| WO | 2008048671 A1 | 4/2008 |
| WO | WO2008048647 A1 | 4/2008 |
| WO | 2009096049 A1 | 5/2008 |
| WO | 2008086005 A1 | 7/2008 |
| WO | 2008094597 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | WO2009105570 A1 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011096223 A1 | 8/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055397 A1 | 4/2013 |
| WO | 2013055834 A2 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.

Ackermann, et al., Molecular Regulation of Pancreatic B-Cell Mass Development, Maintenance, and Expansion, Journal of Molecular Endocrinology, 2007, pp. 193-206, vol. 38.

Adams, et al., Proteasome Inhibition in Cancer: Development of PS-341, Seminars in Oncology, 2001, pp. 613-619, vol. 28, No. 6.

Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

Ali, et al., Exploitation of Protein Kinase C: A Useful Target for Cancer Therapy, Cancer Treatment Reviews, 2009, pp. 1-8, vol. 35.

Allegrucci, et al., Differences between Human Embryonic Stem Cell Lines, Human Reproduction Update, Aug. 26, 2006, pp. 1-18, Advance Access.

Almond, et al., The Proteasome: A Novel Target for Cancer Chemotherapy, Leukemia, 2002, pp. 433-443, vol. 16.

Amit, et al., Clonally Derived Human Embryonic Stem Cell Lines Maintain Pluripotency and Proliferative Potential for Prolonged Periods of Culture, Developmental Biology, 2000, pp. 271-278, vol. 227.

(56) References Cited

OTHER PUBLICATIONS

Amit, et al., Dynamic Suspension Culture for Scalable Expansion of Undifferentiated Human Pluripotent Stem Cells, Nature Protocols, Apr. 7, 2011, pp. 572-579, vol. 6, No. 5.

Amit, et al., Feeder Layer-and Serum-Free Culture of Human Embryonic Stem Cells, Biology of Reproduction, 2004, pp. 837-845, vol. 70.

Assady, et al., Insulin Production by Human Embryonic Stem Cells, Diabetes, 2001, pp. 1691-1697, vol. 50.

Baertschiger, et al., Mesenchymal Stem Cells Derived From Human Exocrine Pancrea Express Transcription Factors Implicated in Beta-Cell Development, Pancreas, 2008, pp. 75-84, vol. 37, No. 1.

Baetge, Production of B-Cells from Human Embryonic Stem Cells, Diabetes, Obesity, Metabolism, 2008, pp. 186-194, vol. 10, Supplement 4.

Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.

Balsam, et al., Haematopoeitic Stem Cells Adopt Mature Haeatopoietic Fates in Ischaemic Myocardium, Nature, Apr. 8, 2004, pp. 668-673, Nature Publishing Group.

Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.

Barclay, et al., The Leucocyte Antigen Facts Book, The Leucocyte Antigen Facts Book, 1997, Textbook, 2[sup] edition, Academic Press.

Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.

Beltrami, et al., Adult Cardiac Stem Cells are Multipotent and Support Myocardial Regeneration, Cell, Sep. 19, 2003, pp. 763-776, vol. 114, Cell Press.

Best, et al., Embryonic Stem Cells to Beta-Cells by Understanding Pancreas Development, Molecular and Cellular Endorinology, 2008, pp. 86-94, vol. 288.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.

Bo, et al., Research Progress of Pancreatic Islet Development and Pancreatic Stem Cells, Journal of Clinical Surgery, 2009, pp. 208-210, vol. 17, No. 3.

Bocian-Sobkowska, et al., Polyhormonal Aspect of the Endocrine Cells of the Human Fetal Pancreas, Histochem Cell Biol, 1999, pp. 147-153, vol. 112, Issue 2.

Borowiak, et al., How to Make AB Cells, Current Opinion Cell Biology, 2009, pp. 727-732, vol. 21, Issue 6.

Borowitz, et al., Prognostic Significance of Fluorescence Intensity of Surface Marker . . . , Blood, Jun. 1, 1997, 3960-3966, 89-11, American Society of Hematology, Washington, D.C., US.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, pp. 86-93, vol. 269-1, US.

Brambrink, et al., Sequential Expression of Pluripotency Markers During Direct Reprogramming of Mouse Somatic Cells, Cell Stem Cell, 2008, pp. 151-159, vol. 2.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Embryonic Stem Cells Towards Pancreatic Progenitor Cells and their Transplantation Into Strepozotocin-Induced Diabetic Mice, Cell Biology International, 2008, pp. 456-461, vol. 32.

Chen, et al., Differentiation of Rat Marrow Mesencymal Stem Cells in Pancreatic Islet Beta-Cells, World Journal of Gastroenterology, Oct. 15, 2004, 3016-3020, 10.

Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.

Chetty, et al., A Simple Tool ti Improve Pluripotent Stem Cell Differentiation, Nature Methods, 2013, pp. 553-558, vol. 10, No. 6.

Choi, et al., In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330.

Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al, Production of pancreatic hormone-expressing endocrine cells from human embryonic stem cells, Nature Biotechnology, 2006, pp. 1392-1401, vol. 24.

Damy, et al., Increased Neuronal Nitric Oxide Synthase-Derived NO Production in the Failing Human Heart, Research Letters, Apr. 24, 2004, pp. 1365-1367, vol. 363.

David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.

De Coppi, et al., Isolation of Amniotic Stem Cell Lines with Potential for Therapy, Nature Biotechnology, 2007, pp. 100-106, vol. 25, No. 1.

(56) References Cited

OTHER PUBLICATIONS

De Rosa, 11-color, 13-parameter flow cytometry: Identification of . . . , Nature, Feb. 1, 2001, pp. 245-248, vol. 7-2, Nature Publishing Group, US.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Deramaudt, et al., The PDX1 Homeodomain Transcription Factor Negatively Regulates the Pancreatic Ductal Cell-specific Keratin 19 Promoter, Journal of Biological Chemistry, 2006, pp. 38385-38395, vol. 281, No. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dufour, et al., Development of an Ectopic Site for Islet Transplantation Using Biodegradable Scaffolds, Tissue Engineering, 2005, pp. 1323-1331, vol. 11, No. 9/10.
Eguizabal, et al., Embryonic Stem Cells/Induced Pluriptent Stem Complete Meiosis from Human Induced Pluripotent Stem Cells, Stem Cells, 2011, pp. 1186-1195, vol. 29.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthalmology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Florio, et al., Activin A Stimulates Insulin Secretion in Cultured Human Pancreatic Islets, J. Endocrinol. Invest., 2000, pp. 231-234, vol. 23.
Fok, et al., Shear-Controlled Single-Step Mouse Embryonic Stem Cell Expansion and Embryoid Body-Based Differentiation, Stem Cells, 2005, pp. 1333-1342, vol. 23.
Foster, et al., Differentiation of Transplanted Microencapsulated Fetal Pancreatic Cells, Experimental Transplantation, Jun. 15, 2007, pp. 1440-1448, vol. 83, No. 11.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gibco, Solutions for Life Science Research and Drug Discovery, Catalogue Cell Culture Products, 2004-2005, pp. 1-4E, 281406 26 5 27.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gittest, Developmental Biology of the Pancreas: A comprehensive Review, Developmental Biology, 2009, pp. 4-35, vol. 326, No. 1.
Gordon Weir, Do stem cells hold the key to creation of a cure for diabetes?, Diabetes Voice, 2008, pp. 29-31, Edition 53, No. 2.
Gosden, et al., Amniotic Fluid Cell Types and Culture, British Medical Bulletin, 1983, pp. 348-354, vol. 39, No. 4.
Gregg Duester, Retionoic Acid Synthesis and Signaling During Early Organogenesis, Cell, 2008, pp. 921-931, vol. 134.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hainsworth, et al., Retinal Capillar Basement Membrane Thickening in a Porcine Model of Diabetes Mellitus, Comp Med, 2002, pp. 523-529, vol. 52.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harmon, et al., GDF11 Modulates NGN3+ Islet Progenitor Cell Number and Promotes B-Cell Differentiation in Pancreas Development, Development, 2004, pp. 6163-6174, vol. 131.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Hay, et al., Highly Efficient Differentiation of hESCs to Functional Hepatic Endoderm Requires ActivinA and Wnt3a Signaling, PNAS, 2008, pp. 12301-12306, vol. 105, No. 34.
Heinis, et al., HIF1a and Pancreatic Beta-Cell Development, The FASEB Journal, 2012, pp. 2734-2742, vol. 26.
Heinis, et al., Oxygen Tension Regulates Pancreatic Beta-Cell Differentiation Through Hypoxia-Inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.

(56) References Cited

OTHER PUBLICATIONS

Henderson, et al., Preimplantation Human Embryos and Embryonic Stem Cells Show Comparable Expression of Stage-Specific Embryonic Antigens, Stem Cells, 2002, pp. 329-337, vol. 20.
Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.
Herrera, Adult-Insulin-and Glucagon-Producing Cells Differentiate from Two Independent Cell Lineages, Development, 2000, pp. 2317-2322, vol. 127, No. 11.
Herzenberg, et al., Fluorescence-activated Cell Sorting, Scientific American, 1976, pp. 108-117, vol. 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Ho, et al., Animal Cell Bioreactors, Animal Cell Bioreactors, 1991, 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hoffman, et al., Characterization and Culture of Human Embryonic Stem Cells, Nature Biotechnology, 2005, pp. 699-708, vol. 23, No. 6.
Hosoya, et al., Induction of Differentiation of Undifferentiated Cells into Pancreatic Beta-Cells in Vertebrates, Int. J. Dev. Biol., 2012, pp. 313-323, vol. 56.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Int' Anker, et al., Amniotic Fluid as a Novel Source of Mesenchymal Stem Cells for Therapeutic Transplantation, Blood, Aug. 15, 2003, pp. 1548-1549, vol. 102, No. 4.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Jiang, et al., In Vitro Derivation of Functional Insulin-Producing Cells from Human Embryonic Stem Cells, Cell Research, 2007, pp. 333-344, vol. 17.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Karvonen, et al., Incidene of Childhood Type 1 Diabetes Worldwide, Diabetes Care, 2000, pp. 1516-1526, vol. 23, No. 10.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kicic, et al., Differentiation of Marrow Stromal Cells into Photoreceptors in the Rat Eye, The Journal of Neuroscience, Aug. 27, 2003, pp. 7742-7749, vol. 23, Issue 21.

Kingsley, The TGF-B Superfamily: New Members, New Receptors, and New Genetic Tests of Function in Different Organisms, Genes & Development, 1994, pp. 133-146, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Konstantinova, et al., EphA-Ephrin-A-Mediated Beta Cell Communication Regulates Insulin Secretion from Pancreatic Islets, Cell, Apr. 20, 2007, pp. 359-370, vol. 129.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9,10-diones, Journal of Medical Chemistry, 1985, pp. 1124-1126, vol. 28, American Chemical Society.
Kron, et al., Expression of Human Activin C Protein in Insect Larvae Infected with a Recombinant Baculovirus, Journal of Virological Methods, 1998, pp. 9-14, vol. 72.
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.
Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.
Lanza et al., Characteristics and Characterization of Human Pluripotent Stem Cells, Stem Cell Anthology, 2010, pp. 141, 142, 144 and 146, 1st Edition.
Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.
Larsen, et al., Use of the Gootingen Minipig as a Model of Diabetes, with Special Focus on Type 1 Diabetes Research, ILAR Journal, 2004, pp. 303-313, vol. 45, No. 3.
Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.
Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.
Lee, et al., PKC-Inhibitors Sustain Self-Renewal of Mouse Embryonic Stem Cells Under Hypoxia in Vitro, Experimental and Molecular Medicine, Apr. 2010, pp. 294-301, vol. 43, No. 4.
Lee, et al., Protein Kinase A- and C-Induced Insulin Release from Ca2+-Insensitive Pools, Cellular Signalling, 2003, pp. 529-537, vol. 15.
Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

(56) References Cited

OTHER PUBLICATIONS

Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.

Leon-Quinto, et al., In Vitro Directed Differentiation of Mouse Embryonic Stem Cells into Insulin-Producing Cells, Diabetologia, 2004, pp. 1442-1451, vol. 47, No. 8.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Li, et al., Pluripotency Can be Rapidly and Efficiently Induced in Human Amniotic Fluid-Derived Cells, Human Molecular Genetics, 2009, pp. 4340-4349, vol. 18, No. 22.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Defined Culture Media for Human Embryonic Stem Cells, Embryonic Stem Cells, 2007, pp. 1-16, Springer.

Ludwig, et al., Derivation of Human Embryonic Stem Cells in Defined Conditions, Nature Biotechnology, Feb. 2006, pp. 185-187, vol. 24 No. 2.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

Miller, et al., The Pig as a Model for Human Nutrition, Annual Review of Nutrition, 1987, pp. 361-382, vol. 7, Annual Reviews Inc.

Milunsky, et al., Genetic Disorders and the Fetus: Diagnosis Prevention and Treatment, Pediatric and Developmental Pathology, 2011, pp. 84, vol. 14, Society for Pediatric Pathology.

Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.

Mitsui, et al., The Homeoprotein Nanog is Required for Maintenance of Pluripotency in Mouse Epiblast and ES Cells, Cell, May 30, 2003, pp. 631-642, vol. 113, Cell Press.

Moore, et al., The Corneal Epithelial Stem Cell, DNA and Cell Biology, 2002, pp. 443-451, vol. 21, No. 5/6.

Moran, et al., Bidirectional-Barbed Sutured Knotless Running Anastomosis v Classic van Velthoven in a Model System, Journal of Endourology, 2007, pp. 1175-1177, vol. 21, No. 10.

Morrison, et al., Culture in Reduced Levels of Oxygen Promotes Clonogenic Sympathoadrenal Differentiation by Isolated Neural Crest Stem Cells, Journal of Neuroscience, Oct, 1, 2000, pp. 7370-7376, vol. 20, No. 19.

Movassat, et al., Keratinocyte Growth Factor and Beta-Cell Differentiation in Human Fetal Pancreatic Endocrine Precursor Cells, Diabetologia, 2003, pp. 822-829, vol. 46.

Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.

Munoz, et al., Conventional Pluripotency Markers are Unspecific for Bovine Embryonic-Derived Cell-Lines, Theriogenology, 2008, pp. 1159-1164, vol. 69.

Murtha, et al., Evaluation of a Novel Technique for Wound Closure Using a Barbed Suture, Cosmetic, Aug. 2, 2005, pp. 1769-1780, vol. 117, No. 6.

Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.

Nakamura, et al., Ocular Surface Reconstruction Using Cultivated Mucosal Epithelial Stem Cells, Cornea, Oct. 2003, S75-S80, vol. 22, Supplement 1.

Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.

Nie, et al., Scalable Passaging of Adherent Human Pluripotent Stem Cells, PLOS One, 2014, pp. 1-9, vol. 9, Issue 1.

Nishimura, et al., Expression of MafA in Pancreatic Progenitors is Detrimental for Pancreatic Development, Developmental Biology, 2009, pp. 108-120, vol. 333.

Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.

Odom, et al., Control of Pancreas and Liver Gene Expression by HNF Transcription Factors, Science, 2004, pp. 1378-1381, vol. 303, No. 5662.

Oh, et al., Human Embryonic Stem Cells: Technological Challenges Towards Therapy, Clinical and Experimental Pharmacology and Physiology, 2006, pp. 489-495, vol. 33.

Okita, et al., Generation of Germline-Competent Induced Pluripotent Stem Cells, Nature, Jul. 19, 2007, pp. 313-317, vol. 448.

Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.

(56) References Cited

OTHER PUBLICATIONS

Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.

Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.

Ouziel-Yahalom, et al., Expansion and Redifferentiation of Adult Human Pancreatic islet Cells, Biochemical and Biophysical Research Communications, 2006, pp. 291-298, vol. 341.

Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.

Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.

Pangas, et al., Production and Purification of Recombinant Human Inhibin and Activin, Journal of Endocrinology, 2002, pp. 199-210, vol. 172.

Paris, et al., Equine Embryos and Embryonic Stem Cells: Defining Reliable Markers of Pluripotency, Theriogeneology, 2010, pp. 516-524, vol. 74.

Park, et al., Effects of Activin A on Pancreatic Ductal Cells in Streptozotocin-Inducted Diabetic Rats, Experimental Transplantation, 2007, pp. 925-930, vol. 83.

Perrier, et al., Derivation of Midbrain Dopamine Neurons from Human Embryonic Stem Cells, PNAS, Aug. 24, 2004, pp. 12543-12548, vol. 101, No. 34.

Phillips, et al., Attachment and Growth of Human Embryonic Stem Cells on Microcarriers, Journal of Biotechnology, 2008, pp. 24-32, vol. 138.

Phillips, et al., Directed Differentiation of Human Embryonic Stem Cells into the Pancreatic Endocrine Lineage, Stem Cells and Development, 2007, pp. 561-578 XP009090586, vol. 16, No. 4.

Pouton, et al., Embryonic Stem Cells as a Source of Models for Drug Discovery, Nature Reviews Drug Discovery, Aug. 2007, pp. 1474-1776, vol. 6, No. 8.

Prowse, et al., A Proteome Analysis of Conditioned Media from Human Neonatal Fibroblasts Used in the Maintenance of Human Embryonic Stem Cells, Proteomics, 2005, pp. 978-989, vol. 5.

Prusa, et al., Oct-4-Expressing Cells in Human Amniotic Fluid: a New Source for Stem Cell Research?, Human Reproduction, 2003, pp. 1489-1493, vol. 18, No. 7.

Ptasznik, et al., Phosphatidylinositol 3-Kinase Is a Negative Regulator of Cellular Differentiation, The Journal of Cell Biology, 1997, pp. 1127-1136, vol. 137, No. 5.

R&D Systems, Embryonic & Induced Pluripotent Stem Cell Transcription Factors, Embryonic & Induced Pluripotent Stem Cell Transcription Factors, 2013, http://www.rndsystems.com/molecule_group.aspx?r=1&g=3041, 2 page web printout.

R&D Systems, Pancreatic Endoderm, Pancreatic Endoderm, Jun, 24, 2013, http://www.rndsystems.com/molecule_group.aspx?g=801&r, 1 page web printout.

Rajagopal, et al., Insulin Staining of ES Cell Progeny from Insulin Uptake, Science, Jan. 17, 2003, pp. 363, vol. 299.

Rajala, et al., Testing of Nine Different Xeno-free Culture Media for Human Embryonic Stem Cell Cultures, Human Reproduction, Jan. 24, 2007, pp. 1231-1238, vol. 22, No. 5.

Ramiya, et al., Reversal of Insulin-Dependent Diabetes Using Islets Generated in vitro from Pancreatic Stem Cells, Nature Medicine, 2000, pp. 278-281, vol. 6.

Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.

Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.

Reisner, Growing Organs for Transplantation form Embryonic Precursor Tissues, Immunol. Res., 2007, pp. 261-273, vol. 38.

Rezania, E al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.

Rezania, et al., Enrichment of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.

Rezania, Production of Functional Glucagon-Secreting-Cells from Human Embryonic Stem Cells, Diabetes, 2011, pp. 239-247, vol. 60, Issue 1.

Richards, et al., Development of Defined Media for the Serum-Free Expansion of Primary Keratinocytes and Human Embryonic Stem Cells, Tissue Engineering, 2008, pp. 221-232, vol. 14, No. 3.

Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.

Ross, et al., Cytochrome P450s in the Regulation of Cellular Retinoic Acid Metabolism, Annu. Rev. Nutr., 2011, pp. 65-87, vol. 31.

Rowley, et al., Meeting Lot-Size Challenges of Manufacturing Adherent Cells for Therapy, Cell Therapies Manufacturing, 2012, pp. 16-22, vol. 10, No. 3.

Ryan, et al., Clinical Outcomes and Insulin Secretion After Islet Transplantation with the Edmonton Protocol, Diabetes, Apr. 2001, pp. 710-719, vol. 50.

Sakaguchi, et al., Integration of Adult mesenchymal Stem Cells in the CNS, Society for Neuroscience Abstract Viewer and Itinerary Planner, 2002, Program 237.18.

Sander, et al., Homeobox Gene Nkk6.1 Lies Downstream of Nkx2.2 in the Major Pathway of Betta-Cell Formation in the Pancreats, Development, 2000, pp. 5533-5540, vol. 127.

Sato, et al., Maintenance of Pluripotency in Human and Mouse Embryonic Stem Cells Through Activation of WNT Signaling by a Pharmacological GSK-3-specific Inhibitor, Nature Medicine, Jan. 2004, pp. 55-63, vol. 10, No. 1.

Sato, et al., Manipulation of Self-Renewal in Human Embryonic Stem Cells Through a Novel Pharmacological GSK-3 Inhibitor, Methods in Molecular Biology, 2006, pp. 115-128, vol. 331.

Sato, et al., Molecular Signature of Human Embryonic Stem Cells and its Comparison with the Mouse, Developmental Biology, Apr. 23, 2003, pp. 404-413, vol. 260.

Savino et al., Generation of Interleukin-6 Receptor Antagonists by Molecular-Modeling Guided Mutagenesis of Residues Important for gp130 Activation, EMBO Journal, 1994, 1357-1367, 13-6, IT.

Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, vol. 102, No. 20.

Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.

Schraermeyer, et al., Subretinally Transplanted Embryonic Stem Cells Rescue Photoreceptor Cells From Degeneration in the RCS Rats, Cell Transplantation, 2001, pp. 673-680, vol. 10.

Schroeder, et al., Differentiation of Mouse Embryonic Stem Cells to Insulin-Producing Cells, Nature Protocols, 2005, pp. 495-507, vol. 1, No. 2.

Schuldiner, et al., Induced Neuronal Differentiation of Human Embryonic Stem Cells, Brain Research, 2001, pp. 201-205, vol. 913.

Schulz, et al., A Scalable System for Production of Functional Pancreatic Progenitors from Human Embryonic Stem Cells, PLOS One, 2012, pp. 1-17, vol. 7, Issue 5.

(56) References Cited

OTHER PUBLICATIONS

Scullica, et al., Diagnosis and Classification of Macular Degenerations: an Approach Based on Retinal Function Testing, Documenta Ophthalmologica, 2001, pp. 237-250, vol. 102.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, XP002567665, vol. 439.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Sherwood, et al., Transcriptional Dynamics of Endodermal Organ Formation, Developmental Dynamics, 2009, pp. 29-42, vol. 238, Issue 1.
Shim, et al., Directed Differentiation of Human Embryonic Stem Cells Towards a Pancreatic Cell Fate, Diabetologia, 2007, pp. 1228-1238, vol. 50.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.
Sneddon, et al., Self-Renewal of Embryonic-Stem-Cell-Derived Progenitors by Organ-Matched Mesenchyme, Nature, Nov. 29, 2012, pp. 765-770, vol. 491.
Soria, et al., From Stem Cells to Beta Cells: New Strategies in Cell Therapy of Diabetes Mellitus, Diabetologia, 2001, pp. 407-415, vol. 44.
Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stacpoole, et al., Efficient Derivation of Neural Precuros Cells, Spinal Motor Neurons and Midbr, Nat Protoc, 2012, pp. 1-26, vol. 6, Issue 8.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stafford, et al., Retinoids Signal Directly to Zebrafish Endoderm to Specify Insuilin-Expressing B-cells, Development, 2005, pp. 949-956, vol. 133.
Stoffel, et al., Navigating the Pathway from Embryonic Stem Cells to Beta Cells, Seminars in Cell & Developmental Biology, 2004, pp. 327-336, vol. 15.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Takahashi, et al., Homogenous Seeding of Mesenchymal Stem Cells into Nonwoven Fabric for Tissue Engineering, Tissue Engineering, 2003, pp. 931-938, vol. 9, No. 5.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 8770886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tsuchida, et al., Activin Isoforms Signal Through Type I Receptor Serine/Threonin Kinase ALK7, Molecular and Cellular Endocrinology, 2004, pp. 59-65, vol. 22.
Uludag, et al., Technology of Mammalian Cell Encapsulation, Advanced Drug Delivery Reviews, 2000, pp. 29-64, vol. 42.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Valet, et al., Pretherapeutic Identification of High-Risk Acute Myeloid Leukemia (AML) Patients from . . . , Clinical Cytometry, Feb. 17, 2003, pp. 4-10, vol. 53B, Wiley-Liss, Inc., US.
Van Der Greef et al., Rescuing drug discovery: in vivo systems pathology and systems pharmacology, Nature, Dec. 1, 2005, pp. 961-967, vol. 4-1, Nature Reviews, US.
Van Der Windt, et al., The Chioce of Anatomical Site for Islet Transplantation, Cell Transplantation, 2008, pp. 1005-1014, vol. 17.
Van Wachem, et al., Method for the Fast Application of an Evenly Distributed Cell Layer on Porous Vascular Grafts, Biomaterials, 1990, pp. 602-606, vol. 11.
Verfaillie, et al., Stem Cells: Hype and Reality, Hematology, 2002, pp. 369-391.
Vieira, et al., Modulation of Neuronal Stem Cell Differentiation by Hypoxia and Reactive Oxygen Species, Progress in Neurobiology, 2011, pp. 444-455, vol. 93.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Relationship of Chemical Structurs of Anthraquinones with their Effects onthe Suppression of Immune Responses, International Journal of Immunopharmacology, 1987, pp. 733-739, vol. 9-6, International Society for Immunopharmacology, GB.

(56) References Cited

OTHER PUBLICATIONS

Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu, et al., Basic FGF and Suppression of BMP Signalling Sustain Undifferentiated Proliferation of Human ES Cells, Nature Methods, 2005, pp. 185-189, vol. 2, Issue 3.
Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.
Yang, et al., Evaluation of Humam MSCs Cell Cycle, Viability and Differentiation in Micromass Culture, Biorheology, 2006, p. 489-496, vol. 43.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zalzman, et al., Differentiation of Human Liver-Derived, Insulin-Producing Cells Toward the B-Cell Phenotype, Diabetes, 2005, pp. 2568-2575, vol. 54.
Zembower, et al., Peptide Boronic Acids Versatile Synthetic Ligands for Affinity Chromatography of Serine Proteinases, International Journal Peptide Protein, 1996, pp. 405-413, vol. 47.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127.
Zhang_et_al, Highly Efficient Differentiation of Human ES Cells and iPS Cells into Mature Pancreatic Insulin-Producing Cells, Cell Research, 2009, pp. 429-438, vol. 19, Issue 14.
Zhao, et al., Derivation and Characterization of Hepatic Progenitor Cells from Human Embryonic Stem Cells, PLoS One Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Zuscik, et al., Regulation of Chondrogenesis and Chondrocyte Differentiation by Stress, J Clin Invest, 2008, pp. 429-438, vol. 118, Issue 2.
Cohick, et al., The Insulin-Like Growth Factors, Annual Reviews Physiol, 1993, pp. 131-153, vol. 55, Annual Reviews Inc.
Hebrok, et al., Notochord repression of endodermal Sonic hedgehog permits pancreas development, Genes & Development, Jun. 1, 1998, pp. 1705-1713, vol. 12, Issue 11, Cold Spring Harbor Laboratory Press.
Jaenisch, et al., Stem Cells, the Molecular Circuitry of Pluripotency and Nuclear Reprogramming, Cell, Feb. 22, 2008, pp. 567-582, vol. 132, Elsevier Inc.
Klajnert, et al., Fluorescence studies on PAMAM dendrimers interactions with bovine serum albumin, Bioelectrochemistry, 2002, pp. 33-35, vol. 55.
Kubota,et al., Growth factors essential for self-renewal and expansion of mouse spermatogonial stem cells, cell Biology, Nov. 23, 2004, pp. 16489-16494, vol. 101, Issue 47.
Nostro, et al., Generation of Beta Cells from Human Pluripotent Stem Cells: Potential for Regenerative Medicine, Seminars in Cell & Developmental Biology, 2012, pp. 701-710, vol. 23.
Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytocheinistry, 1986, pp. 527-533, vol. 34, Issue 4.
Rezania, et al., Reversal of Diabetes with Insulin-Producing Cells Derived in vitro from Human Pluripotent Stem Cells, Nature Biotechnology, 2014, pp. 1121-1133, vol. 32, No. 11.
Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182, Issue 2.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.
Wachs, et al., High Efficacy of Clonal Growth and Expansion of Adult Neural Stem Cells, Laboratory Investigation, 2003, pp. 949-962, vol. 83, No. 7.
Brimble, S., et al., The Cell Surface Glycosphingolipis SSEA-3 and SSEA-4 Are Not Essential for Human ESC Pluripotency, Stem Cells, Jan. 2007, pp. 54-62, vol. 25.
Buta, et al., Reconsidering pluripotency tests: Do we still need teratoma assays?, Stem Cell Research, Mar. 26, 2013, pp. 552-562, vol. 11.
Chen, et al., Retinoic acid signaling is essential for pancreas development and promotes endocrine at the expense of exocrine cell differentiation in Xenopus, Developmental Biology, May 4, 2004, pp. 144-160, vol. 271.
Cirulli, et al., Netrins: beyond the brain, Molecular Cell Biology, Apr. 2007, pp. 296-306, vol. 8.

(56) References Cited

OTHER PUBLICATIONS

Furue, et al., Heparin propotes the growth of human embryonic stem cells in a defined serum-free medium, PNAS, Sep. 9, 2008, pp. 13409-13414, vol. 105 Issue 36.
Gibco, Insulin-Transferin-Selenium-X 100X, Invitrogen Cell Culture, Apr. 2005, pp. 1, Form No. 3032.
Gomez, et al., Derivation of cat embryonic stem-like cells from in vitro-produced blastocysts on homologous and heterologous feeder cells, Theriogenology, May 11, 2010, pp. 498-515, vol. 74.
Gordon Weir., Do stem cells hold the key to a future cure for diabetes?, DiabetesVoice, Jun. 2008, pp. 29-31, vol. 53 Issue 2.
Hiemisch, H., et al., Transcriptional Regulation in Endoderm Develoment: Characterization of an Enhancer Controlling Hnf3g Expression by Transgenesis and Targeted Mutagenesis, The EMBO Journal, 1997, 3995-4006, vol. 16(13), MX.
Jean, et al., Pluripotent genes in avian stem cells, Development Growth & Differentitaion, 2013, pp. 41-51, vol. 55.
King, et al., Bioreactor development for stem cell expansion and controlled differentiation, Current Opinion in Chemical Biology, Jul. 25, 2007, pp. 394-398, vol. 11, Elsevier Ltd.
Kunisada, et al., Small molecules induce efficient differentiation into insulin-producing cells from human induced pluripotent stem cells, Stem Cell Research, Oct. 11, 2011, pp. 274-284, vol. 8.
Lavial, et al., Chicken Embryonic Stem Cells as a Non-Mammalian Embryonic Stem Cell Model, Development Growth Differentiation, Jan. 2010, pp. 101-114, vol. 52(1).
Lin, C., et al., Coagulation Dysregulation as a Barrier to Xenotransplantation in the Primate, Transplant Immunology, 2009, pp. 75-80, vol. 21.
Maria-Jesus Obregon, Thyroid hormone and adipocyte differentiation, Thyroid, 2008, pp. 185-195, vol. 18 Issue 2.
McMahon, et al., Noggin-mediated antagonism of BMP signaling is required for growth and patterning of the neural tube and somite, Genes & Development, Mar. 16, 1998, pp. 1438-1452, vol. 12.
Nakase, et al., Myeloid Antigen, CD13, CD14, and/ or CD33 Expression Is Restricted to Certain Lymphoid Neoplasms, Hematopathology, Jun. 1996, pp. 761-768, vol. 105 Issue 6.
Narang, A., et al., Biological and Biomaterial Approaches for Improved Islet Transplantation, Pharmacological Review, Jun. 2006, pp. 194-243, vol. 58(2).
Ouziel-Yahalom, et al., Expansion and redifferentiation of adult human pancreatic islet cells, Biochemical and Biophysical Research Communications, Jan. 19, 2006, pp. 291-298, vol. 341.
Petitte, J., et al., Avian Pluripotent Stem Cells, Mechanisms of Development, 2004, pp. 1159-1168, vol. 121, MX.
Ramiya, et al., Reversal of insulin-dependent diabetes using islets generated in vitro from pancreatic stem cells, Nature Medicine, Mar. 2000, pp. 278-282, vol. 6 Issue 3.
Rother, et al., Challenges facing islet transplantation for the treatment of type 1 diabetes mellitus, The Journal Of Clinical Investigation, 2004, pp. 877-883, vol. 114 Issue 7.
Rowely, et al., Meeting Lot-size Challenges of Manufacturing Adherent Cells for Therapy, Bio Process International, Mar. 2012, pp. 16-22, vol. 10 Issue 3.
Sjo Gren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.
Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.
Suzuken., Differentiation of Multifunctional Stem Cells Using Human Feeder Cells, Research Papers of the Suzuken Memorial Foundation, 2007, pp. 193-197, vol. 2.
Yaldin, et al., Small-molecule inducers of insulin expression in pancreatic α-cells, PNAS, Aug. 24, 2010, pp. 15099-15104, vol. 107 Issue 34.
Yang JW, et al., Evaluation of human MSCs cell cycle, viability and differentiation in micromass culture, Bioheology, 2006, pp. 1-2, vol. 43 Issue (3-4).
Yim,et al., Proliferation and differentiation of human embryonic germ cell derivatives in bioactive polymeric fibrous scaffold, J.Biomater.Sci.Polymer Edn, Jan. 19, 2005, pp. 1193-1217, vol. 16 Issue 10.
Zulewski, et al., Multipotential Nestin-Positive Stem Cells Isolated From Adult Pancreatic Islets Differentiate Ex Vivo Into Pancreatic Endocrine, Exocrine, and Hepatic Phenotypes, Diabetes, 2001, pp. 521-533, vol. 50.
Amit et al., Human Feeder Layers for Human Embryonic Stem Cells, Biology of Reproduction, Jan. 22, 2003, 68, No. 6, 2150-2156, Society for the Study of Reproduction, Inc.
Lavon et al., The Effect of Overexpression of Pdx1 and Foxa2 on the Differentiation of Human Embryonic Stem Cells into Pancreatic Cells, Stem Cells, 2006, 24, 1923-1930, Alpha Med Press Cells.
Blyszczuk et al., Expression of Pax4 in embryonic stem cells promotes differentiation of nestin-positive progenitor and insulin-producing cells, Proceedings of the National Academy of Sciences, Feb. 4, 2003, 100-3, 998-1003, National Academy of Sciences.
Bonner-Weir et al., In vitro cultivation of human islets from expanded ductal tissue, Proceedings of the National Academy of Sciences, Jul. 5, 2000, 97-14, 7999-8004, National Academy of Sciences.
Edlund, Pancreatic Organogenisis—Pancreatic Mechanisims and Implications for Therapy, Nature, Jul. 1, 2002, 3, 524-532, Nature Publishing Group.
Frandsen et al., Activin B mediated induction of Pdx1 in human embryonic stemcell derived embryoid bodies, Biochemical and Biophysical Research Communications, Aug. 15, 2007, 362, 568-574, Elsevier Inc.
Gershengorn et al., Epithelial-to-Mesenchymal Transition Generates Proliferative Human Islet Precursor Cells, Science, Dec. 24, 2004, 306, 2261-2264.
Gadue, et al., WNT and TGB-B Signaling Are Required for the Induction of an in vitro Model of Primitive Streak Formation Using Embryonic Stem Cells, Proceedings of the National Academy of Sciences, Nov. 7, 2006, 103-45, 16806-16811, National Academy of Sciences.
Hadley, et al., Extracellular Matrix Regulates Sertoli Cell Differentiation, Testicular Cord Formation, and Germ Cell Development In Vitro, The Journal of Cell Biology, Oct. 1985, 101, 1511-1522, Rockefeller University Press.
Hori, et al., Growth inhibitors promote differentiation of insulin-producing tissue from embryonic stem cells, Proceedings of the National Academy of Sciences, Dec. 10, 2002, 99-25, 16105-16110, National Academy of Sciences.
Inzunza, et al., Derivation of Human Embryonic Stem Cell Lines in Serum Replacement Medium Using Postnatal Human Fibroblasts as Feeder Cells, Stem Cells, 2005, 23, 544-549, AlphaMed Press.
Jafary, et al., Differential effect of activin on mouse embryonic stem cell differentiation in insulin-secreting cells under nestin-positive selection and spontaneous differentiation protocols, Cell Biology International, 2008, 32, 278-286, Elsevier.
Yang et al., Novel cell immobilization method utilizing centrifugal force to achieve high-density hepatocyte culture in porous scaffold, Journal of Biomed Materials Research, Feb. 27, 2001, 55, 379-386, John Wiley & Sons, Inc.
Vacanti, et al., Selective Cell Transplantation Using Bioabsorbable Artificial Polymers as Matrices, Journal of Pediatric Surgery, Jan. 1988, 23-1, 3-9.
Kleinman et al., Basement Membrane Complexes with Biological Activity, Biochemistry, 1986, 25, 312-318, American Chemical Society.
Kubo et al., Development of definitive endoderm from embryonic stem cells in culture, Development, 2004, 131, 1651-1662, The Company of Biologists.
Ku et al., Committing Embryonic Stem Cells to Early Endocrine Pancreas In Vitro, Stem Cells, 2004, 22, 1205-1217, AlphaMed Press.

(56) References Cited

OTHER PUBLICATIONS

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 72, 42-49.
Lilja et al., Cyclin-dependent Kinase 5 Promotes Insulin Exocytosis, Journal of Biological Chemistry, Jul. 6, 2001, 36-7, 34199-34205, JBC Papers in Press.
Lumelsky, et al., Differentiation of Embryonic Stem Cells to Insulin-Secreting Structures Similar to Pancreatic Islets, Science, 2001, 292, 1389-1394, HighWire Press.
Micallef et al., Retinoic Acid Induces Pdx1-Positive Endoderm in Differentiating Mouse Embryonic Stem Cells, Diabetes, Feb. 2005, 54, 301-305, American Diabetes Association.
Miyamoto et al., Human Placenta Feeder Layers Support Undifferentiated Growth of Primate Embryonic Stem Cells, Stem Cells, 2004, 22, 433-440, AlphaMed Press.
Miyazaki et al., Regulated Expression of pdx-1 Promotes In Vitro Differentiation of Insulin-Producing Cells From Embryonic Stem Cells, Diabetes, Apr. 2004, 53, 1030-1037, American Diabetes Association.
Richards et al., Comparative Evaluation of Various Human Feeders for Prolonged Undifferentiated Growth of Human Embryonic Stem Cells, Stem Cells, 2003, 21, 546-556, AlphaMed Publlishing.
Ricordi et al., Automated Method for Isolation of Human Pancreatic Islets, Diabetes, Apr. 1988, 37, 413-420, American Diabetes Association.
Seabert et al., Cfonal identification of multipotent precursors from adult ~ mouse pancreas that generate neural and pancreatic lineages, Nature Biotechnology, Sep. 2004, 22, 1115-1124, Nature Publishing Group.
Shamblott et al., Derivation of pluripotent stem cells from cultured human primordial germ cells, Developmental Biology, Nov. 1998, 95, 13726-13731, National Academy of Sciences.
Shindler et al., A synthetic nanofibrillar matrix promotes in vivo-like organization and morphogenesis for cells in culture, Biomaterials, Apr. 18, 2005, 26, 5624-5631, Elsevier.
Shiraki et al., TGF-B Signaling Potentiates Differentiation of Embryonic Stem Cells to Pdx-1 Expressing Endodermal Cells, Genes to Cells, 2005, 10, 503-516, Blackwell Publishing Limited.
Shi et al., Inducing Embryonic Stem Cells to Differentiate into Pancreatic β Cells by a Novel Three-Step Approach with Activin A and All-Trans Retinoic Acid, Stem Cells, 2005, 23, 656-662, AlphaMed Press.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 379, 749-756, Biochemical Society.
Soria et al., Insulin-Secreting Cells Derived From Embryonic Stem Cells Normalize Glycemia in Streptozotocin-Induced Diabetic Mice, Diabetes, Feb. 2000, 49, 1-6, American Diabetes Association.
Tulachan et al., TGF-β isoform signaling regulates secondary transition and mesenchymal-induced endocrine development in the embryonic mouse pancreas, Developmental Biology, 2007, 305, 508-521, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 39, 28858-28864, JBC Papers in Press.
Vanderford et al., Multiple kinases regulate mafA expression in the pancreatic beta cell line MIN6, Biochemistry and Biophysics, 2008, 480, 138-142, Elsevier.
Wang et al., Derivation and Growing Human Embryonic Stem Cells on Feeders Derived from Themselves, Stem Cells, 2005, 23, 1221-1227, AlphaMed Press.
Wei et al., Cdk5-dependent regulation of glucose-stimulated insulin secretion, Nature Medicine, Sep. 11, 2005, 11-10, 1104-1108, Nature Publishing Group.
Wiles et al., Embryonic Stem Cell Development in a Chemically Defined Medium, Experimental Cell Research, 1999, 247, 241-248, Academic Press.
Zhang et al., MafA Is a Key Regulator of Glucose-Stimulated Insulin Secretion, Molecular and Cellular Biology, Jun. 2005, 25-12, 4969-4976, American Society for Microbiology.
Zhao et al., The Islet B Cell-enriched MafA Activator is a Key Regulator of Insulin Gene Transcription, Journal of Biological Chemistry, Mar. 25, 2005, 280-12, 11887-11894, The Amerian Society for Biochemistry and molecular Biology, Inc.
Prichard, et al., Adult Adipose Derived Stem Cell Attachment to Biomaterials, Biomaterials, 2006, vol. 28, No. 6, pp. 936-946.
Arai, et al., Purification of Recombinant Activin A Using the Second Follistatin Domain of Follistatin-Related Gene (FLRG), Protein Expression & Purification, 2006, vol. 49, pp. 78-82.
Armstrong, et al., The Role of P13K/AKT, MAPK/ERK and NFKκβ Signalling in the Maintenance of Human Embryonic Stem Cell Pluripotency and Viability Highlighted by Transcriptional Profiling and Functional Analysis, Human Molecular Genetics, 2006, vol. 15, No. 11, pp. 1894-1913.
McKiernan, et al., Directed Differentiation of Mouse Embryonic Stem Cells into Pancreatic-Like or Neuronal-and Glial-Like Phenotypes, Tissue Engineering, 2007, vol. 13, No. 10, pp. 2419-2430.
Shiraki, et al., Guided Differentiation of Embryonic Stem Cells into Pdx1-Expressing Regional-Specific Definitive Endoderm, Stem Cells, 2008, vol. 26, pp. 874-885.
Paling, et al., Regulation of Embryonic Stem Cell, Self-Renewal by Phosphoinositide 3-kinase-dependent Signaling, Journal of Biological Chemistry, 2004, vol. 279, No. 46, pp. 48063-48070.
Balajthy, et al., Molecular therapies., 2011, pp. 1-6.
Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.
Chen, et al., Scalable GMP Compliant Suspension Culture System for Human ES Cells, Stem Cell Research, 2012, pp. 388-402, vol. 8.
Condic, et al., Alternative Sources of Pluripotent Stem Cells: Ethical and Scientific Issues Revisited, Stem Cells and Development, 2010, pp. 1121-1129, vol. 19 Issue 8, Mary Ann Liebert, Inc.
Daheron, et al., LIF/STAT3 Signaling Fails to Maintain Self-Renewal of Human Embryonic Stem Cells, Stem Cells, 2004, pp. 770-778, vol. 22.
Findikli, et al., Establishment and characterization of new human embryonic stem cell lines, Reproductive BioMedicine Online, Mar. 3, 2005, pp. 617-627, vol. 10 Issue 5.
Guillemain, et al., Glucose Is Necessary for Embryonic Pancreatic Endocrine Cell Differentiation, The Journal Of Biological Chemistry, May 18, 2007, pp. 15228-15237, vol. 282 Issue 20.
Guo, et al., Efficient differentiation of insulin-producing cells from skin-derived stem cells, Cell Proliferation, 2009, pp. 49-62, vol. 42.
Kehoe, et al., Scalable Stirred-Suspension Bioreactor Culture of Human Pluripotent Stem Cells, Tissue Eng Part A, 2010, pp. 405-421, vol. 16 Issue 2.
Kim, et al., Reprogrammed Pluripotent Stem Cells from Somatic Cells, International Journal of Stem Cells, 2011, pp. 1-8, vol. 4 Issue 1.
Lee, et al., Available human feeder cells for the maintance of human embryonic stem cells, Reproduction, 2004, pp. 727-735, vol. 128.
Ludwig, et al., Defined, Feeder-Independent Medium for human Embryonic Stem Cell Culture, Current Protocols In Stem Cell Biology, 2007, pp. 1C.2.1-1C.2.16, vol. 1, John Wiley & Sons, Inc.
Maimets, et al., Activation of p53 by nutlin leads to rapid differentiation of human embryonic stem cells, Oncogene, Jun. 2, 2008, pp. 5277-5287, vol. 27.
Misiti, et al., 3,5,30-Triiodo-L-Thyronine Enhances the Differentiation of a Human Pancreatic Duct Cell Line (hPANC-1) Towards a b-Cell-Like Phenotype, Journal of Cellular Physiology, 2005, pp. 286-296, vol. 204.
Nekrasov, et al., Induced pluripotent stem cells as a model for studying human diseases, Cellular Transplantology and Tissue Engineering, 2011, pp. 32-37, vol. 6 Issue 2 (English Abstract).

(56) References Cited

OTHER PUBLICATIONS

Olmer, et al., Long Term Expansion of Undifferentiated Human iPS and ES Cells in Suspension Culture Using Defined Medium, Stem Cell Research, 2010, pp. 51-64, vol. 5.
Osafune, et al., Marked differences in differentiation propensity among human embryonic stem cell lines, Nature Biotechnology, Feb. 17, 2008, pp. 313-315, vol. 26 Issue 3.
Thomson, Bioprocessing of Embryonic Stem Cells for Drug Disvoery, Trends in Biotechnology, 2007, pp. 224-230, vol. 25, No. 5.
Wang, et al., Scalable expansion of human induced pluripotent stem cells in the defined xeno-free E8 medium under adherent and suspension culture conditions, Stem Cell Research, Nov. 2013, pp. 1103-1116, vol. 11 Issue 3.
Zhu, et al., A Small Molecule Primes Embryonic Stem Cells for Differentiation, Cell Stem Cell, May 8, 2009, pp. 416-426, vol. 4.
International Search Report dated Mar. 1, 2010 for Appln. No. PCT/US2009/034558.
Rebollar et al.: "Proliferation of Aligned Mammalian Cells on Laser-Nonostructured Polystyrene" Biomaterials, Elsevier Science Publishers BV., Barking, GB, vol. 29, No. 12, Jan. 31, 2008, pp. 1796-1806, XP022499077.
D.O.H. Teare, N. Emmison, C. Ton-That, and R.H. Bradley: "Cellular Attachment to Ultraviolet Ozone Modified Polystyrene Surfaces" Langmiur, vol. 16, No. 6, Jan. 21, 2000 pp. 2818-2824 XP002566368.
CH. C. Dupont-Gillain, Y. Adriaensen, S. Derclaye, and P.G. Rouxhet: "Plasma-Oxidized Polystyrene: Wetting Properties and Surface Reconstruction" Langmuir, vol. 16, No. 21, Sep. 19, 2000, pp. 8194-8200, XP002566369.
Bigdeli et al. (J. Biotechnol. 133:146-153, 2008).
Brevig et al., Biomaterials 26:3039-3053, 2005.
Buzzard et al. Nature Biotechnol. 22:381-382, 2004.
Cheon et al (BioReprod DOI:10.1095/biolreprod.105.046870;; Oct. 19, 2005.
Cheon et al BioReprod 77 2007.
Curr. Top. Dev. Biol. 38:133 ff., 1998.
D'Amour et al., Nature Biotechnol. 23:1534-1541, 2005.
D'Amour et al., Nature Biotechnol. 24:1392-1401, 2006.
Draper et al. Nature Biotechnol. 22:53-54, 2004.
Graham et al., (J. Gen. Virol. 36:59-72, 1977).
Harb Nicole et al. "The Rho-Rock-Myosin Signaling Axis Determines Cell-Cell Integrity of Self-Renewing Pluripotent Stem Cells", vol. 3, No. 8, Aug. 2008, Article: e3001. XP002530386 oi:10.1371/journal.pone.0003001, Aug. 2008).
Hasegawa et al. Stem Cells 24:2649-2660, 2006.
Heng et al. Biotechnology and Applied Biochemistry 47:33-37, 2007.
Koyanagi, M et al (J Neurosci Res. Sep. 7, 2007 [Epub ahead of print]).
Koyanagi, Masaomi et al.: "Inhibition of the Rho/Rock pathway reduces apoptosis during transplantaion of embryonic stem cell-derived neural precursors." Journal of Neuroscience Research Feb. 1, 2008, vol. 86, No. 2, pp. 270-280, XP002530383.
Krawetz Roman J. et al.: "Human Embryonic Stem Cells: caught between a Rock Inhibitor and a hard place." Bioessays: News and Reviews in Molecular, Cellular and Developmental Biology Mar. 2009, vol. 31, No. 3, Mar. 2009 pp. 336-343, XP002530382.
Laplante Isabel et al.: "RhoA/Rock and Cdc42 regulate cell-cell contact and N-cadherin protein level during neurodetermination of P19 embryonal stem cells" Journal of Neurobiology, John Wiley and Sons., New York, NY US, vol. 60, No. 3, Sep. 5, 2004.
Levenstein et al Stem Cells 24: 568-574, 2006.
McLean et al., Stem Cells 25:29-38, 2007.
Mitalipova et al. Nature Biotechnol. 23:19-20, 2005.
Nicolas et al. Stem Cells Dev. 16:109-118, 2007.
Pardo, A.M. et al.: "Corning Cell BIND Surface: An Improved Surface for Enhanced Cell Attachment", Corning Technical Report, 2005, XP002530385.
Peerani et al. (EMBO Journal 26:4744-4755, 2007).
Proc. Natl. Acad. Sci. U.S.A. 92:7844, 1995.
Reubinoff et al. (Nature Biotechnol. 18:399-404, 2000).
Shen and Horbett, J. Biomed. Matter. Res. 57:336-345, 2001.
Shinozaki et al. Development 131:1651-1662, 2004.
Sidhu et al. Stem Cells Dev. 15:61-69, 2006.
Stojkovic et al. (Stem Cells 23:895-902, 2005).
Takahashi et al., Cell 131: 1-12 (2007).
Takehara Toshiyuki et al.: "Rho-associated kinase inhibitor Y-27632 promotes survival of cynomolgus monkey embryonic stem cells." XP002530395 Molecular Human Reproduction Nov. 2008, vol. 14, No. 11, Nov. 2008, pp. 627-634.
Thompson et al. (Science 282:1145-1147, 1998).
Ungrin Mark D. et al.: Reproducible, ultra high-throughput formation of multicelluar organization from single cell suspension-derived human embryonic stem cell aggregates.: PLOS One 2008, vol. 3, No. 2, Feb. 13, 2008, pp. e1565, XP002530384.
Vallier et al. (J. Cell Sci. 118:4495-4509, 2005).
Van Kooten T.G. et al.: "Plasma-treated polystyrene surfaces: model surfaces for studying cell-biomaterial interactions" Biomaterials, Elsevier Science Publishers BV., Barking, GB, vol. 25, No. 10, May 1, 2004, pp. 1735-1747, XP004485087.
Wanatabe et al. (Nature Biotechnol. 25:681-686, 2007).
Xu et al. (Nature Biotechnology 19:971-974, 2001).
Xu et al. (Stem Cells 22: 972-980, 2004).
Yoneda et al (J. Cell Biol. 170: 443-453, Aug. 3, 2005).

* cited by examiner

Figure 9
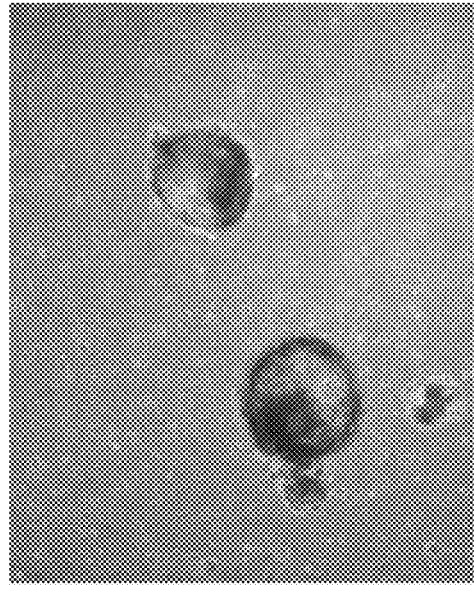
P11 on Surface #3 (7s)
10 days culture
DMEM:F12 w/ 10% FBS
Low Binding Plate
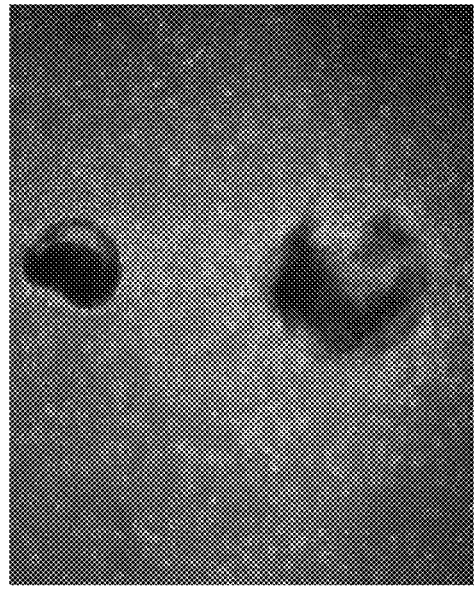
P10 on Surface #4 (1s)

Figure 10
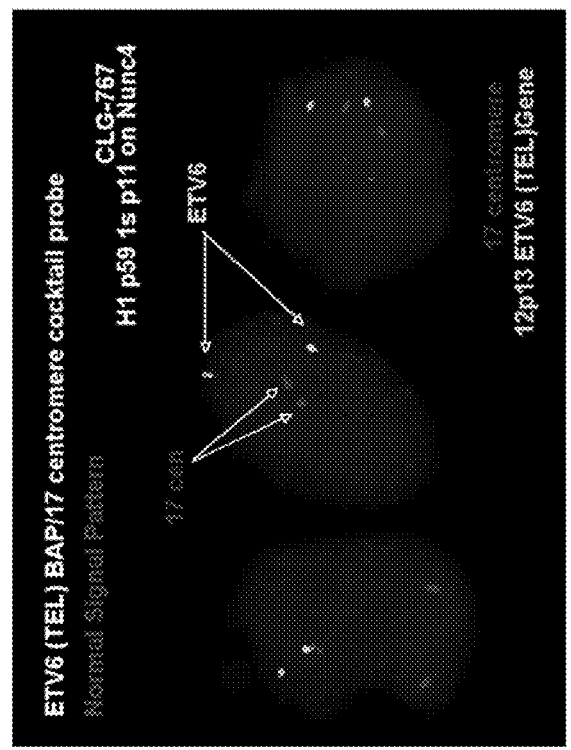
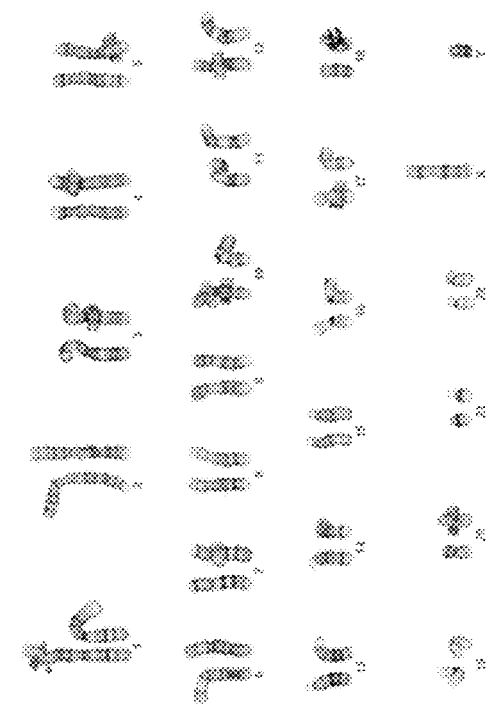
H1p59 p10 on Surface #4 (1s)

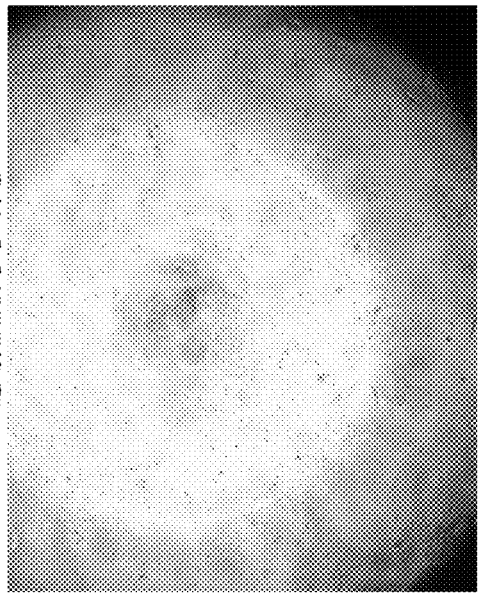
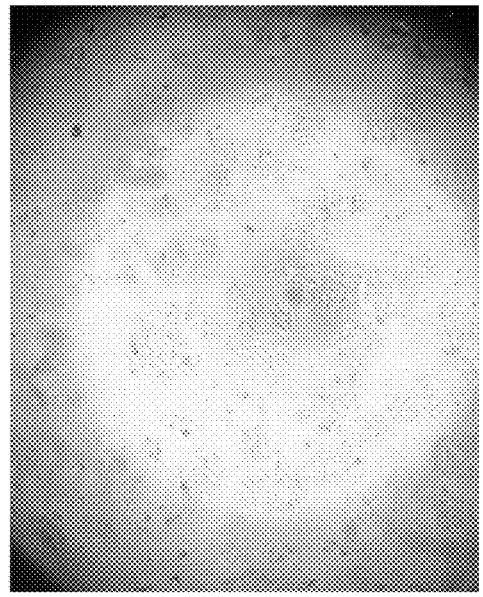
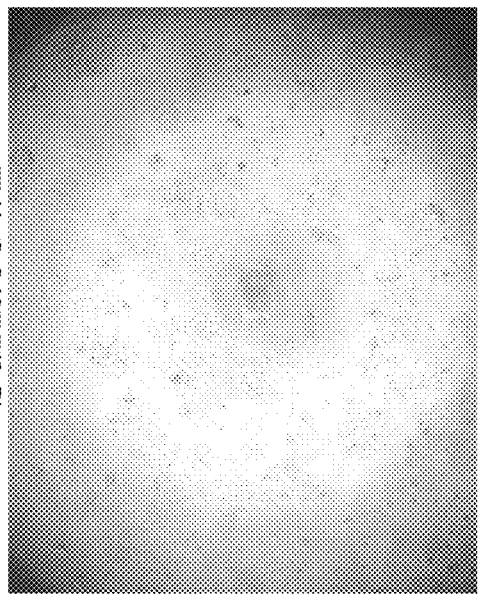
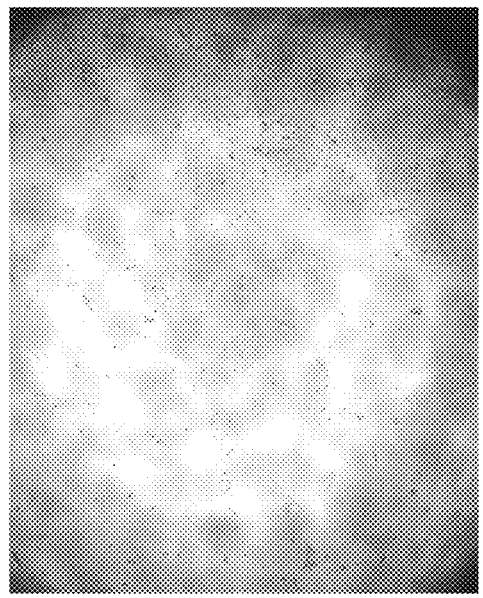
Figure 21

Figure 27 No Colony binding observed on Surface #14 or #15 without Y27632

Figure 33
a)
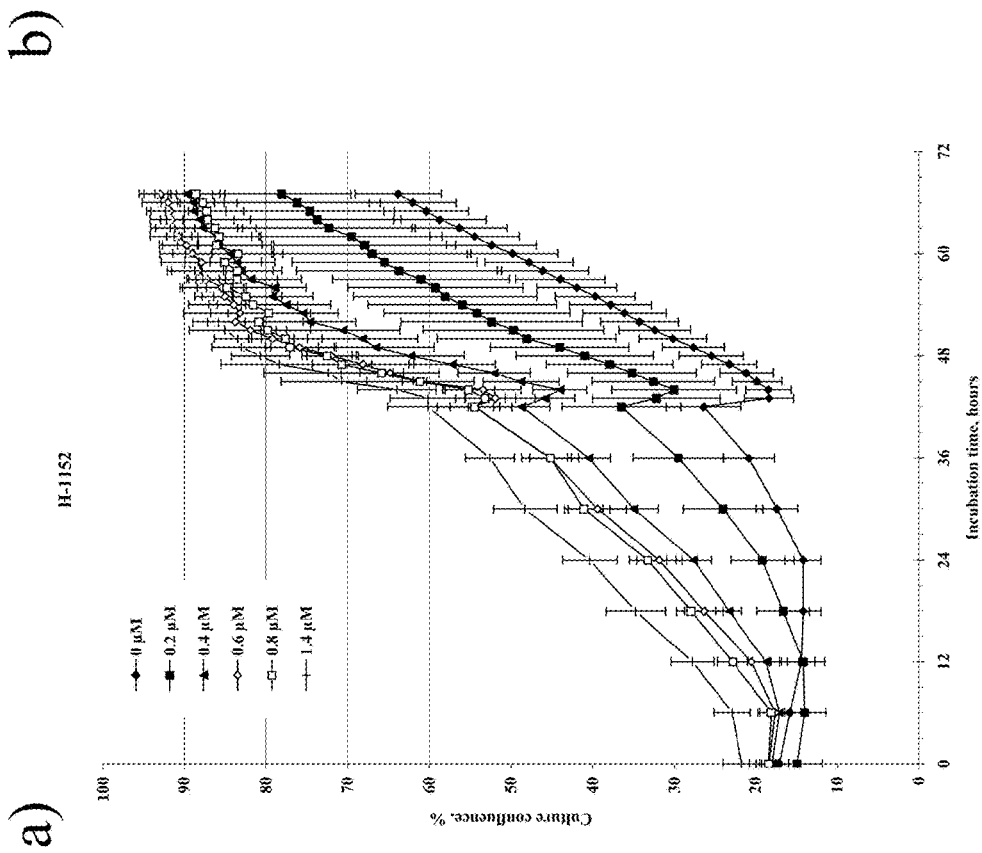
b)
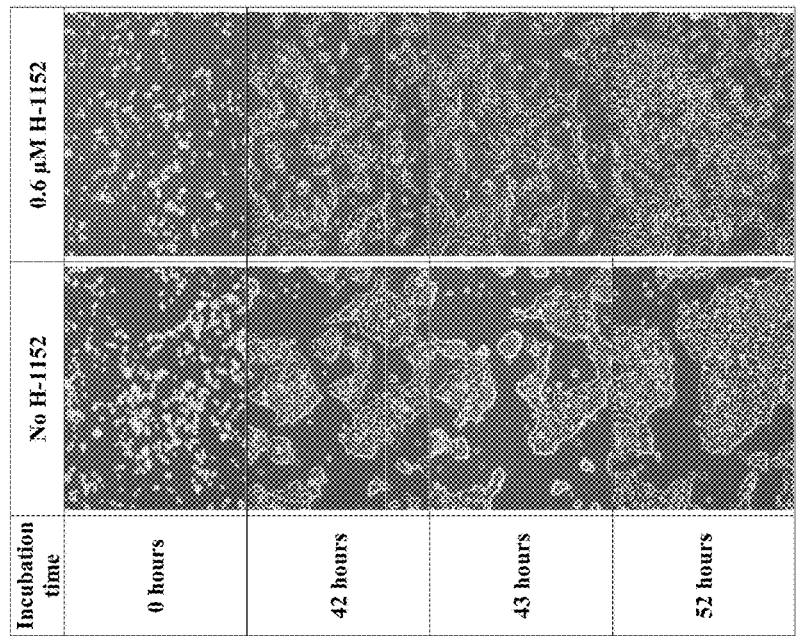

ature.
METHODS, SURFACE MODIFIED PLATES AND COMPOSITIONS FOR CELL ATTACHMENT, CULTIVATION AND DETACHMENT This application claims priority to provisional application Ser. No. 61/030,544, filed Feb. 21, 2008.

FIELD OF THE INVENTION

The present invention relates to the field of mammalian cell culture, and provides methods and compositions for cell attachment to, cultivation on, and detachment from a solid substrate surface containing from at least about 0.5% N, a sum of O and N of greater than or equal to 17.2% and a contact angle of at least about 13.9 degrees, lacking a feeder cell layer and lacking an adlayer. In one embodiment of the present invention, the cells are treated with a compound capable of inhibiting Rho kinase activity. In another embodiment, the cells are treated with a compound capable of inhibiting Rho activity.

BACKGROUND

Cultivation of mammalian cells is one of many processes in the life and health sciences. Vessels for mammalian cell culture and analysis involving anchorage-dependent cells are often made of glass or a polymer, such as, for example, polystyrene, that frequently requires additional surface treatment to allow the cells to attach to the surface of the vessel. Such treatments may include applying an adlayer on the surface, for example, by adsorption, grafting or plasma polymerization techniques. Alternatively, the surface treatment may be via chemical modification of the vessel surface itself, which can be achieved by, for example, atmospheric corona, radio frequency vacuum plasma, DC glow discharge, and microwave plasma treatments. These surface treatments change the composition of elements and chemical groups in the surface. The particular chemistry that results depends on the surface treatment method, energy, and time, as well as the composition of the gasses used.

For example, U.S. Pat. No. 5,449,383 discloses a substrate comprising a bulk polymeric material; and a thin polymeric layer which is suitable for supporting cell growth, comprising a reorientation resistant polymer comprising plasma-polymerized amide monomers presenting amide groups for the attachment of cells, wherein said amide monomers are selected from the group of dimethyl formamide and amides having the formula $R^1$—CO—N($R^2$)$R^3$ wherein $R^1$ is an aliphatic, alicyclic, or aromatic group, each of which may be optionally substituted by halogen atoms or hydroxyl groups, and $R^2$ and $R^3$ are each independently hydrogen or an alkyl group, and wherein said thin polymer layer promotes attachment and proliferation of said cells.

In another example, EP0348969A1 discloses a method for endothelialization of a polymeric surface comprising contacting a polymeric surface with a plasma generated from a gaseous material comprising nitrogen whereby said polymeric surface is modified to contain surface amino groups, and applying to said modified surface sufficient endothelial cells to form a confluent layer of cells on said amino group-containing surface without a requirement for cell proliferation.

In another example, EP0092302A2 discloses a method for influencing the growth of cell culture in a growth media on a substrate, characterized in that the surface chemistry of the substrate is modified by subjecting the surface of the substrate to a plasma, which is produced from carbon, hydrogen, oxygen, nitrogen, sulphur, phosphorus, a halogen, or a compound of any one of these elements.

In another example, U.S. Pat. No. 6,617,152B2 discloses an apparatus for treating a polymeric substrate surface comprising: (a) a gas inlet, a microwave energy source and a plasma mixing chamber, the plasma mixing chamber in fluid communication with both the gas inlet and the microwave energy source; (b) a dual chambered treatment area having an inner treatment chamber contained within an outer treatment chamber, said inner treatment chamber having an opening in fluid communication with said outer chamber; (c) said plasma mixing chamber in fluid communication with said outer treatment chamber by means of an aperture; (d) a vacuum outlet line attached to said outer chamber; and (e) whereby said opening in said inner treatment chamber is aligned with said aperture, said opening being spaced from said aperture at predetermined distance.

In one example, US2003/0180903A1 discloses a polymeric substrate having a working surface upon which cells can be cultured wherein the surface oxygen content is at least 25 percent as measured by electron microscopy for chemical analysis at depth about 50 Angstroms.

In one example, WO2006114098 discloses a micro-structured biocompatible material for surgical implants and cell guiding tissue culture surfaces. The microstructure of the biomaterial surface is selected to promote growth of undifferentiated ES cells; promote neuronal differentiation of ES cells; or promote differentiation of ES cells.

In another example, Bigdeli et al. (J. Biotechnol. 133: 146-153, 2008) describes a method of adaptation and/or selection of human ES cells to be cultivated without differentiation under feeder-cell free conditions and without prior treatment of the solid substrate surface with extracellular matrix protein, involving (i) changing media from medium conditioned by human diploid embryonic lung fibroblasts to medium conditioned by neonatal chondrocytes; (ii) then passaging the cells enzymatically from the mouse embryonic feeder cell layer to Matrigel™-treated plates, then to Costar™ plates, and, finally, to Primaria™ plates; and (iii) changing back to the first used medium again. Very few of the human ES cells subjected to this method gave rise to established cell lines, suggesting that this method involves selection of human ES cells to the culture conditions.

Surface treatments that change the composition of elements and chemical groups in the surface itself have successfully been used for preparing polymer solid substrates for the culture of many types of mammalian cells. However, there are significant limitations in terms of poor attachment and/or cultivation using certain types of mammalian cells, for example, pluripotent stem cells and human embryonic kidney (HEK) 293 cells.

Graham et al., (J. Gen. Virol. 36:59-72, 1977) disclose the generation of the cell line HEK293.

HEK293 cell attachment may be enhanced by making an adlayer on the solid substrate surface, using, for example, extracellular matrix proteins, polylysine, polyornithine, or polyethyleneimine, before adding the HEK293 cells to the culture vessel. Preparing the adlayer is, however, time-consuming, and typically results in a non-sterile solid substrate with a shorter shelf life than the bare solid substrate.

Therefore, there is a significant need for methods and materials for enhancing the attachment of HEK293 cells to solid substrates lacking an adlayer.

Current methods of culturing pluripotent stem cells, in particular, embryonic stem (ES) cells require complex culture conditions, such as, for example, culturing the embryonic stem cells on a solid substrate surface with a feeder cell layer, or on a solid substrate surface with an adlayer of extracellular matrix protein. Culture systems that employ these methods often use feeder cells or extracellular matrix proteins obtained from a different species than that of the stem cells being cultivated (xenogeneic material). Media obtained by exposure to feeder cells, that is, media conditioned by cells other than undifferentiated ES cells, may be used to culture the ES cells, and media may be supplemented with animal serum.

For example, Reubinoff et al. (Nature Biotechnol. 18:399-404, 2000) and Thompson et al. (Science 282:1145-1147, 1998) disclose the culture of ES cell lines from human blastocysts using a mouse embryonic fibroblast feeder cell layer.

In another example, Xu et al. (Nature Biotechnology 19:971-974, 2001) discloses the use of Matrigel™ and laminin for treating solid substrate surfaces before feeder-cell free cultivation of human ES cells without differentiation.

In another example, Vallier et al. (J. Cell Sci. 118:4495-4509, 2005) discloses the use of fetal bovine serum for treating solid substrate surfaces before feeder-cell free cultivation of human ES cells without differentiation.

In another example, WO2005014799 discloses conditioned medium for the maintenance, proliferation and differentiation of mammalian cells. WO2005014799 state: "The culture medium produced in accordance with the present invention is conditioned by the cell secretion activity of murine cells, in particular, those differentiated and immortalized transgenic hepatocytes, named MMH (Met Murine Hepatocyte)."

In another example, Wanatabe et al. (Nature Biotechnol. 35:681-686, 2007) state "a ROCK inhibitor permits survival of dissociated human embryonic stem cells", and demonstrate reduced dissociation-induced apoptosis, increases cloning efficiency (from approximately 1% to approximately 27%) and facilitation of subcloning after gene transfer, using mouse embryonic fibroblasts as feeder cells, collagen and Matrigel™ as extracellular matrix protein, and Y-27632 or Fasudil for inhibition of ROCK. Furthermore, dissociated human ES cells treated with Y-27632 were protected from apoptosis in serum-free suspension culture.

In another example, Peerani et al. (EMBO Journal 26:4744-4755, 2007) state "Complexity in the spatial organization of human embryonic stem cell (hESC) cultures creates heterogeneous microenvironments (niches) that influence hESC fate. This study demonstrates that the rate and trajectory of hESC differentiation can be controlled by engineering hESC niche properties. Niche size and composition regulate the balance between differentiation-inducing and -inhibiting factors. Mechanistically, a niche size-dependent spatial gradient of Smad1 signaling is generated as a result of antagonistic interactions between hESCs and hESC-derived extra-embryonic endoderm (ExE). These interactions are mediated by the localized secretion of bone morphogenetic protein-2 (BMP2) by ExE and its antagonist, growth differentiation factor-3 (GDF3) by hESCs. Micropatterning of hESCs treated with small interfering (si) RNA against GDF3, BMP2 and Smad1, as well treatments with a Rho-associated kinase (ROCK) inhibitor demonstrate that independent control of Smad1 activation can rescue the colony size-dependent differentiation of hESCs. Our results illustrate, for the first time, a role for Smad1 in the integration of spatial information and in the niche-size dependent control of hESC self-renewal and differentiation."

In another example, Koyanagi, M et al (J Neurosci Res. 2007 Sep. 7 [Epub ahead of print]) state "Rho-GTPase has been implicated in the apoptosis of many cell types, including neurons, but the mechanism by which it acts is not fully understood. Here, we investigate the roles of Rho and ROCK in apoptosis during transplantation of embryonic stem cell-derived neural precursor cells. We find that dissociation of neural precursors activates Rho and induces apoptosis. Treatment with the Rho inhibitor C3 exoenzyme and/or the ROCK inhibitor Y-27632 decreases the amount of dissociation-induced apoptosis (anoikis) by 20-30%. Membrane blebbing, which is an early morphological sign of apoptosis; cleavage of caspase-3; and release of cytochrome c from the mitochondria are also reduced by ROCK inhibition. These results suggest that dissociation of neural precursor cells elicits an intrinsic pathway of cell death that is at least partially mediated through the Rho/ROCK pathway. Moreover, in an animal transplantation model, inhibition of Rho and/or ROCK suppresses acute apoptosis of grafted cells. After transplantation, tumor necrosis factor-alpha and pro-nerve growth factor are strongly expressed around the graft. ROCK inhibition also suppresses apoptosis enhanced by these inflammatory cytokines. Taken together, these results indicate that inhibition of Rho/ROCK signaling may improve survival of grafted cells in cell replacement therapy.).

In another example, Yoneda et al (J. Cell Biol. 170: 443-453, Aug. 3, 2005) states "the homologous mammalian rho kinases (ROCK I and II) are assumed to be functionally redundant, based largely on kinase construct overexpression. As downstream effectors of Rho GTPases, their major substrates are myosin light chain and myosin phosphatase. Both kinases are implicated in microfilament bundle assembly and smooth muscle contractility. Here, analysis of fibroblast adhesion to fibronectin revealed that although ROCK II was more abundant, its activity was always lower than ROCK I. Specific reduction of ROCK I by siRNA resulted in loss of stress fibers and focal adhesions, despite persistent ROCK II and guanine triphosphate-bound RhoA. In contrast, the microfilament cytoskeleton was enhanced by ROCK II down-regulation. Phagocytic uptake of fibronectin-coated beads was strongly down-regulated in ROCK II-depleted cells but not those lacking ROCK I. These effects originated in part from distinct lipid-binding preferences of ROCK pleckstrin homology domains. ROCK II bound phosphatidylinositol $3,4,5P_3$ and was sensitive to its levels, properties not shared by ROCK I. Therefore, endogenous ROCKs are distinctly regulated and in turn are involved with different myosin compartments."

In another example, Harb et al (PLoS ONE 3(8): e3001. oi:10.1371/journal.pone.0003001, August 2008) discloses an essential role of the Rho-Rock-Myosin signaling axis for the regulation of basic cell-cell communications in both mouse and human ES cells, and would contribute to advance [sic] in medically compatible xeno-free environments for human pluripotent stem cells.

The use of xenogeneic material may be unsuitable for certain applications utilizing pluripotent stem cells. Alternative materials may be used. For example, Stojkovic et al. (Stem Cells 23:895-902, 2005) discloses the use of human serum for treating solid substrate surfaces before feeder-cell free cultivation of human ES cells without differentiation.

An alternative culture system employs serum-free medium supplemented with growth factors capable of promoting the proliferation of ES cells.

For example, Cheon et al. (BioReprod DOI: 10.1095/biolreprod.105.046870; 19 Oct. 2005) disclose a feeder-cell free, serum-free culture system in which ES cells are maintained in unconditioned serum replacement medium supplemented with different growth factors capable of triggering ES cell self-renewal.

In another example, Levenstein et al. (Stem Cells 24:568-574, 2006) disclose methods for the long-term culture of human ES cells in the absence of fibroblasts or conditioned medium, using media supplemented with basic fibroblast growth factor (FGF).

In another example, US20050148070 discloses a method of culturing human ES cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a FGF capable of activating a FGF signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of basic FGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes nonessential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In another example, WO2005065354 discloses a defined, isotonic culture medium that is essentially feeder-free and serum-free, comprising: a. a basal medium; b. an amount of basic fibroblast growth factor sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

Pluripotent stem cells provide a potential resource for research and drug screening. At present, large-scale culturing of human ES cell lines is problematic and provides substantial challenges. A possible solution to these challenges is to passage and culture the human ES cells as single cells. Single cells are more amenable to standard tissue culture techniques, such as, for example, counting, transfection, and the like.

For example, Nicolas et al. provide a method for producing and expanding human ES cell lines from single cells that have been isolated by fluorescence-activated cell sorting following genetic modification by lentivirus vectors (Stem Cells Dev. 16:109-118, 2007).

In another example, US patent application US2005158852 discloses a method "for improving growth and survival of single human embryonic stem cells. The method includes the step of obtaining a single undifferentiated hES cell; mixing the single undifferentiated cell with an extracellular matrix to encompass the cell; and inoculating the mixture onto feeder cells with a nutrient medium in a growth environment".

In another example, Sidhu et al. (Stem Cells Dev. 15:61-69, 2006) describe the first report of three human ES cell clones, hES 3.1, 3.2 and 3.3, derived from the parent line hES3 by sorting of single-cell preparations by flow cytometry.

However, passage and culture of human ES cells as single cells leads to genetic abnormalities and the loss of pluripotency. Culture conditions are important in the maintenance of pluripotency and genetic stability. Generally, passage of human ES cell lines is conducted manually or with enzymatic agents such as collagenase, liberase or dispase.

For example, Draper et al. note the presence of "karyotypic changes involving the gain of chromosome 17q in three independent human embryonic stem cell lines on five independent occasions." (Nature Biotechnol. 22:53-54, 2004).

In another example, Buzzard et al. state, "we have only ever detected one karyotype change event . . . the culture methods used may have had some bearing on our results, given that our methods are distinctly different from those used by most other groups. Typically we passage human ES cells after 7 days by first dissecting the colony with the edge of a broken pipette . . . . No enzymatic or chemical methods of cell dissociation are incorporated into this method. We speculate that this may explain the relative cytogenetic resilience of hES (human ES) cells in our hands." (Nature Biotechnol. 22:381-382, 2004).

In another example, Mitalipova et al. state "bulk passage methods . . . can perpetuate aneuploid cell populations after extended passage in culture, but may be used for shorter periods (up to at least 15 passages) without compromising the karyotypes . . . it may be possible to maintain a normal karyotype in hES cells under long-term manual propagation conditions followed by limited bulk passaging in experiments requiring greater quantities of hES cells than manual passage methods, alone, can provide". (Nature Biotechnol. 23:19-20, 2005).

In another example, Heng et al. state "the results demonstrated that the second protocol (trypsinization with gentle pipetting) is much less detrimental to cellular viability than is the first protocol (collagenase treatment with scratching).

This in turn translated to higher freeze-thaw survival rates." (Biotechnology and Applied Biochemistry 47:33-37, 2007).

In another example, Hasegawa et al. state, "we have established hESC sublines tolerant of complete dissociation. These cells exhibit high replating efficiency and also high cloning efficiency and they maintain their ability to differentiate into the three germ layers." (Stem Cells 24:2649-2660, 2006).

Therefore, there is a significant need for methods and compositions for the cultivation of mammalian cells, including cultivation of pluripotent stem cells in the absence of feeder cells and an adlayer, while maintaining the pluripotency of the cells.

SUMMARY

In one embodiment, the present invention provides methods and compositions for the attachment, cultivation and detachment of cells to a solid substrate surface containing from at least about 0.5% N, a sum of O and N of greater than or equal to 17.2% and a contact angle of at least about 13.9 degrees, lacking a feeder cell layer and lacking an adlayer.

In one embodiment, the present invention provides a method to enhance the attachment of cells to a surface containing from at least about 0.5% N, a sum of O and N of greater than or equal to 17.2% and a contact angle of at least about 13.9 degrees, lacking a feeder cell layer and lacking an adlayer, comprising the steps of:
a. Obtaining a suspension of cells,
b. Treating the suspension of cells with at least one compound selected from the group consisting of: a compound capable of inhibiting Rho kinase activity, and a compound capable of inhibiting Rho activity, and
c. Adding the suspension of cells to the surface and allowing the cells to attach.

In one embodiment, the cells are maintained in culture after the cells attach to the surface. In an alternate embodiment the at least one compound is removed.

In one embodiment, the cells are detached from the surface by removing the at least one compound.

In one embodiment the suspension of cells is a suspension of clusters of cells. In an alternate embodiment, the suspension of cells is a suspension of single cells.

In one embodiment, the cells are pluripotent stem cells. In an alternate embodiment, the cells are stem cells.

In one embodiment, the present invention provides a method to enhance the attachment of cells to a surface containing from at least about 0.9% N, a sum of O and N of greater than or equal to 22.3% and a contact angle of at least about 13.9 degrees, lacking a feeder cell layer and lacking an adlayer, comprising the steps of:
a. Obtaining a suspension of cells, and
b. Adding the suspension of cells to the surface and allowing the cells to attach.

BRIEF DESCRIPTION OF THE DRAWINGS

FIG. 9 shows the ability of human ES cells cultured on surface modified plates to form embryoid bodies.

FIG. 10 shows the karyotype of human ES cells cultured on surface modified plate 4.

FIG. 21 depicts images of cells from the human ES cell line H9, that were passaged as single cells, seeded on to surface modified plates 2-4 and 13 in a 96-well format. The MEF conditioned media contained 10 µM of Y-27632. Images were taken 48 hours after seeding.

FIG. 33 shows the effect of H-1152 and Surface 4 on HEK293-cell attachment and morphology. HEK293 cells were seeded in Multidish 12-well plates in EMEM medium supplemented with 10% fetal bovine serum and H-1152, and incubated for 67 hours in an automated, in-incubator microscope. Growth curves in A and photomicrographs in B show the general effect of H-1152 on HEK293-cell attachment and growth on surface 4, and the effect of a change of medium on HEK293-cell attachment and morphology on surface 4 in the presence or absence of H-1152.

DETAILED DESCRIPTION

Figure 1:
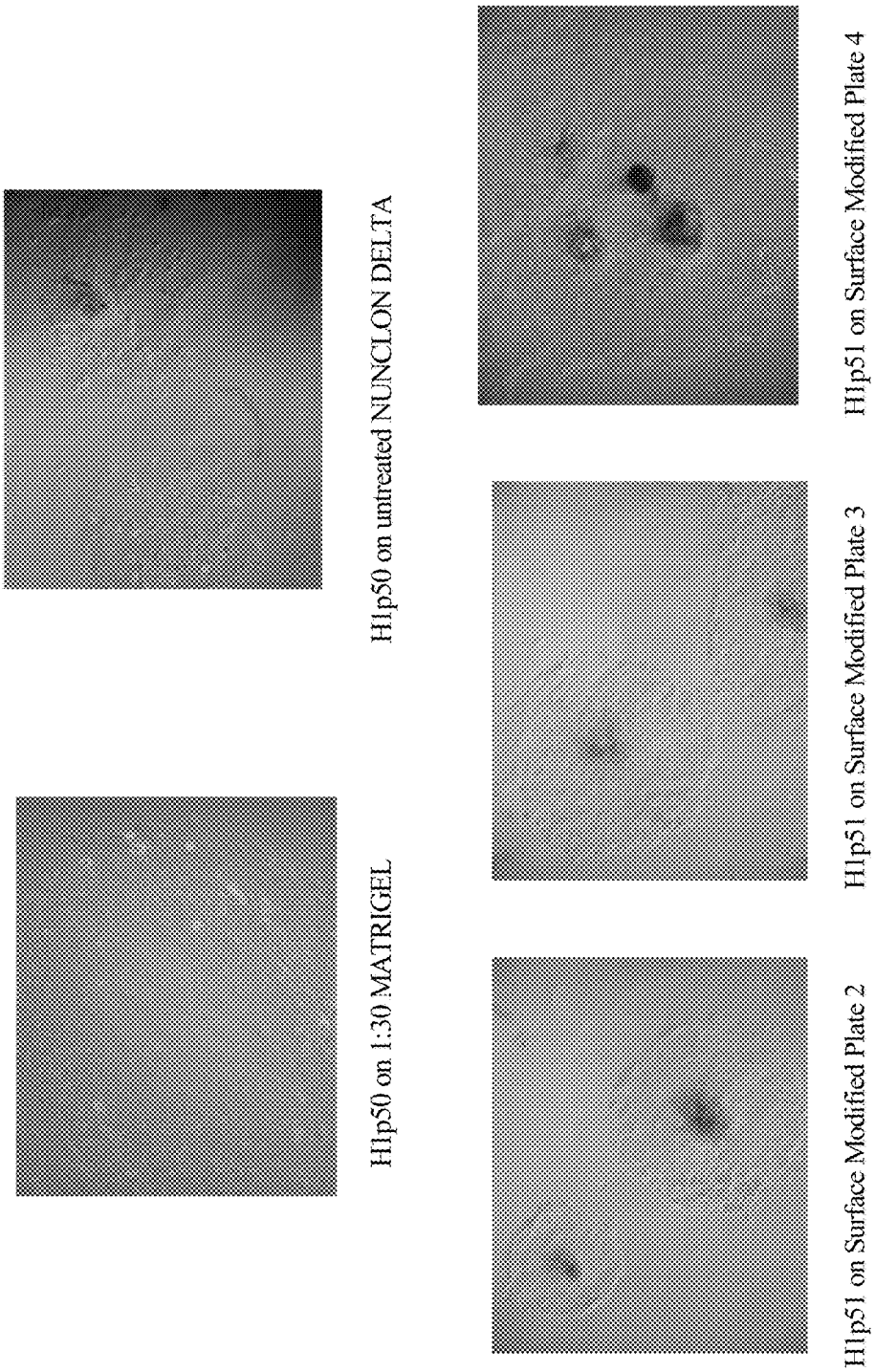
FIG. 1 shows phase contrast micrographs (4×) of cells of the human ES cell line H1 that were passaged twice as clusters with LIBERASE on surface modified plates 2, 3 or 4. Images of cells of the human ES cell line H1, cultured on plates treated with a 1:30 dilution of Matrigel™ Nunclon Delta™ plates are also shown.

For clarity of disclosure, and not by way of limitation, the detailed description of the invention is divided into the following subsections that describe or illustrate certain features, embodiments or applications of the present invention.

Definitions

"Adlayer" as used herein refers to a layer that is formed on a surface of a solid substrate, by attaching molecules to the surface by either covalent (also known as grafting) or non-covalent (also known as adsorption) bonds. Molecules used in making an adlayer can, for example, be proteinaceous molecules, which may include, for example, extracellular matrix proteins, amino acids and the like, and non-biological molecules, such as, for example, polyethyleneimine.

"β-cell lineage" refers to cells with positive gene expression for the transcription factor PDX-1 and at least one of the following transcription factors: NGN-3, NRx2.2, NRx6.1, NeuroD, Isl-1, HNF-3 beta, MAFA, Pax4, and Pax6. Cells expressing markers characteristic of the β cell lineage include β cells.

"Cells expressing markers characteristic of the definitive endoderm lineage" as used herein refers to cells expressing at least one of the following markers: SOX-17, GATA-4, HNF-3 beta, GSC, Cerl, Nodal, FGF-8, Brachyury, Mix-like homeobox protein, FGF-4 CD48, eomesodermin (EOMES), DKK4, FGF-17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage" as used herein refers to cells expressing at least one of the following markers: PDX-1, HNF-1beta, PTF-1 alpha, HNF-6, or HB9. Cells expressing markers characteristic of the pancreatic endoderm lineage include pancreatic endoderm cells.

"Cells expressing markers characteristic of the pancreatic endocrine lineage" as used herein refers to cells expressing at least one of the following markers: NGN-3, NeuroD, Islet-1, PDX-1, NKX6.1, Pax-4, Ngn-3, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm" as used herein refers to cells which bear the characteristics of cells arising from the epiblast during gastrulation and which form the gastrointestinal tract and its derivatives. Definitive endoderm cells express the following markers: CXCR4, HNF-3 beta, GATA-4, SOX-17, Cerberus, OTX2, goosecoid, c-Kit, CD99, and Mix11.

"Extracellular matrix proteins" refers to proteinaceous molecules normally found between cells in the body or in the placenta. Extracellular matrix proteins can be derived from tissue, body fluids, such as, for example, blood, or media conditioned by non-recombinant cells or recombinant cells or bacteria.

"Extraembryonic endoderm" as used herein refers to a population of cells expressing at least one of the following markers: SOX-7, AFP, and SPARC.

"HEK293 cells" refers to a cell line generated by transformation of a culture of normal human embryonic kidney cells as described by Graham et al. (J. Gen. Virol. 36:59-72, 1977), and any cells derived from this parent cell line.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Matrix" as used herein refers to a 3-dimensional support to which cells may attach.

"Mesendoderm cell" as used herein refers to a cell expressing at least one of the following markers: CD48, eomesodermin (EOMES), SOX-17, DKK4, HNF-3 beta, GSC, FGF-17, GATA-6.

"Pancreatic endocrine cell" or "pancreatic hormone expressing cell" as used herein refers to a cell capable of expressing at least one of the following hormones: insulin, glucagon, somatostatin, and pancreatic polypeptide.

"Pancreatic hormone secreting cell" as used herein refers to a cell capable of secreting at least one of the following hormones: insulin, glucagon, somatostatin, and pancreatic polypeptide.

"Pre-primitive streak cell" as used herein refers to a cell expressing at least one of the following markers: Nodal, or FGF-8.

"Primitive streak cell" as used herein refers to a cell expressing at least one of the following markers: Brachyury, Mix-like homeobox protein, or FGF-4.

"Surface" as used herein refers to the outermost layer of molecules of a solid substrate vessel or matrix intended for use in cell culture or analysis. The elemental composition, the roughness, and the wettability of the surface can be analyzed by X-Ray Photoelectron Spectroscopy (XPS), Atomic Force Microscopy (AFM), and contact angle measurement, respectively.

"Surface modified plate" refers to a vessel containing any one of surfaces 1-34, described in Examples 16, 17 and 26, or plates containing surfaces that are sold under the trade names Nunclon Delta™, Costar™, Falcon™, CellBIND™, and Primaria™. The vessel can, for example, be made of a polymer, such as polystyrene (PS), cyclic olefin copolymer (COC), polycarbonate (PC), polymethyl methacrylate (PMMA), or styrene acrylonitrile copolymer (SAN).

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (i) totipotent, meaning able to give rise to all embryonic and extraembryonic cell types; (ii) pluripotent, meaning able to give rise to all embryonic cell types; (iii) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (iv) oligopotent, meaning able to give rise to a more restricted subset of cell lineages than multipotent stem cells; and (v) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. Dedifferentiation refers to the process by which a cell reverts to a less specialized (or committed) position within the lineage of a cell. As used herein, the lineage of a cell defines the heredity of the cell, that is, which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

Various terms are used to describe cells in culture. "Maintenance" refers generally to cells placed in a growth medium under conditions that facilitate cell growth and/or division that may or may not result in a larger population of the cells. "Passaging" refers to the process of removing the cells from one culture vessel and placing them in a second culture vessel under conditions that facilitate cell growth and/or division.

A specific population of cells, or a cell line, is sometimes referred to or characterized by the number of times it has been passaged. For example, a cultured cell population that has been passaged ten times may be referred to as a P10 culture. The primary culture, that is, the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (that is, the number of population doublings) during the period between passaging depends on many factors, including but not limited to the seeding density, substrate, medium, growth conditions, and time between passaging.

In one embodiment, the present invention provides a method to enhance the attachment of cells to a surface containing from at least about 0.9% N, a sum of O and N of greater than or equal to 22.3% and a contact angle of at least about 13.9 degrees, lacking a feeder cell layer and lacking an adlayer, comprising the steps of:
a. Obtaining a suspension of cells, and
b. Adding the suspension of cells to the surface and allowing the cells to attach.

In one embodiment, the present invention provides a method to enhance the attachment of cells to a surface containing from at least about 0.5% N, a sum of O and N of greater than or equal to 17.2% and a contact angle of at least about 13.9 degrees, lacking a feeder cell layer and lacking an adlayer, comprising the steps of:
a. Obtaining a suspension of cells,
b. Treating the suspension of cells with at least one compound selected from the group consisting of: a compound capable of inhibiting Rho kinase activity, and a compound capable of inhibiting Rho activity, and
c. Adding the suspension of cells to the surface and allowing the cells to attach.

In one embodiment the suspension of cells is a suspension of clusters of cells. In an alternate embodiment, the suspension of cells is a suspension of single cells.

In one embodiment, the cells are pluripotent stem cells. In an alternate embodiment, the cells are stem cells.

In one embodiment, the surface has an adlayer. In one embodiment, the adlayer is an extracellular matrix component, such as, for example, those derived from basement membrane or that may form part of adhesion molecule receptor-ligand couplings. In one embodiment, the adlayer is made from MATRIGEL (Becton Dickenson). MATRIGEL is a soluble preparation from Engelbreth-Holm Swarm tumor cells that gels at room temperature to form a reconstituted basement membrane. The proteinaceous adlayer may also be formed from laminin, fibronectin, proteoglycan, entactin, heparan sulfate, and the like, alone or in various combinations.

In one embodiment, the cells are maintained in culture after the cells attach to the surface. In an alternate embodiment the at least one compound is removed after the cells attach to the surface. In one embodiment, the cells are detached from the surface by removing the at least one compound.

In one embodiment, the suspension of cells is treated with at least one compound capable of inhibiting Rho kinase activity. In an alternate embodiment, the suspension of cells is treated with at least one compound capable of inhibiting Rho activity. In an alternate embodiment, the suspension of cells is treated with at least one compound capable of inhibiting Rho kinase activity and at least one compound capable of inhibiting Rho activity.

The at least one compound capable of inhibiting Rho kinase activity is selected from the group consisting of: Y-27632, Fasudil, and Hydroxyfasudil.

In one embodiment, the at least compound capable of inhibiting Rho kinase activity is Y-27632.

The at least one compound capable of inhibiting Rho kinase activity may be used at a concentration from about 0.1 µM to about 100 µM. In one embodiment, the at least one compound capable of inhibiting Rho kinase activity is used at a concentration of about 10 µM.

In one embodiment, the at least one compound capable of inhibiting Rho activity is a Rho GTPase inhibitor.

In one embodiment, the at least one compound capable of inhibiting Rho activity is exoenzyme C3 Transferase.

The at least one compound capable of inhibiting Rho activity may be used at a concentration from about 0.01 µg/ml to about 5 µg/ml. In one embodiment, the at least one compound capable of inhibiting Rho activity is used at a concentration of about 0.5 µg/ml.

Surface Modified Plates

Surface modified plates suitable for use in the present invention may be vessels whose surfaces have been modified to contain from at least about 0.5% N, a sum of O and N of greater than or equal to 17.2% and a contact angle of at least about 13.9 degrees. Alternatively, the surface may be a 3-dimensional matrix, such as, for example, a porous scaffold, to which cells can attach.

In one embodiment, the surface modified plate comprises a plate whose surface contains from at least about 0.5% N, a sum of O and N of greater than or equal to 17.2% and a contact angle of at least about 13.9 degrees. In an alternate embodiment, the surface modified plate comprises a plate whose surface contains from at least about 0.5% N, a sum of O and N of greater than or equal to 19.5% and a contact angle of at least about 13.9 degrees.

In one embodiment, the surface modified plate comprises a plate whose surface contains from at least about 1.3% N, a sum of O and N of at least about 24.9% and a contact angle of at least about 20.7 degrees, which is referred herein as surface modified plate 1.

In one embodiment, the surface modified plate comprises a plate whose surface contains from at least about 1.7% N, a sum of O and N of at least about 29.6% and a contact angle of at least about 14.3 degrees, which is referred herein as surface modified plate 2.

In one embodiment, the surface modified plate comprises a plate whose surface contains from at least about 2.0% N, a sum of O and N of at least about 30.7% and a contact angle of at least about 18.4 degrees, which is referred herein as surface modified plate 3.

In one embodiment, the surface modified plate comprises a plate whose surface contains from at least about 2.1% N, a sum of O and N of at least about 30.2% and a contact angle of at least about 17.4 degrees, which is referred herein as surface modified plate 4.

In one embodiment, the surface modified plate comprises a plate whose surface contains from at least about 1.8% N, a sum of O and N of at least about 28.2% and a contact angle of at least about 18.8 degrees, which is referred herein as surface modified plate 13.

In one embodiment, the surface modified plate comprises a plate whose surface contains from at least about 1.0% N, a sum of O and N of at least about 27.8% and a contact angle of at least about 44.3 degrees, which is sold under the trade name CELLBIND.

In one embodiment, the surface modified plate comprises a plate whose surface contains from at least about 10.2% N, a sum of O and N of at least about 23.0% and a contact angle of at least about 39.5 degrees, which is sold under the trade name PRIMARIA.

Characterization of the Surface Modified Plates

In one embodiment, the elemental composition of the surface of the surface modified plates may be analyzed by X-Ray Photoelectron Spectroscopy (XPS). XPS, also known as Electron Spectroscopy for Chemical Analysis (ESCA), is used as a method to determine what elements or atoms are present in the surface of a solid substrate (all elements in concentrations less than 0.1 atomic percent can be detected, except hydrogen and helium), and to determine the bonding environment of such elements or atoms. As an example, an XPS analysis of a polystyrene (contains only carbon and hydrogen) solid sample would typically give greater than 97% carbon, less than 3% oxygen, and 0% nitrogen (hydrogen is not detected; different levels of oxygen may be detected due to oxidation of the polystyrene chains at the surface, for example, as a result of sterilization by irradiation) (Brevig et al., Biomaterials 26:3039-3053, 2005; Shen and Horbett, J. Biomed. Mater. Res. 57:336-345, 2001).

In one embodiment, the roughness of the surface of the surface modified plates may be analyzed by Atomic Force Microscopy (AFM). Surface atoms or molecules with a lateral resolution down to 1Å and a vertical resolution down to 0.1 Å can be imaged by AFM.

In one embodiment, the wettability of the surface of the surface modified plates may be analyzed by measuring the contact angle. For example, contact angle measurement by the static sessile drop method provides information on the interaction between the surface of a solid substrate and a liquid. The contact angle describes the shape of a liquid drop resting on the surface of the solid substrate, and is the angle of contact of the liquid on the surface of the solid substrate, measured within the liquid at the contact line where liquid, solid, and gas meet. A surface with a water contact angle larger than 90° is termed hydrophobic, and a surface with water contact angle less than 90° is termed hydrophilic. On extremely hydrophilic surfaces, that is, surfaces that have a high affinity for water, a water droplet will completely spread (an effective contact angle of 0°).

In one embodiment, the negative charge density of the surface of the surface modified plates may be analyzed by measuring the reactivity of the surface with crystal violet. Crystal violet carries a positive charge, which enables it to bind to negatively charged molecules and parts of molecules, for example, negatively charged functional groups present on a polymer surface. A surface with a high crystal violet reactivity has a higher density of negative charges than a surface with a low crystal violet reactivity, given that the surfaces have the same roughness and thus area.

Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde and then developing with Vector Red as a substrate, as described by the manufacturer (Vector Laboratories, Burlingame Calif.). Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation.

Non-limiting examples are established lines of human ES cells or human embryonic germ cells, such as, for example the human ES cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells, as well as a pluripotent stem cell population already cultured in the presence of feeder cells. Also suitable are mutant human ES cell lines, such as, for example, BG01v (BresaGen, Athens, Ga.). Also suitable are cells derived from adult human somatic cells, such as, for examples, cells disclosed in Takahashi et al, Cell 131: 1-12 (2007).

In one embodiment, human ES cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are cultured on a layer of feeder cells or extracellular matrix protein that support the pluripotent stem cells in various ways, prior to culturing according to the methods of the present invention. For example, pluripotent stem cells are cultured on a feeder cell layer that supports proliferation of pluripotent stem cells without undergoing substantial differentiation. The growth of pluripotent stem cells on a feeder cell layer without differentiation is supported using (i) Obtaining a culture vessel containing a feeder cell layer; and (ii) a medium conditioned by culturing previously with another cell type, or a non-conditioned medium, for example, free of serum or even chemically defined.

In another example, pluripotent stem cells are cultured in a culture system that is essentially free of feeder cells, but nonetheless supports proliferation of pluripotent stem cells without undergoing substantial differentiation. The growth of pluripotent stem cells in feeder-cell free culture without differentiation is supported using (i) an adlayer on a solid substrate surface with one or more extracellular matrix proteins; and (ii) a medium conditioned by culturing previously with another cell type, or a non-conditioned medium, for example, free of serum or even chemically defined.

In an alternate embodiment, pluripotent stem cells are cultured on a surface modified plate containing from at least about 0.5% N, a sum of O and N of greater than or equal to 17.2% and a contact angle of at least about 13.9 degrees in a medium conditioned by culturing previously with another cell type, or a non-conditioned medium, for example, free of serum or even chemically defined.

Culture medium: An example of cell culture medium suitable for use in the present invention may be found in US20020072117. Another example of cell culture medium suitable for use in the present invention may be found in U.S. Pat. No. 6,642,048. Another example of cell culture medium suitable for use in the present invention may be found in WO2005014799. Another example of cell culture medium suitable for use in the present invention may be found in Xu et al (Stem Cells 22: 972-980, 2004). Another example of cell culture medium suitable for use in the present invention may be found in US20070010011. Another example of cell culture medium suitable for use in the present invention may be found in Cheon et al. (BioReprod DOI: 10.1095/biolreprod.105.046870; 19 Oct. 2005). Another example of cell culture medium suitable for use in the present invention may be found in Levenstein et al. (Stem Cells 24: 568-574, 2006). Another example of cell culture medium suitable for use in the present invention may be found in US20050148070. Another example of cell culture medium suitable for use in the present invention may be found in US20050233446. Another example of cell culture medium suitable for use in the present invention may be found in U.S. Pat. No. 6,800,480. Another example of cell culture medium suitable for use in the present invention may be found in US20050244962. Another example of cell culture medium suitable for use in the present invention may be found in WO2005065354. Another example of cell culture medium suitable for use in the present invention may be found in WO2005086845.

Suitable culture media may also be made from the following components, such as, for example, Dulbecco's modified Eagle's medium (DMEM), Gibco # 11965-092; Knockout Dulbecco's modified Eagle's medium (KO DMEM), Gibco # 10829-018; Ham's F12/50% DMEM basal medium; 200 mM L-glutamine, Gibco # 15039-027; non-essential amino acid solution, Gibco 11140-050; β-mercaptoethanol, Sigma # M7522; human recombinant basic fibroblast growth factor (bFGF), Gibco # 13256-029.

Differentiation of Pluripotent Stem Cells

In one embodiment of the present invention, pluripotent stem cells are propagated in culture, while maintaining their pluripotency. Changes in pluripotency of the cells with time can be determined by detecting changes in the levels of expression of markers associated with pluripotency. Alternatively, changes in pluripotency can be monitored by detecting changes in the levels of expression of markers associated with differentiation or markers associated with another cell type.

In an alternate embodiment, pluripotent stem cells are propagated in culture and then treated in a manner that promotes their differentiation into another cell type. The other cell type may be a cell expressing markers characteristic of the definitive endoderm lineage. Alternatively, the cell type may be a cell expressing markers characteristic of the pancreatic endoderm lineage. Alternatively, the cell type may be a cell expressing markers characteristic of the pancreatic endocrine lineage. Alternatively, the cell type may be a cell expressing markers characteristic of the β-cell lineage.

Pluripotent stem cells treated in accordance with the methods of the present invention may be differentiated into a variety of other cell types by any suitable method in the art.

For example, pluripotent stem cells treated in accordance with the methods of the present invention may be differentiated into neural cells, cardiac cells, hepatocytes, and the like.

For example, pluripotent stem cells treated in accordance with the methods of the present invention may be differentiated into neural progenitors and cardiomyocytes according to the methods disclosed in WO2007030870.

In another example, pluripotent stem cells treated in accordance with the methods of the present invention may be differentiated into hepatocytes according to the methods disclosed in U.S. Pat. No. 6,458,589.

For example, pluripotent stem cells may be differentiated into cells expressing markers characteristic of the definitive endoderm lineage according to the methods disclosed in D'Amour et al., Nature Biotechnol. 23:1534-1541, 2005.

For example, pluripotent stem cells may be differentiated into cells expressing markers characteristic of the definitive endoderm lineage according to the methods disclosed in Shinozaki et al., Development 131:1651-1662, 2004.

For example, pluripotent stem cells may be differentiated into cells expressing markers characteristic of the definitive endoderm lineage according to the methods disclosed in McLean et al., Stem Cells 25:29-38, 2007.

For example, pluripotent stem cells may be differentiated into cells expressing markers characteristic of the definitive endoderm lineage according to the methods disclosed in D'Amour et al., Nature Biotechnol. 24:1392-1401, 2006.

Markers characteristic of the definitive endoderm lineage are selected from the group consisting of SOX17, GATA4, Hnf-3beta, GSC, Cerl, Nodal, FGF-8, Brachyury, Mix-like homeobox protein, FGF-4 CD48, eomesodermin (EOMES), DKK4, FGF-17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

For example, pluripotent stem cells may be differentiated into cells expressing markers characteristic of the pancreatic endoderm lineage according to the methods disclosed in D'Amour et al., Nature Biotechnol. 24:1392-1401, 2006.

Markers characteristic of the pancreatic endoderm lineage are selected from the group consisting of Pdx1, HNF-1beta, PTF1a, HNF-6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Pluripotent stem cells may be differentiated into cells expressing markers characteristic of the pancreatic endocrine lineage by any method in the art.

For example, pluripotent stem cells may be differentiated into cells expressing markers characteristic of the pancreatic endocrine lineage according to the methods disclosed in D'Amour et al., Nature Biotechnol. 24:1392-1401, 2006.

For example, pluripotent stem cells may be differentiated into cells expressing markers characteristic of the pancreatic endocrine lineage, by the methods disclosed in D'Amour et al., Nature Biotechnol. 24:1392-1401, 2006.

Markers characteristic of the pancreatic endocrine lineage are selected from the group consisting of NGN-3, NeuroD, Islet-1, Pdx-1, NKX6.1, Pax-4, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the P cell lineage. A cell expressing markers characteristic of the P cell lineage expresses Pdx1 and at least one of the following transcription factors: NGN-3, NRx2.2, NRx6.1, NeuroD, Isl-1, HNF-3 beta, MAFA, Pax4, and Pax6. In one aspect of the present invention, a cell expressing markers characteristic of the P cell lineage is a P cell.

The present invention is further illustrated, but not limited by, the following examples.

EXAMPLES

Example 1

Passage and Maintenance of Human Embryonic Stem Cells as Cell Clusters

The human ES cell lines H1 and H9 were initially maintained on mitomycin C inactivated primary mouse embryonic fibroblasts (MEF). The human ES cells were switched from MEF feeders to Matrigel™ (Becton-Dickinson, Bedford, Mass.) over repeated passages.

Treatment of surfaces with Matrigel™: Growth Factor Reduced Matrigel™ was thawed at 4° C. and then diluted 1:30 in cold DMEM/F12 (Invitrogen, Carlsbad, Calif.). Volumes sufficient to cover the surface were added to each 6-cm dish (2 ml) or each well of a 6-well plate (1 ml), and incubated 1 hr at room temp. Treated surfaces were used within a few hours or stored at 4° C. up to two weeks.

Human ES cell culture: Undifferentiated human ES cell colonies (from either the H9 or H1 lines) were harvested from feeder layers by incubation in 1 mg/ml collagenase IV (Sigma-Aldrich, St. Louis, Mo.) in DMEM/F12 for 10 minutes, followed by scraping with a pipette. Cell clumps were pelleted by centrifugation at 600×g for four minutes and the pellet dispersed gently with a 2-ml pipette to break colonies into small clusters of cells. These cell clusters were seeded onto Matrigel™-treated dishes in media conditioned with mouse embryonic fibroblasts (MEF-CM), further supplemented with bFGF (8 ng/ml; R&D Systems, Minneapolis, Minn.), at 50-150 colonies per 6-cm dish in 5 ml growth medium. Medium was changed daily. Colonies on Matrigel™ in MEF-CM became large and were passed when they occupied 70-80% of the surface area, approximately every 3-4 days. The human ES cells in the colonies had a high nucleus to cytoplasm ratio and had prominent nucleoli, similar to human ES cells maintained on feeders (FIG. 1). Differentiated cells represented less than 5% of total cells in culture.

For routine passage of cells in MEF-CM on Matrigel™, cells were incubated in 1 mg/ml collagenase IV in DMEM/F12 for up to 60 minutes and removed from the dishes by forceful streams of DMEM/F12 with scraping. Cells were pelleted, dispersed, and seeded at a 1:3 or 1:4 ratio.

Example 2

Passage of Human Embryonic Stem Cells as Single Cells

Human ES cells of the cell line H9 were grown as single cells according to the methods disclosed in US Patent Application LFS5163USPSP, assigned to LifeScan Inc. Cells were passaged by treatment with TrypLE™ Express for five minutes at 37° C., and seeded at 10,000 cells/cm$^2$ substrate surface.

Example 3

Attachment, Cultivation and Maintenance of Pluripotency of Human Embryonic Stem Cells Using Surface Modified Plates Lacking Extracellular Matrix Protein/Components and Feeder Cells Human ES cells of the line H1, at passage 49 were maintained in MEF conditioned media on Nunclon Delta™ plates treated with a 1:30 dilution of growth factor reduced Matrigel™, prior to study. Cells were dissociated from the surface for passage by 1 mg/ml collagenase dissociation or by manual scraping.

These cells were then seeded onto two untreated wells of the surface modified plates (6-well format). Additionally, one well of each plate was treated with 0.1% xeno-free human gelatin as a control. Cells were also plated directly onto untreated and gelatin-treated wells of Costar™ (cat. no. 3516; Corning, Corning, N.Y.), Falcon™ (cat. no. 351146; Becton Dickinson, Franklin Lakes, N.J.) and Nunclon Delta™ (cat. no. 140675; Thermo Fisher Scientific, Roskilde, Denmark) 6-well plates for negative controls, and plated onto wells treated with 1:30 dilution of growth factor reduced Matrigel™ to provide as positive controls. In all treatments cells were maintained in MEF conditioned media.

After two passages, surface modified plates 2, 3, and 4 had attached ES cell colonies, which re-attached to the plates and grew following enzymatic dissociation. There was no apparent difference in rate of attachment or growth in gelatin or untreated wells from surface modified plates 2, 3, or 4.

Cells mechanically dissociated from plates treated with 1:30 dilution of growth factor reduced Matrigel™ were poorly attached to surface modified plates 2, 3, and 4, while cells enzymatically dissociated with 1 mg/ml collagenase were well attached in gelatin or untreated wells from surface modified plates 2, 3, or 4.

H1p49 ES cells added to surface modified plates 1 and 5-12 and to untreated or gelatin treated Nunclon Delta™ plates, Falcon™ plates, and Costar™ plates did not attach. The same cells did attach to plates treated with 1:30 dilution of growth factor reduced Matrigel™, indicating that the cells were competent to attach to a substrate surface.

Normal passage time for ES cells of the H1 line plated on 1:30 dilution of growth factor reduced Matrigel™ was 3-4 days, however cells plated on surface modified plates 2, 3 and 4 took 7 days of culturing before they were ready for passage. This was probably due to the reduced rate of attachment on the treated surfaces, since more starting colonies were apparent on Matrigel™-treated surfaces immediately after plating than on Surfaces 2, 3 and 4.

The passage (p) 50 Cells were split at a 1 to 2 ratio and half of the sample was collected for RNA purification and tested for expression of pluripotency markers (Table 1). The other half of each sample was replated to surface modified plates. Colonies that formed at this passage (p51) also required 7 days of culturing before they were ready to be passaged, and the small colonies that developed after only 4 days of culturing are shown in FIG. 1. These colonies maintained classical ES cell colony morphology.

Cultures were stopped at passage 4 on surface modified plates 2, 3 and 4 and samples were assayed for pluripotency markers by qRT-PCR (Table 2) and differentiated to a definitive endoderm fate (DE). Cells at passage 4 maintained expression of the classical pluripotency markers: Oct4, Nanog, Sox2, and TERT. Furthermore, the cells were able to differentiate to a definitive endoderm fate upon exposure to a media containing DMEM/F12, 100 ng/ml Activin A, 20 ng/ml Wnt3a, and 0.5-2.0% FBS (Table 3) indicating that pluripotency was maintained in the cells through passage 4.

Example 4

Attachment, Cultivation and Maintenance of Pluripotency of Human Embryonic Stem Cells on Surface Modified Plates Lacking Extracellular Matrix Protein/Components and Feeder Cells: Effects of Rho Inhibition and Rho Kinase Inhibition Human ES cells of the line H1, at passage 49 were maintained in MEF conditioned media on Nunclon Delta™ plates treated with a 1:30 dilution of growth factor reduced Matrigel™, prior to study. Cells were dissociated from the surface for passage by 1 mg/ml collagenase dissociation.

These cells were then seeded onto untreated wells of surface modified plates (6-well format). Cells were also plated directly onto untreated and gelatin-treated wells of Costar™ Falcon™, and Nunclon Delta™ 6-well plates for negative controls and plated onto wells treated with 1:30 dilution of growth factor reduced Matrigel™ to provide as positive controls. In all treatments cells were maintained in MEF conditioned media.

Human ES cells of the line H1, at passage 49 added to surface modified plates 1 and 5-12 and to untreated or gelatin treated Nunclon Delta™ plates and Costar™ plates did not attach, however, they did attach to surface modified plates 2, 3, and 4. The same cells did attach to plates treated with 1:30 dilution of growth factor reduced Matrigel™, indicating that the cells were competent to attach to a substrate surface.

Normal passage time for H1 ES cells plated on 1:30 dilution of growth factor reduced Matrigel™ was 3-4 days, however cells plated on surface modified plates 2, 3 and 4 took 7 days of culturing before they were ready for passage. This was probably due to the reduced rate of attachment on the surface modified plates, since more starting colonies were apparent on Matrigel™-treated surfaces immediately after plating than on surface modified plates 2, 3 and 4.

The passage (p) 50 Cells were split at a 1 to 2 ratio and half of the sample was collected for RNA purification and tested for expression of pluripotency markers (Table 1). The other half of each sample was replated to surface modified plates. Colonies that formed at this passage (p51) also required 7 days of culturing before they were ready to be passaged, and the small colonies that developed after only 4 days of culturing are shown in FIG. 1. These colonies maintained classical ES cell colony morphology.

Due to the delay in passage, the cells were split at a 1 to 2 ratio and half of the passage 4 samples were plated in MEF conditioned media or MEF conditioned media supplemented with the Rho kinase (ROCK) inhibitor, Y-27632, at a 10 μM concentration in an attempt to improve cell growth kinetics. Cells were kept in the plating media for 48 hours after passage at which time the media was changed to fresh unsupplemented MEF conditioned media.

Figure 2:
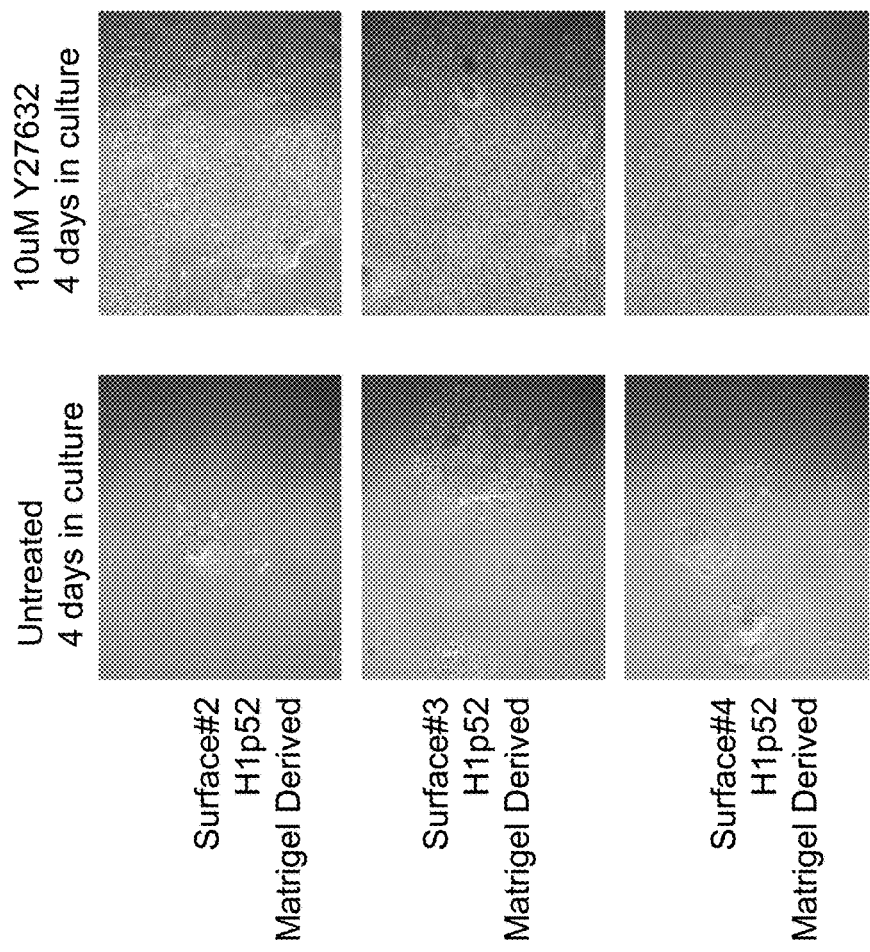
FIG. 2 shows the effect of 10 μM Y-27632 on the attachment of human ES cells to surface modified plates. The figure shows phase contrast micrographs (4×) of cells of the human ES cell line H1 that were passaged twice as clusters on surface modified plates 3 and 4. Cells were then passaged onto surface modified plates 2, 3 or 4, in MEF conditioned medium containing 10 μM Y-27632. Cells were cultured for four days prior to taking the photographs. Cells cultured in the absence of Y-27632 were included as controls.

The addition of Y-27632 at a 10M concentration significantly increased plating efficiency of the cells (p52) and the improvement in colony growth was apparent after 4 days post-plating (FIG. 2). Alternatively, prior to collagenase dissociation, human ES cells of the line H1 were also treated with 0.5 ng/ml of a cell permeable form of the Rho inhibitor, C3 exotransferase, which also increased the plating efficiency of the cells.

Figure 3:
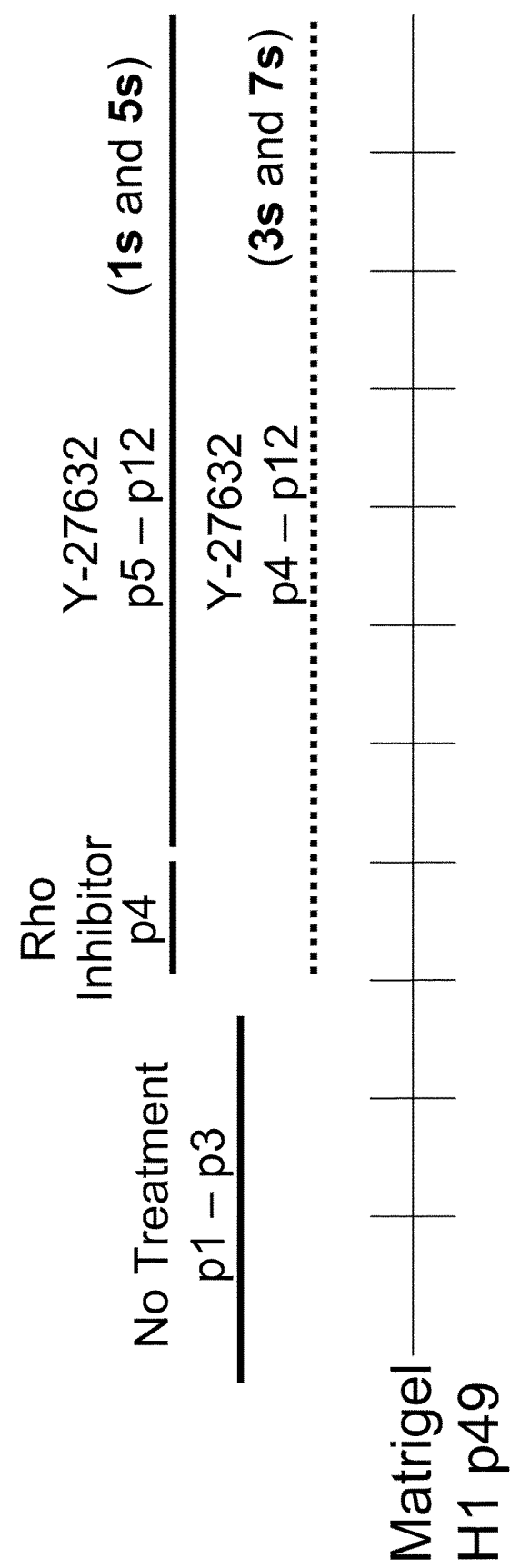
FIG. 3 shows a schematic of the time-course of treatment of compounds on human ES cells cultured on the surface modified plates of the present invention. Cells of the human ES cell line H1 were passaged four times as clusters with LIBERASE treatment on surface modified plates 3, or 4, and cultured in MEF conditioned medium. Cells were treated for the first two days after passage with either 10 μM of the Rho Kinase inhibitor, Y-27632, or with 0.5 ng/ml of the Rho inhibitor, a cell permeable form of exoenzyme C3 transferase. Cells that were treated with the Rho Kinase inhibitor, Y-27632 and were thereafter treated for the first two days after each passage with Y-27632 on surface modified plate 3 are referred to as "7s". Cells that were treated with the Rho Kinase inhibitor, Y-27632 and were thereafter treated for the first two days after each passage with Y-27632 on surface modified plate 4 are referred to as "3s". Cells that were treated with the Rho inhibitor for two days and were then treated with the Rho Kinase inhibitor, Y-27632 for two days after each passage and thereafter treated for the first two days after passage with Y-27632 on surface modified plate 3 are referred to as "5s". Cells that were treated with the Rho inhibitor for two days and were then treated with the Rho kinase inhibitor, Y-27632 for two days after each passage and thereafter treated for the first two days after passage with Y-27632 on surface modified plate 4 are referred to as "is".

While cells plated in 10 µM Y-27632 could be passaged 4 days after plating, cells plated without the ROCK inhibitor were not ready to be split 4 days after plating. Cells treated with Rho inhibitor, C3 exotransferase were also not ready for passage 4 days after plating and cells exhibited increased differentiation to a fibroblast-like morphology. Consequently, cells treated with Rho inhibitor at passage 4 were treated with Y-27632 at all subsequent passages (FIG. 3).

Figure 4:
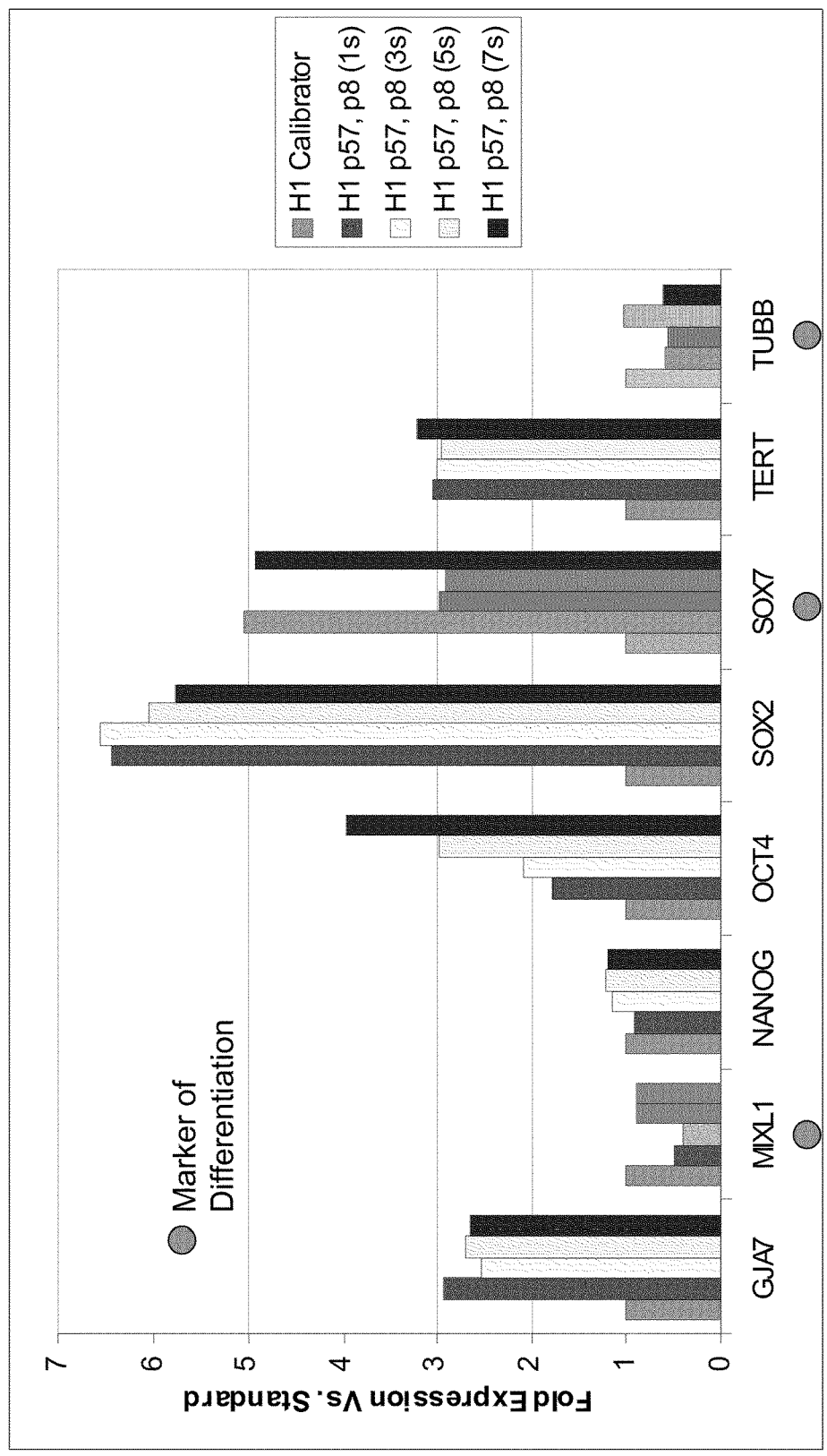
FIG. 4 shows the expression of markers associated with pluripotency and differentiation in human ES cells treated according to the protocol outlined in FIG. 6 as determined by qRT-PCR.
Figure 5:
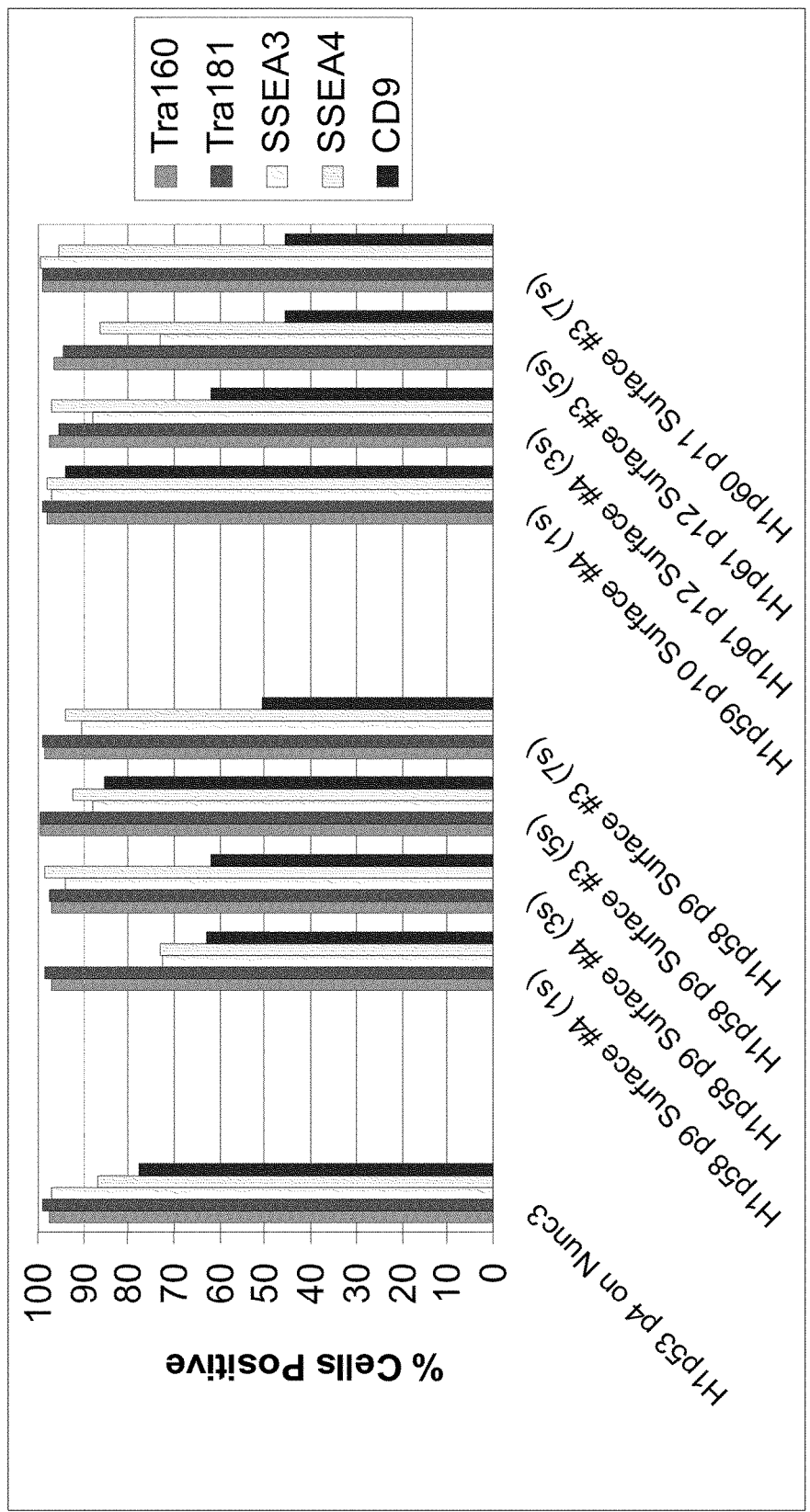
FIG. 5 shows the expression of pluripotency markers in cells of the human ES cell line H1 as determined by flow cytometry at passage 4 (p4), passage 9 (p9), and again at passage 10, 11, or 12 (p10, p11, or p12).
Figure 6:
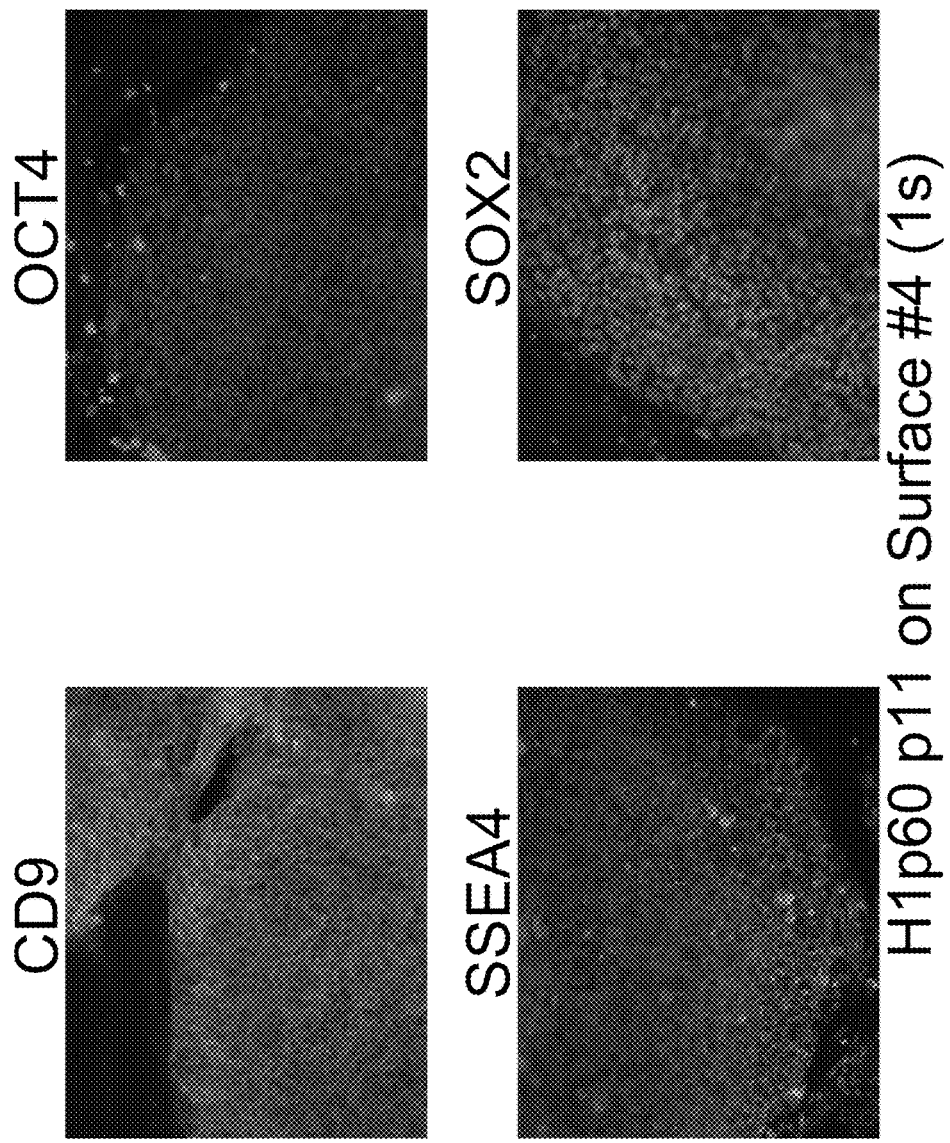
FIG. 6 shows immuno-fluorescent images of cells of the human ES cell line H1 were passaged serially as clusters with LIBERASE treatment on surface modified plate 4, and cultured in MEF conditioned medium. Expression of proteins associated with markers of pluripotency was detected in cells cultured for 11 passages on surface modified plate 4. Cells were treated with 10 μM Y-27632 for two days after each passage.
Figure 7:
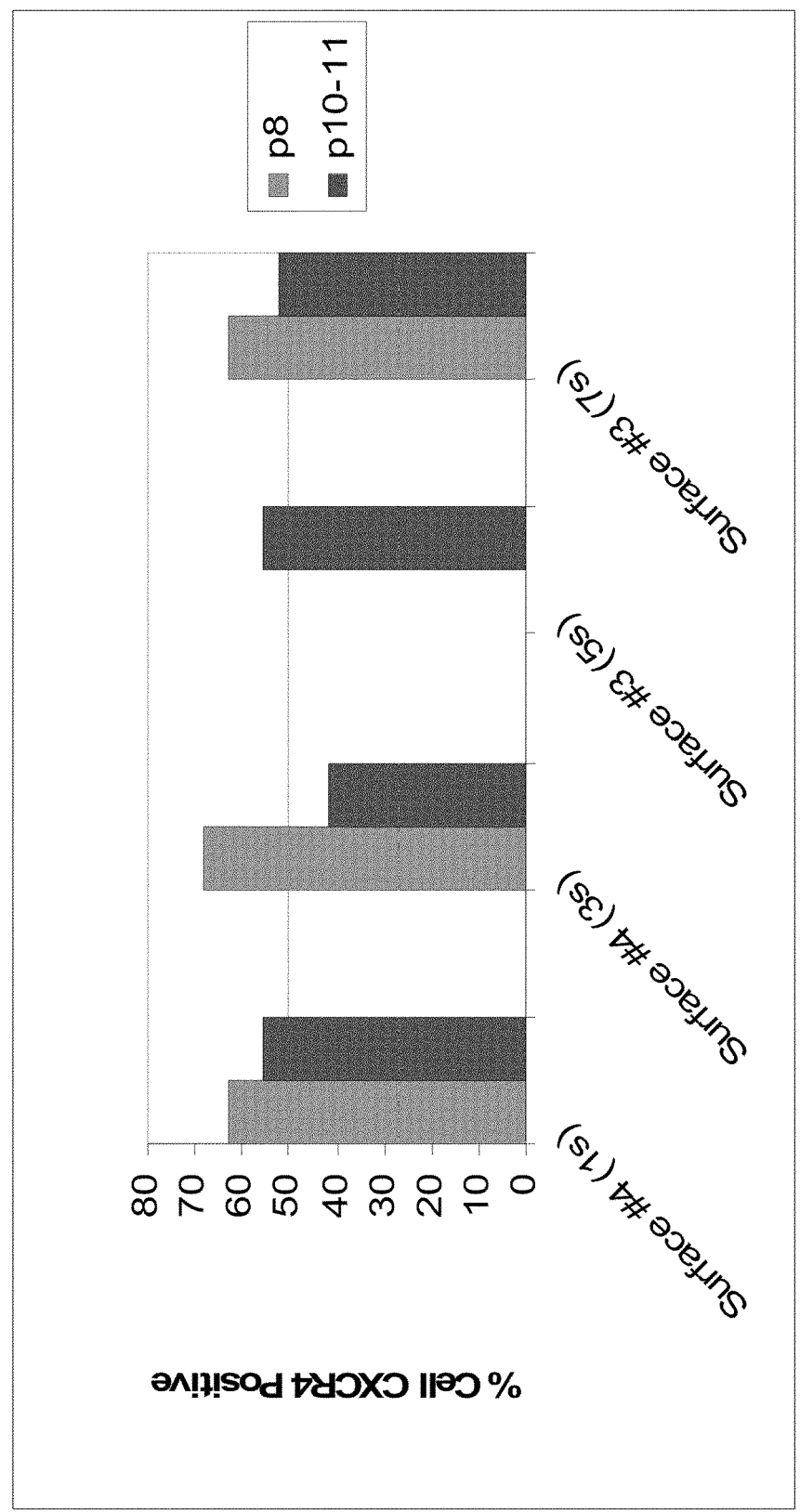
FIG. 7 shows the ability for human ES cells to form definitive endoderm after culture on surface modified plates. Cells of the human ES cell line H1 were passaged 11 times as clusters with LIBERASE treatment on surface modified plates 3, or 4 and cultured in MEF conditioned medium. At passage 8 (p8) and again at passage 10 or 11 (p10-11) cells were treated with DMEM:F12 media containing 0.5% FBS, 100 ng/ml Activin A, and 20 ng/ml Wnt3a for two days and then treated with DMEM:F12 media containing 2% FBS and 100 ng/ml Activin A for three more days. The y-axis on the graph shows the percent positive CXCR4 cells obtained by flow cytometry. See also Table 5.
Figure 8:
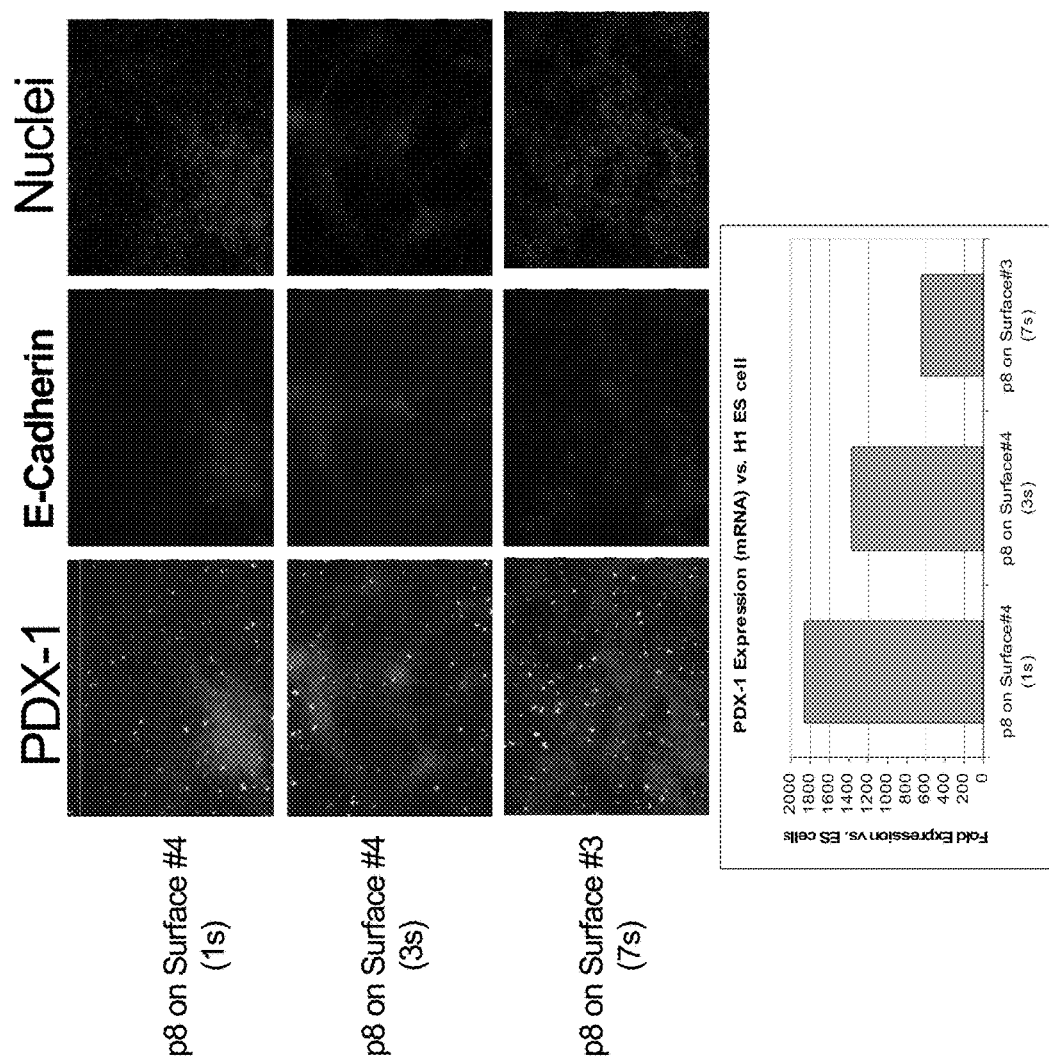
FIG. 8 shows the ability for human ES cells to form pancreatic endoderm after culture on surface modified plates. Cells of the human ES cell line H1 were passaged eight times as clusters with LIBERASE treatment on surface modified plates 3, or 4 and cultured in MEF conditioned medium. At passage 8 (p8) cells were subjected to differentiation to definitive endoderm by treatment with DMEM: F12 media containing 0.5% FBS, 100 ng/ml Activin A, and 20 ng/ml Wnt3a for two days and then treated with DMEM:F12 media containing 2% FBS and 100 ng/ml Activin A for three more days. The cells were then further differentiated to embryonic foregut with four days of treatment with DMEM:F12 media containing 2% FBS, 100 ng/ml FGF-10, and 1 µM cyclopamine-KAAD. The cells were then differentiated to pancreatic endoderm with four days of treatment with DMEM:F12 media containing 1% B-27, 100 ng/ml FGF-10, 1 µM cyclopamine-KAAD and 2 µM retinoic acid. Cells were stained by immunofluorescence for PDX-1 (green) and E-cadherin (red) and total cell number was identified by Hoechst dye (blue).

Cells were further passaged to at least 10 passages on surface modified plates 3 and 4 and were tested for the presence of markers associated with pluripotency: genes by qRT-PCR; cell surface marker expression by flow cytometry; and immunofluorescence of cell surface and nuclear proteins (FIGS. 4-6). Cellular pluripotency was also confirmed by testing their capacity to differentiate to definitive endoderm, pancreatic endoderm, and form embryoid bodies composed of the three germ layers (FIGS. 7-9). Cells were also tested for karyotypic stability, and we observed that cells could maintain a normal karyotype (FIG. 10).

Example 5

Attachment and Detachment of Human Embryonic Stem Cells Through Rho Kinase Inhibition Human ES cells of the line H9, at passage 40 were maintained in MEF conditioned media on Nunclon Delta™ plates treated with a 1:30 dilution of growth factor reduced Matrigel™ prior to study. Cells were dissociated from the surface for passage by 1 mg/ml collagenase dissociation or by manual scraping.

These cells were then seeded onto surface modified plates 2, 3, 4 and 13 (12-well format) in the presence of increasing amounts one of the following Rho Kinase inhibitors: Y-27632 (from Sigma, St. Louis, Mo. or EMD, San Diego, Calif.), Fasudil (Sigma), or Hydroxyfasudil (Sigma), and maintained for 3 days, each day replacing the media and compound. At the end of day three, media was removed and the plates were stained with Crystal Violet (0.5% in water) to visualize colonies.

Figure 11:
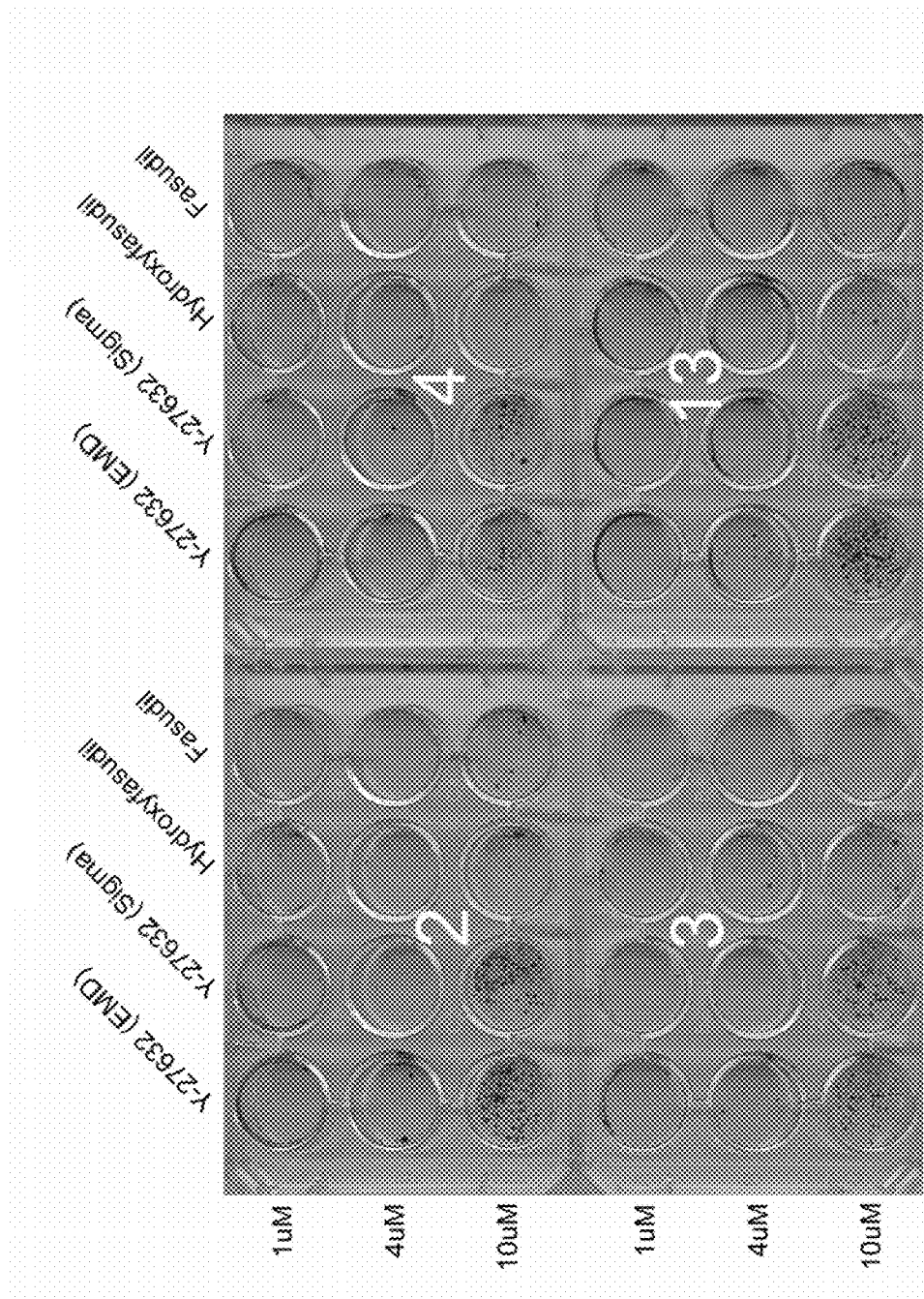
FIG. 11 shows the effect of treatment with Rho kinase inhibitors (Y-27632 from EMD biosciences, Y-27632 from Sigma, Fasudil, and Hydroxyfasudil) on the attachment of human ES cells to surface modified plates. Cells were cultured in medium containing the indicated compounds, at the concentrations listed, for three days. Cells were stained with crystal violet and images taken.

By day three, surface modified plates 2, 3, 4 and 13 had attached ES cell colonies in the presence of increasing amounts of Rho kinase inhibitor. Best results were obtained through the use of Y-27632 (10 µM), although some colonies could be observed to attach and grow with the Rho kinase inhibitors, Fasudil and Hydroxyfasudil (FIG. 11).

Figure 12:
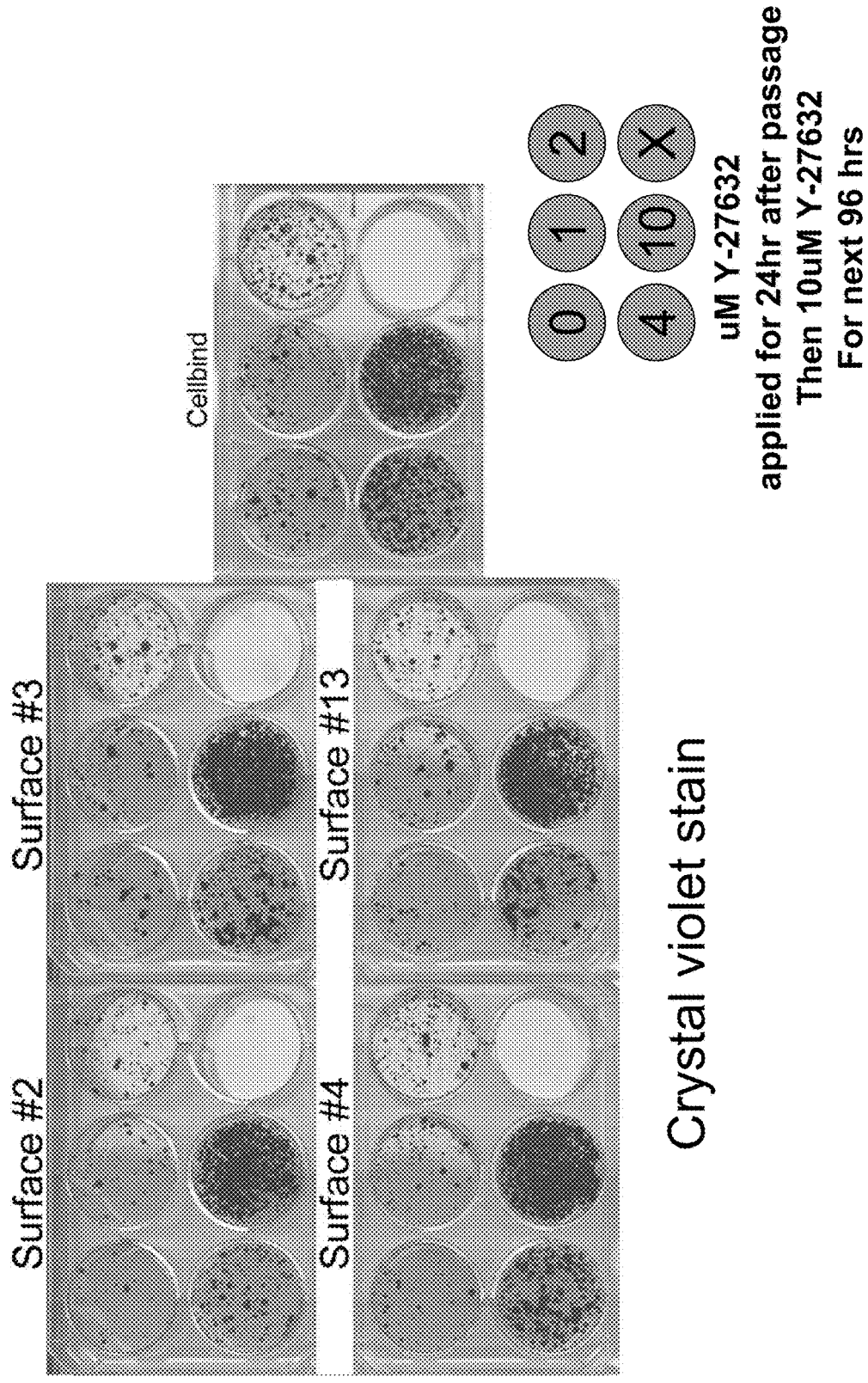
FIG. 12 shows the dose-response of Y-27632 on the attachment of human ES cells to surface modified plates. Various concentrations of the Rho kinase inhibitor, Y-27632, was added to the cultures at a specified concentration (0, 1, 2, 4, or 10 µM Y-27632) for the first day. The cells were then maintained from day 2 onward in media containing 10 µM Y-27632 with daily media changes for five days. Media was removed from the plates on day five and the cells were stained with 0.5% crystal violet, and images taken.

It was attempted to determine the optimal dose of Y-27632 to promote cell binding, by treating cells with a range of plating concentrations of Y-27632 for the first day of culture. After the first day in culture, cells were treated on subsequent days with a 10 µM concentration of Y-27632. It was observed that the maximal concentration to stimulate attachment and growth of ES cells was 10 µM (FIG. 12) and that this occurred on surface modified plates 2, 3, 4, 13 and CellBIND™ (Corning, Corning, N.Y.).

The effect of treating the cells continuously with a single dose of Y-27632 on attachment and growth was also tested. The cells were dosed with 0, 1, 4, or 10 µM Y-27632 for 4 days. Some binding was observed on surface modified plates without treatment (0 µM), however the optimal concentration to stimulate attachment and growth of ES cells was 10 µM Y-27632 (Table 4) on surface modified plates 2, 3, 4, 13.

Figure 13:
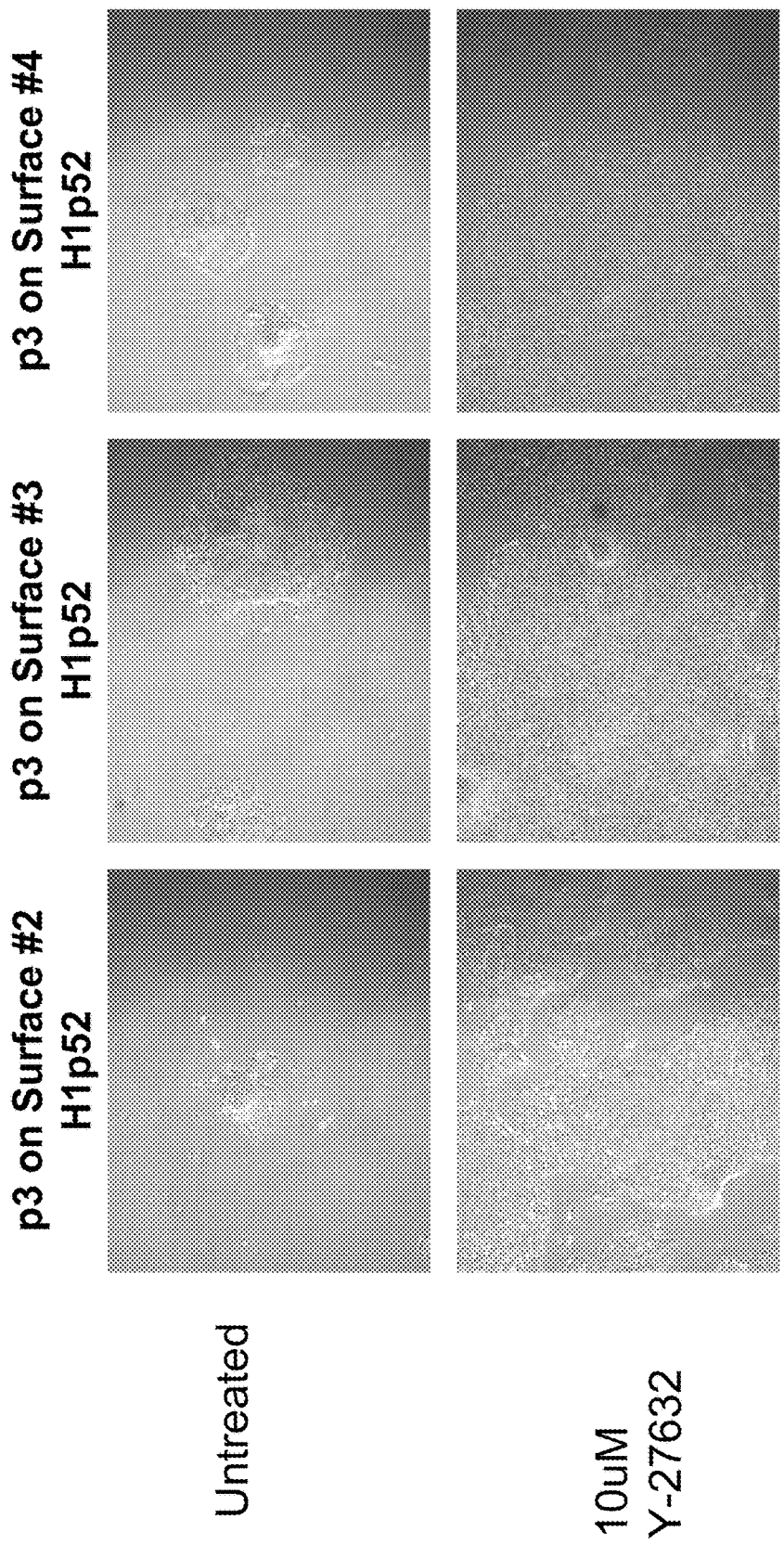
FIG. 13 shows the formation of human ES cell colonies four days after passage onto surface modified plates 2, 3, or 4 with or without 10 of µM Y-27632.
Figure 14:
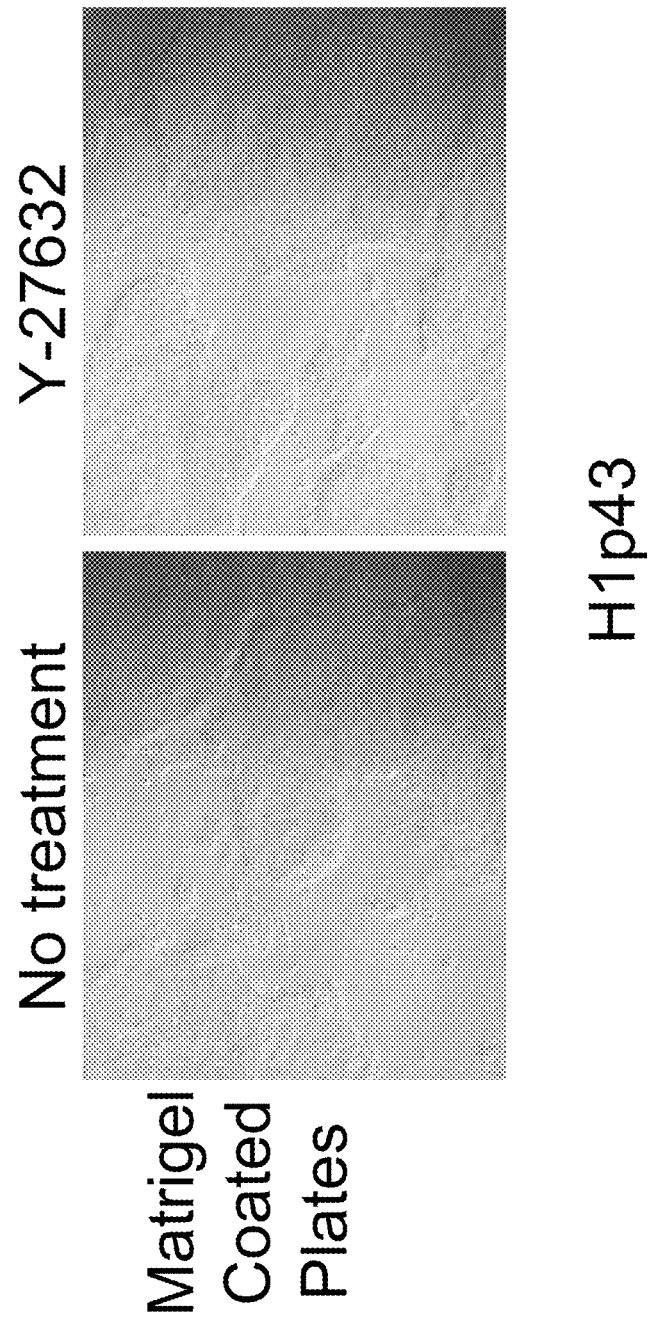
FIG. 14 shows the formation of human ES cell colonies four days after passage onto Matrigel™ treated plates with or without 10 µM Y-27632.
Figure 15:
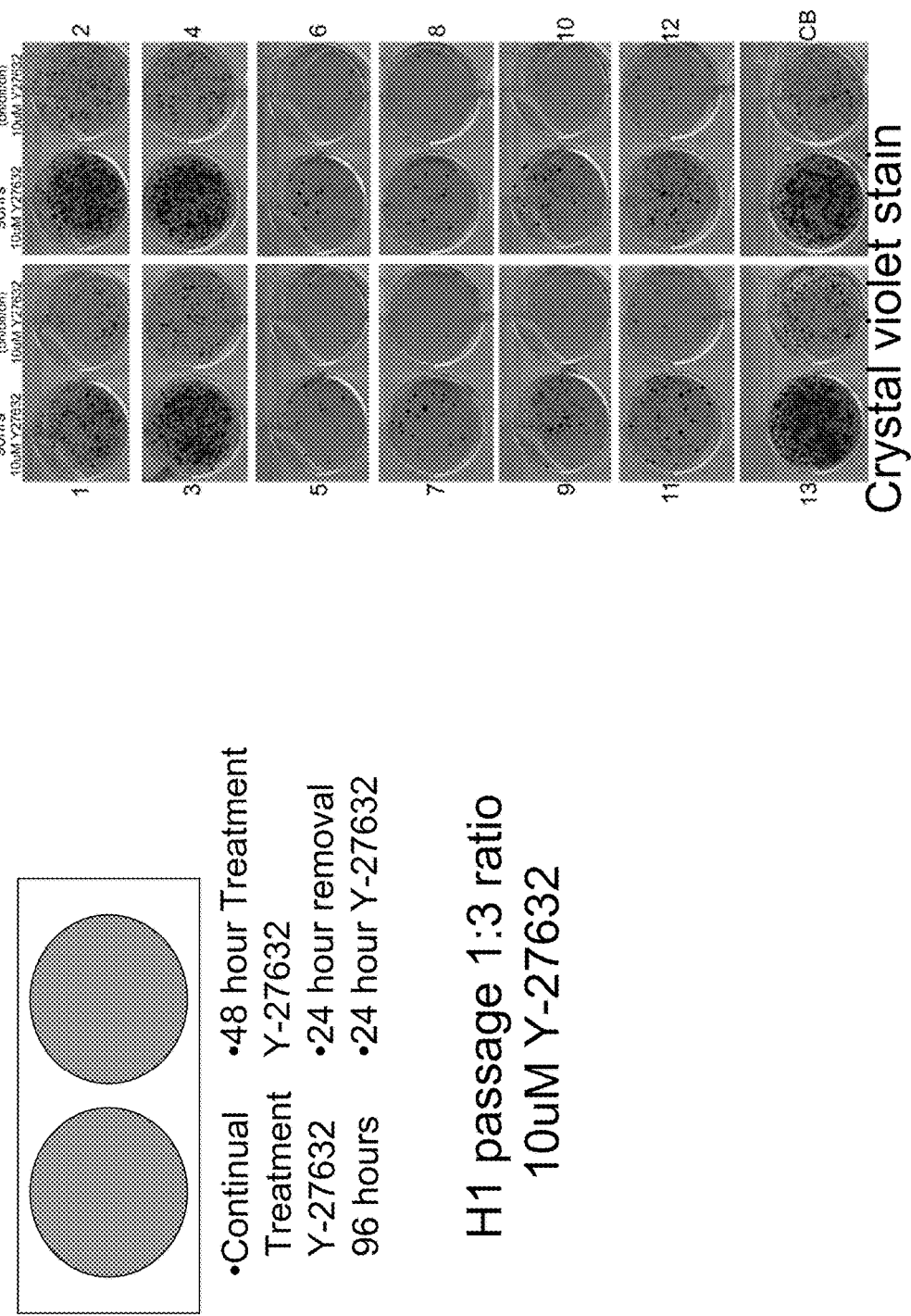
FIG. 15 shows the difference between continual and intermittent treatment of human ES cells with Y-27632, on attachment of cells to surface modified plates.

Since the addition of ROCK inhibitor significantly enhances the plating and growth kinetics on surface modified plates 2, 3, and 4 versus untreated cells (FIG. 13), we wished to determine if this was due to maintenance of proper cell attachment or due to increased cell proliferation. It was observed that Rho Kinase inhibition does not increase cell proliferation, because cells treated with Y-27632 grow at a similar density as untreated cells (FIG. 14). Instead, Y-27632 treatment maintains the attachment of cells to the surface and allows them to grow with normal proliferation kinetics (FIG. 15). Removal of a Rho Kinase inhibitor from the growth media of ES cells plated in the presence of Rho kinase inhibitor results in detachment of the cells from the surface. The formation of embryoid bodies with differentiation to the 3 germ lineages is accomplished by culturing ES cells in a suspension. Consequently, although later reapplication of a Rho kinase inhibitor restored attachment of cells (FIG. 15), as expected, substantial differentiation of the ES cell culture was observed in samples where Rho kinase inhibitor was withdrawn for 24 hours of culture and cells were allowed to detach, grow in suspension for 24 hours and Rho kinase inhibitor was then reapplied.

Example 6

H9 human ES cells passaged with TrypLE™ Express on Surface Modified Plates Show Improved Adhesion with Y-27632

Figure 16:
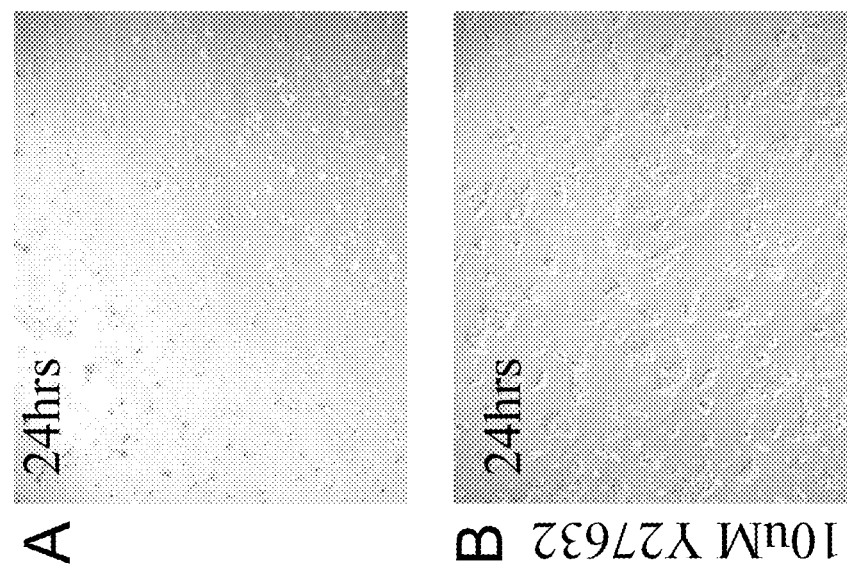
FIG. 16 depicts images of cells from the human ES cell line H9, that were passaged as single cells, seeded on to surface modified plate 3 in MEF conditioned media containing (B) or with out (A) 10 µM Y-27632. The images were taken 24 hours after seeding.

Initial passaging of H9 human ES cells onto surface modified plates. Adhesion is improved with continuous 10 µM of Y-27632. This is true for the four surface modified plates tested: 2, 3, 4 and 13. Images of H9 cells 24 hours after seeding on Surface 3 are shown in FIG. 16.

Example 7

Figure 17:
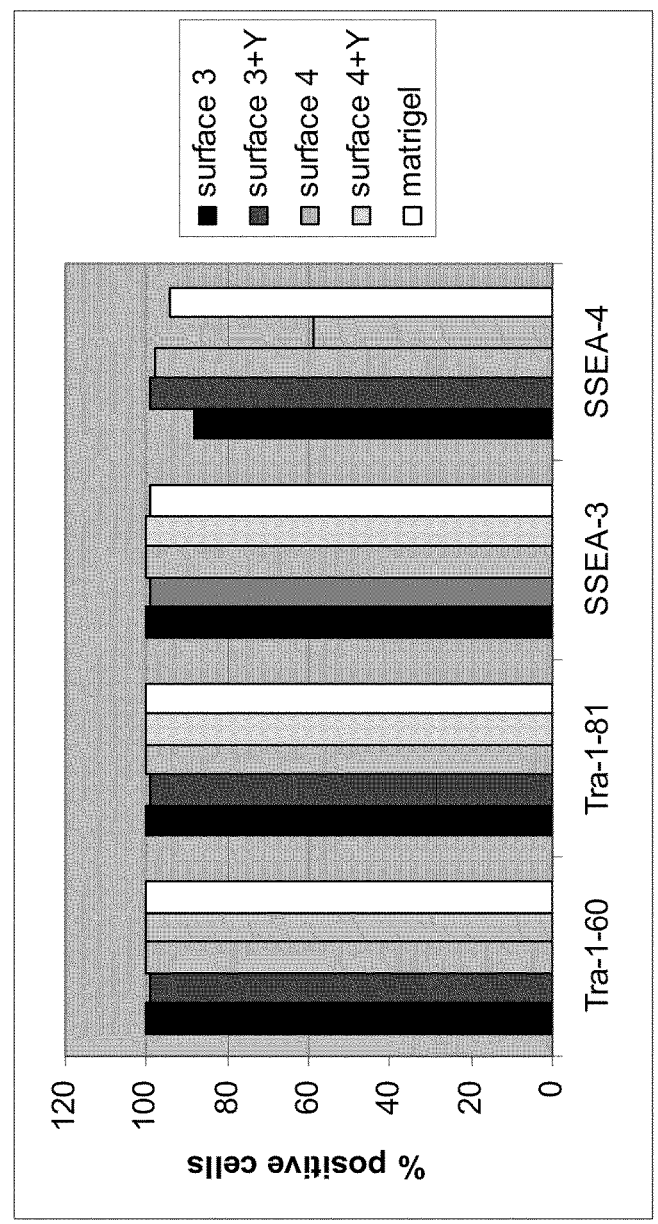
FIG. 17 depicts the expression of markers associated with pluripotency in cells from the human ES cell line H9, that were passaged as single cells for 5 passages, using TrypLE™ Express, and plated onto surface modified plates 3 and 4, with or with out 10 µM of Y-27632 (Y). The pluripotency markers are listed on the x-axis and the percentage of positive cells is shown on the y-axis.

H9 single Human Embryonic Stem Cells Passaged with TrypLE™ Express on Surface Modified Plates Remain Pluripotent Human ES cells are pluripotent and have the ability to differentiate into all cell lineages. The pluripotent state of the cells must be maintained by the surface on which they grow. To determine if the surface modified plates can maintain human ES cell pluripotency, the human ES cells were passaged 38 times with collagenase and 38 times with TrypLE™ Express followed by 5 passages on surface modified plate 3 (Surface 3), surface modified plate 4 (Surface 4) or Matrigel™ at 1:30 dilution. 10 µM of Y-27632 was added to the media of indicated samples. The expression, of pluripotency markers Tra-1-60, Tra-1-81, SSEA-3 and SSEA-4, was evaluated by flow cytometry. Results are shown in FIG. 17. The percentage of positive cells is indicated on the y-axis. Single human ES cells grown on surface modified plates 3 and 4 can maintain their pluripotency.

Example 8

Rho Kinase Inhibition Promotes Adhesion and Growth of Cells from the Human Embryonic Stem Cell Line H9, Grown as Single Cells on Surface Modified Plates Upon Transfer from Matrigel™

Figure 18:
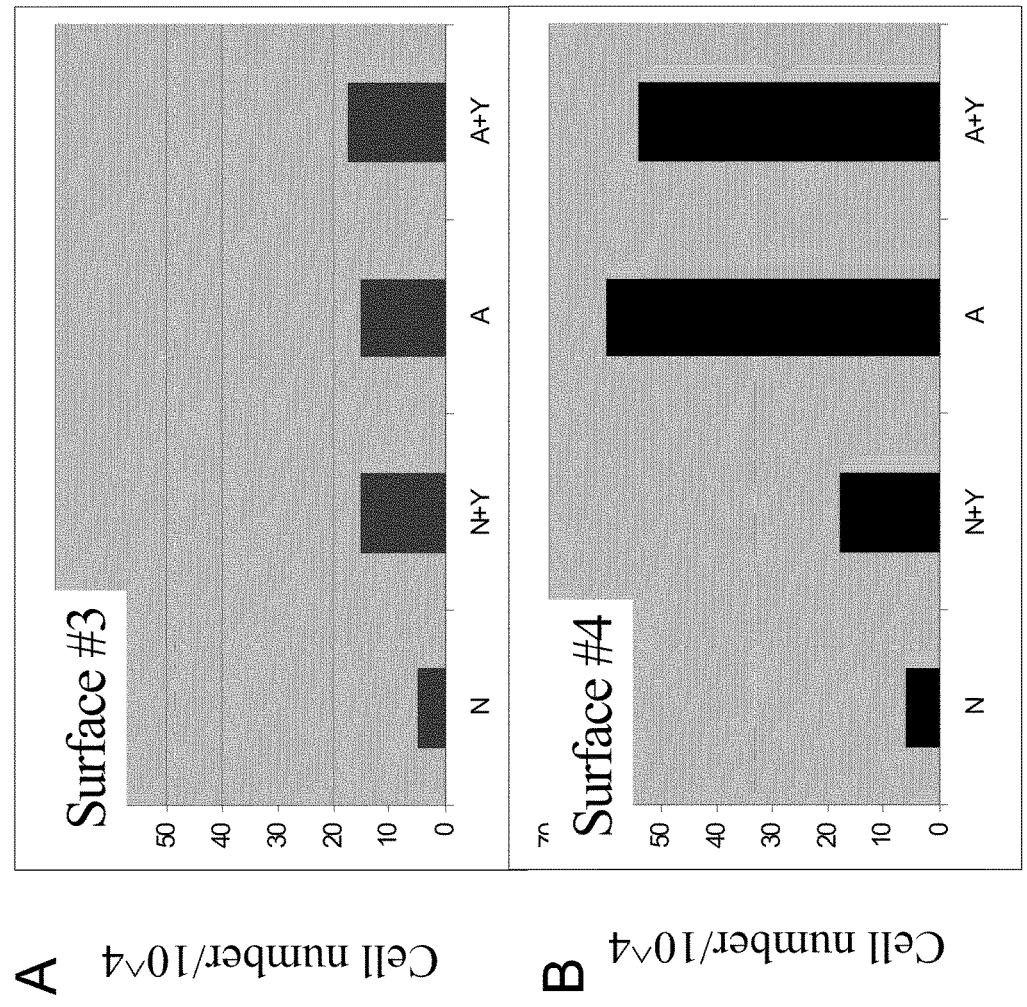
FIG. 18 depicts the total cell number of cells from the human ES cell line H9, that were passaged as single cells, plated onto surface modified plates 3 and 4. The effect of 10 µM of Y-27632 (Y) on cell number was examined on cells passaged on Matrigel™ (naïve, N), and cells passaged 10 times on the surface modified plates (acclimated, A). The different cell conditions are listed on the x-axis and the number of cells divided by $10^4$ is shown in the y-axis.
Figure 19:
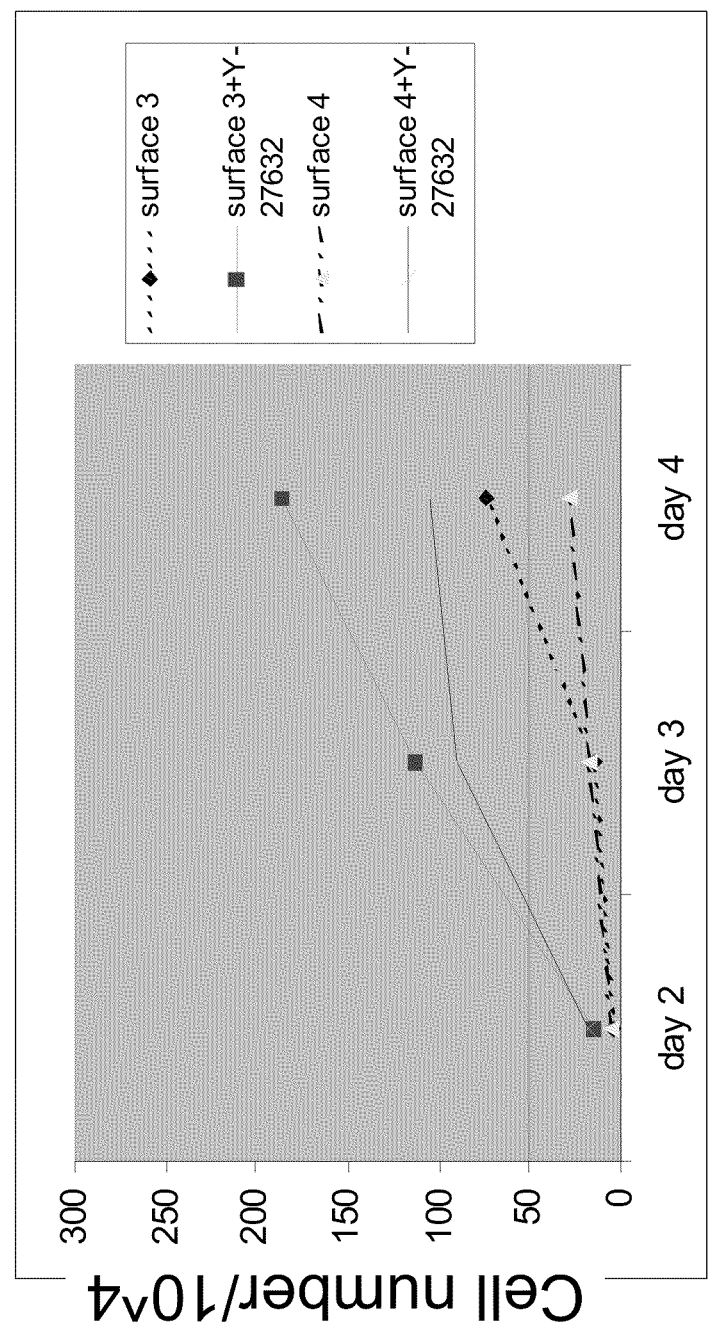
FIG. 19 depicts the rate of growth of cells from the human ES cell line H9, that were passaged as single cells on Matrigel™ treated plates prior to the study. Cells were seeded at $10^4/cm^2$ and cultured in MEF conditioned media with or with out 10 µM of Y-27632 on surface modified plates 3 and 4. The y-axis shows the number of cells collected 2, 3 or 4 days after seeding (divided by 104).
Figure 20:
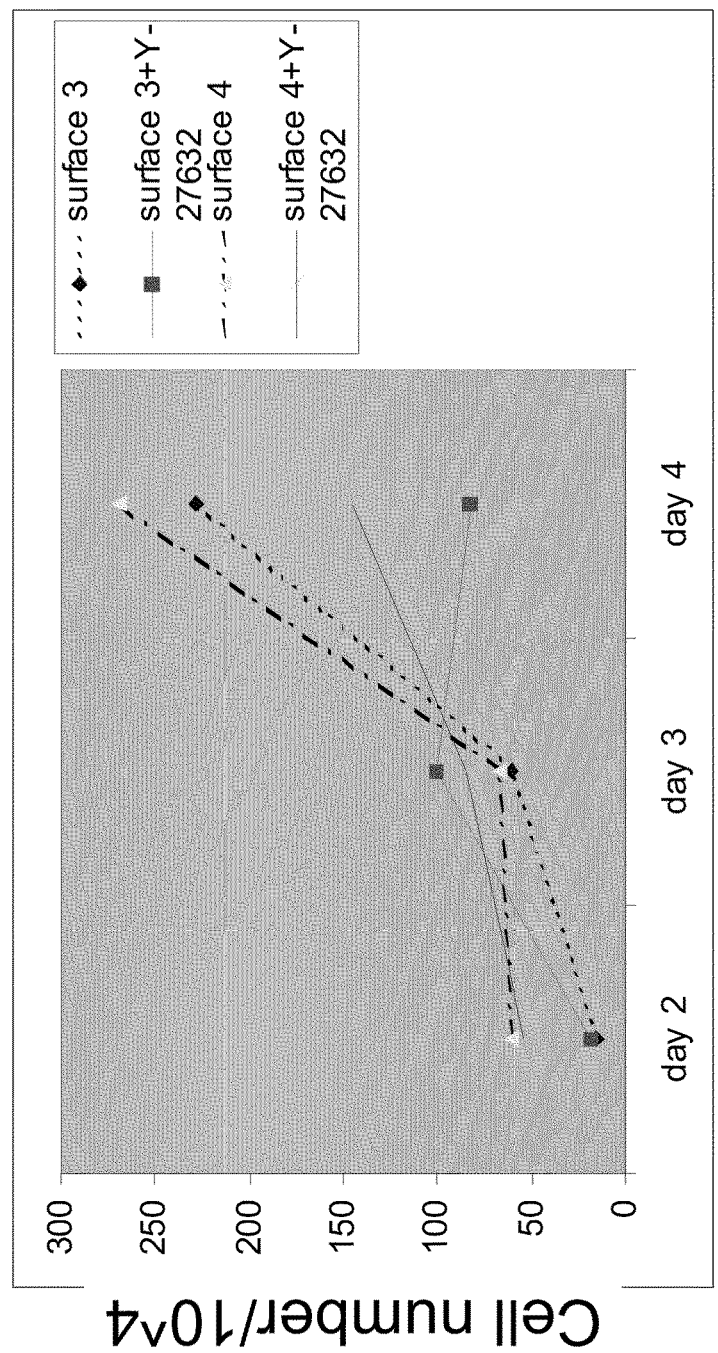
FIG. 20 depicts the rate of growth of cells from the human ES cell line H9, that were passaged as single cells for 10 passages on surface modified plates prior to the study. Cells were seeded at $10^4/cm^2$ and cultured in MEF conditioned media with or with out 10 µM of Y-27632 on surface modified plates 3 and 4. The y-axis shows the number of cells collected 2, 3 or 4 days after seeding (divided by 104).

The role of Y-27632 in human ES cell adhesion and cell growth was studied in relation to the surface modified plates. H9 human ES cells were passaged 38 times with collagenase and 50 times with TrypLE™ Express followed by seeding onto Surfaces modified plates 3 or 4 (naïve cells). Alternatively H9 human ES cells passaged 38 times with collagenase and 38 times followed by Triple Express followed by 9 passages on surface modified plate 3 (Surface 3, acclimated cells), or surface modified plate 4 (Surface 4, acclimated cells). Cells were seeded at a density of $10^4/cm^2$ in MEF conditioned media and grown for two days with or without the presence of 10 μM of Y-27632. Results are shown in FIG. 18. Y-27632 improves attachment of naïve cells to surface modified plates 3 and 4. Y-27632 did not improve attachment of acclimated cells to surface modified plates 3 or 4. surface modified plate 3 improved attachment and/or growth of naïve cells. Surface modified plate 4 improved attachment and/or growth of acclimated human ES cells. The cells were followed for a total of 4 days (FIGS. 19 and 20). The naïve single cells exhibited an increase growth rate when cultured with 10 μM Y-27632 with surface modified plate 3 showing a slight advantage (FIG. 19). The acclimated single cells exhibited improved growth rates with out the 10 μM of Y-27632 (FIG. 20).

Example 9

Surface Modified Plates can be Used to Screen Compounds

Surface modified plates in 96-well configuration and in the Society for Biomolecular Screening (SBS) standard format can be used for growing single human ES cells in the presence of 10 μM Y-27632. Images of H9 single cells plated in 96-well plate wells are shown in FIG. 21. This would allow for the screening of compounds directly in 96-well plates with no interfering cells or adlayers, such as mouse embryonic fibroblasts or Matrigel™, respectively.

Example 10

Figure 22:
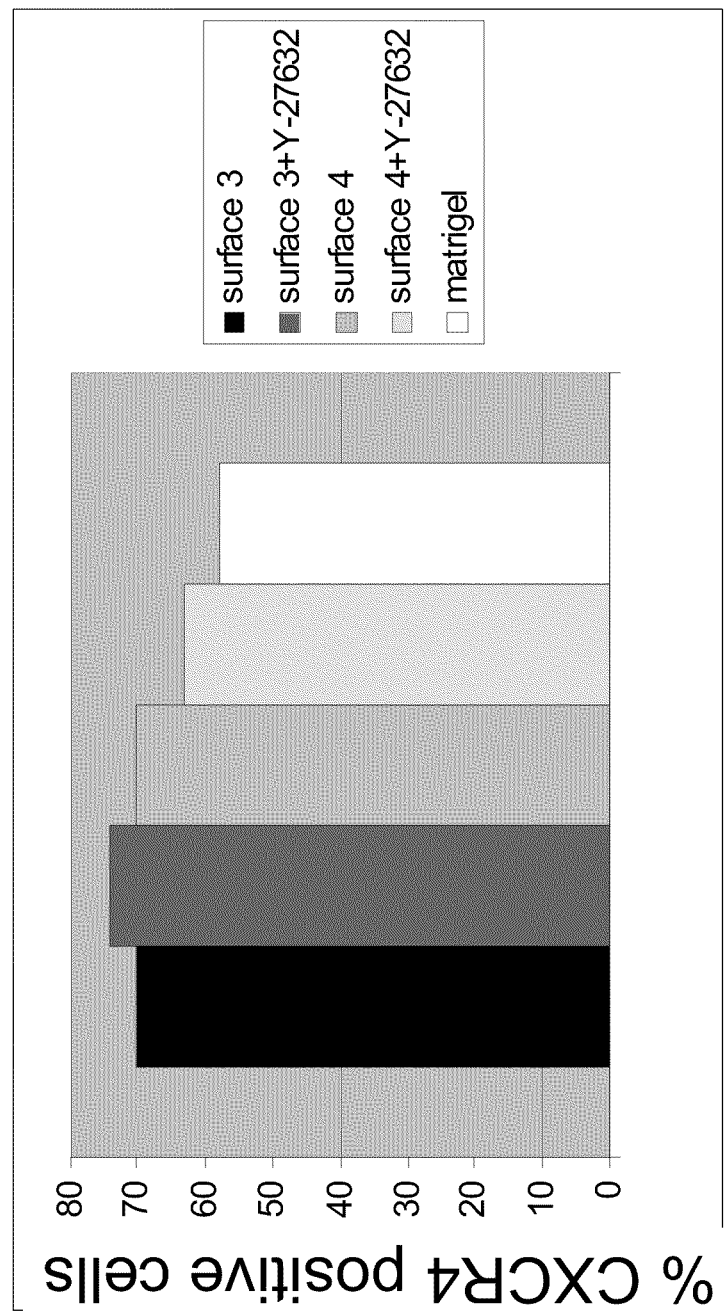
FIG. 22 shows the ability of cells from the human ES cell line H9, that were passaged as single cells, seeded on to surface modified plates 3 and 4 to differentiate into definitive endoderm. The extent of formation of definitive endoderm was determined by measuring CXCR expression by flow cytometry. The effect of 10 µM Y-27632 on the formation of definitive endoderm was investigated. Cells were treated with Y-27632 during expansion. Cells expanded and differentiated on Matrigel™ were included as a control. The y-axis shows percent positive CXCR4 cells obtained by flow cytometry.

Single Embryonic Stem Cells Cultured on Surface Modified Plates are Able to Differentiate into Definitive Endoderm One goal is to differentiate human ES cells into different cell lineages. To determine if surface modified plates can support differentiation, human ES cells were passaged 38 times with collagenase and 38 times with TrypLE™ Express followed by 9 passages on surface modified plate 3 (Surface 3), or surface modified plate 4 (Surface 4). As a positive control, human ES cells were grown on Matrigel™ at 1:30 dilution. 10 μM of Y-27632 was added to the media during expansion of indicated cell samples. After cell expansion, the ability of the cultured cells to form definitive endoderm was evaluated. Briefly, 70% confluent cultures were treated with 100 ng/ml Activin A, 10 ng/ml Wnt3a and 0.5% FBS in DMEM-F12 media for two days. The treatment was followed by 3 days with 100 ng/ml Activin A and 2% FBS in DMEM/F12. Cells differentiated into definitive endoderm are identified by CXCR4 protein expression, via flow cytometry (FIG. 22). The percentage of positive cells is indicated on the y-axis. Human ES cells cultured as single cells can differentiate into definitive endoderm in the presence or absence of Y-27632 on surface modified plates 3 and 4.

Example 11

Single Embryonic Stem Cells Cultured on Surface Modified Plates are Able to Differentiate into Pancreatic Endoderm After completion of the definitive endoderm protocol, the cells were incubated for 3 days with FGF-7 (50 ng/ml; R&D Systems), the sonic hedgehog inhibitor, KAAD cyclopamine (2.5 μM; Sigma-Aldrich) and 2% FBS in DMEM-F12 medium. At this point, cells not treated with Y-27632 during expansion detached from the surface modified plates 3 and 4. The cells treated with Y-27632 during expansion, were incubated an additional four days with FGF-7 (50 ng/ml), KAAD cyclopamine (2.5 μM), Retinoic Acid (1 μM; Sigma-Aldrich) and 1% B27 (Invitrogen) in DMEM-F12 (posterior foregut stage, PF). After this time, cells were incubated an additional four days in Exendin 4 (50 ng/ml; Sigma-Aldrich), DAPT (1 μM; Calbiochem), and 1% B27 in DMEM-F12. Differentiation was continued to the pancreatic endoderm stage (EN). This entailed a three-day treatment with CMRL medium (Invitrogen) containing 50 ng/ml, HGF, IGF (R&D Systems), and Exendin 4 (50 ng/ml), and 1% B27. RNA samples were taken at stages PF and EN from one well of the surface modified plates 3 and 4. These samples were then analyzed by real-time PCR at this step for pancreatic markers Pdx1, NRx6.1, NRx2.2, Pax4, NeuroD, HNF3b, Ptf1a, Insulin and AFP. Evaluation of the same pancreatic endoderm markers was repeated at this stage. RNA samples from untreated human ES cells of the same line were subjected to real-time PCR in parallel to treated samples. Treated samples were normalized to untreated controls set to a fold change of 1. Pdx1 and insulin expression was monitored and compared between surface modified plates.

Figure 23:
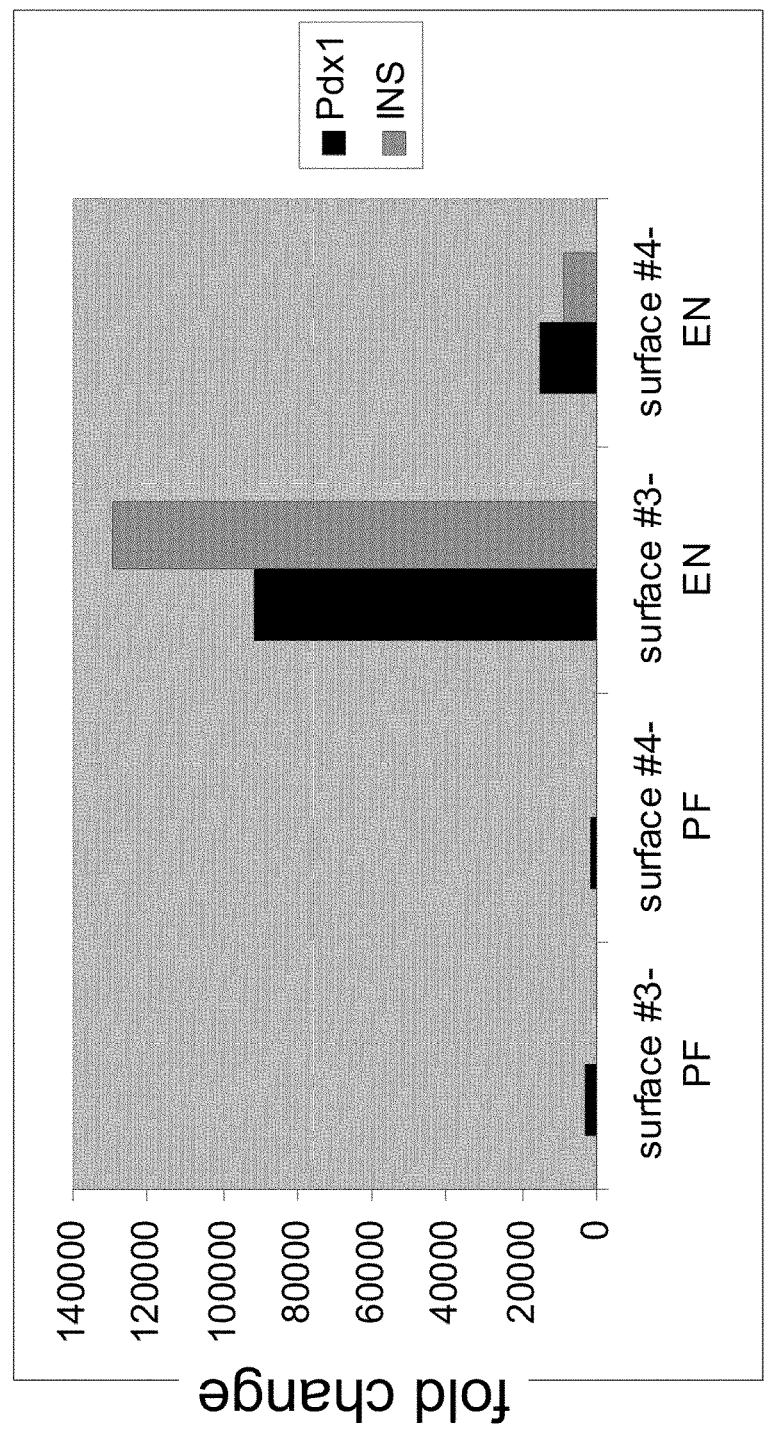
FIG. 23 shows the ability of cells from the human ES cell line H9, that were passaged as single cells, seeded on to surface modified plates 3 and 4 to differentiate into pancreatic endoderm. Cells were plated onto the surface modified plates and cultured in MEF conditioned medium containing 10 µM Y-27632, and passaged 8 times on the surface modified plates prior to differentiation. The y-axis shows the fold increase of pancreatic differentiation marker expression (Ngn3, Pdx1, Insulin) by q-PCR at the posterior foregut stage (PF) and the hormone expressing endocrine cell stage (EN).

Induction of pancreatic endoderm markers was observed from cells treated on surface modified plates 3 and 4, although expression was higher with cells treated on surface modified plate 3 (FIG. 23). Both surface modified plates in the presence of Y-27632 during expansion can support the differentiation of single human ES cells to posterior foregut and pancreatic endoderm whereas single cells not treated with Y-27632 during expansion detached prior to posterior foregut differentiation.

Example 12

H1 and H9 Human ES Cells Adhere to Surface Modified Plates and Adherence is Enhanced by Treating Cells with Y-27632

Figure 24:
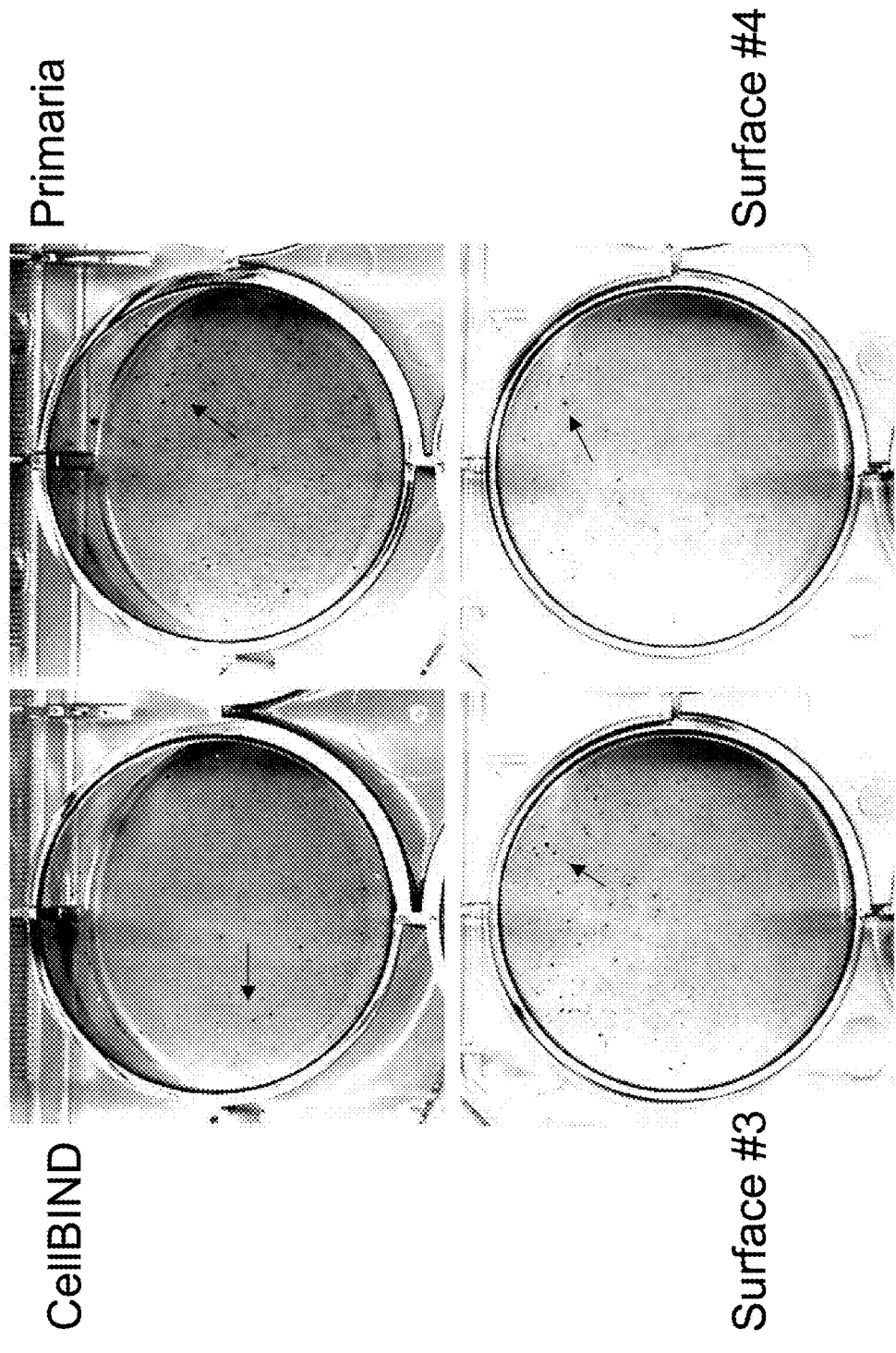
FIG. 24 shows the attachment of human ES cells to surface modified plates. Passage 50 H9 human ES cells were plated at a 1:2 dilution on Surfaces 3 and 4, CellBIND™, and Primaria™. Media was removed from the plates 24 hours after plating and the cells were stained with 0.5% crystal violet, and images taken. Arrows indicate colonies.
Figure 25:
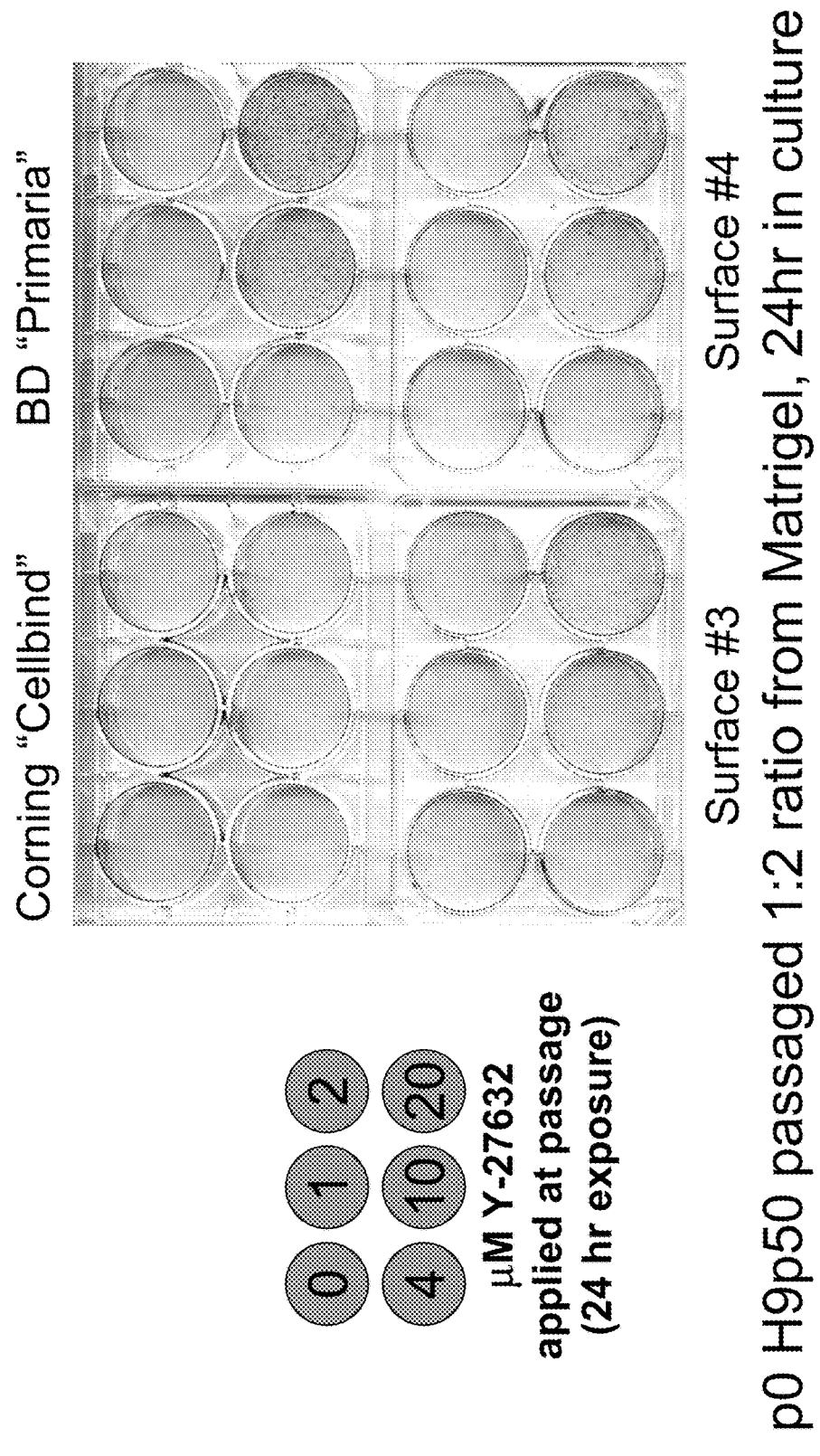
FIG. 25 shows the attachment of human ES cells to surface modified plates. Passage 50 H9 human ES cells were plated at a 1:2 dilution on Surfaces 3 and 4, CellBIND™, and Primaria™ in the presence of various concentrations of Y-27632 (0, 1, 2, 4, 10 and 20 micromolar). Media was removed from the plates 24 hours after plating and the cells were stained with 0.5% crystal violet, and images taken. Colonies are dark spots on the well. Arrows are used to highlight colonies on the untreated wells.
Figure 26:
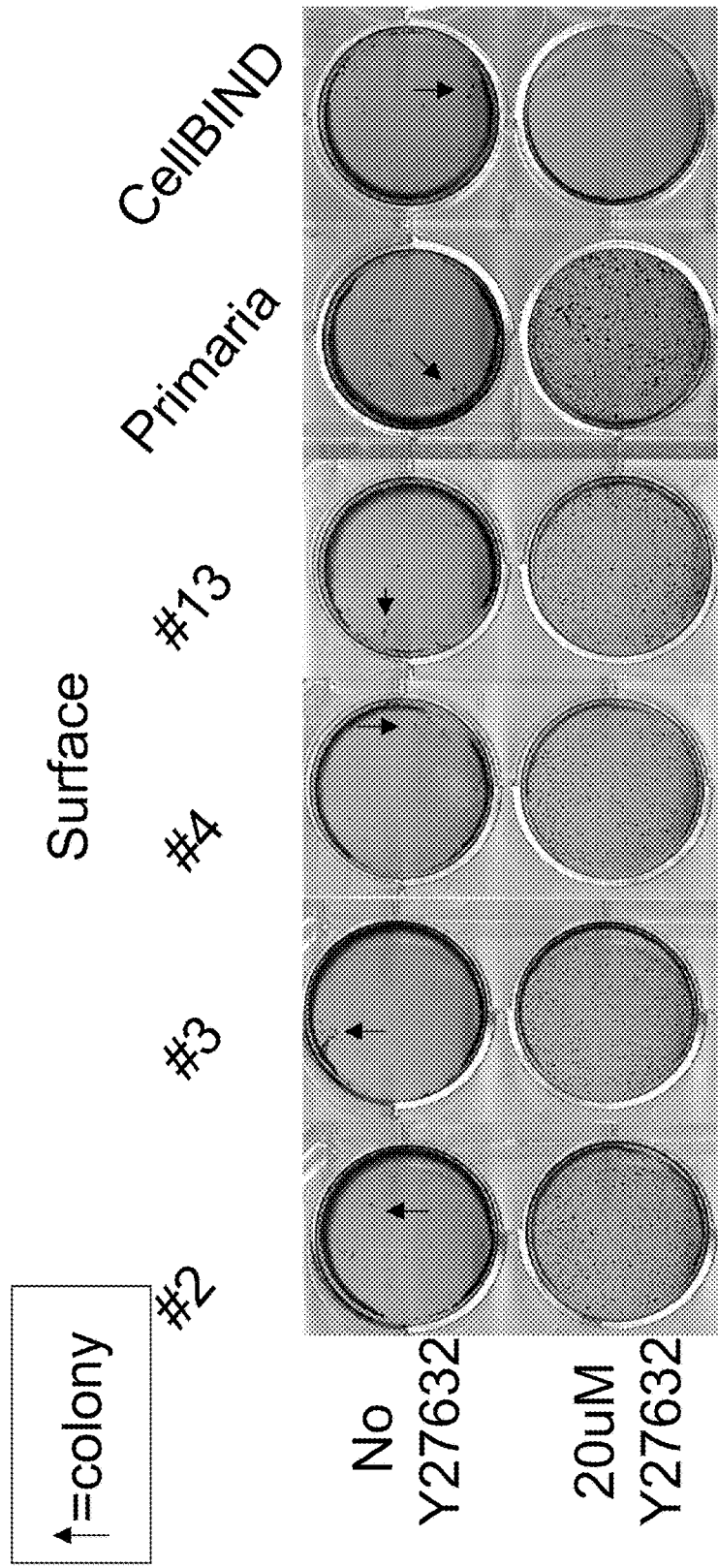
FIG. 26 shows the attachment of human ES cells to surface modified plates. Passage 53 H9 human ES cells were plated at a 1:3 dilution on Surfaces 2-4 and 13, CellBIND™, and Primaria™ in the absence or presence of Y-27632 (0 or 20 micromolar). Media was removed from the plates 48 hours after plating and the cells were stained with 0.5% crystal violet, and images taken. Colonies are dark spots on the well. Arrows are used to highlight colonies on the untreated wells.

Passage 49 H9 human ES cells previously plated to 1:30 Matrigel™ treated plasticware and grown in MEF conditioned media supplemented with 8 ng/ml of bFGF were LIBERASE treated and plated to surface modified plates in MEF conditioned media supplemented with 8 ng/ml of bFGF and not otherwise treated or supplemented with increasing concentrations of Y-27632. 24 and 48 hours after plating H9 human ES cells to surface modified plates small colonies could be observed on Surfaces 2-4 and 13, and CellBIND™, and Primaria™ (cat. no. 353846, Becton Dickinson, Franklin Lakes, N.J.) with crystal violet stain (FIGS. 24-26). Furthermore, the adherence of H9 human ES cell colonies was improved by the addition of Y-27632 and the effect was dose responsive (FIG. 25). Low concentrations of Y-27632 (1 to 2 micromolar) showed a minimal improvement in human ES cell attachment versus untreated human ES cells (FIG. 25) while higher concentrations of Y-27632 (4 to 20 micromolar) promoted adherence of human ES cells to surface modified plates as measured by crystal violet stain (FIGS. 25 and 26).

In addition to the dynamic regulation of human ES cell attachment by addition of Y-27632 to the cell culture media, different rates of adhesion of human ES cells to various surface modified plastics in the presence of Y-27632. For example, cells were less adherent to CellBIND™ plates and were more likely, over time, to detach from CellBIND™ plates even in the presence of sustained Y-27632 treatment while cells were more adherent and less likely to detach from surface modified plates, 3, 4, or 13 or Primaria™ when treated with the Rho kinase inhibitor, Y-27632 (FIGS. 25 and 26).

Example 13

Cells from the Human Embryonic Stem Cell Lines H1 and H9 Attach and Form Colonies at Different Rates on Surface Modified Plates in the Presence of Y-27632

Figure 27:
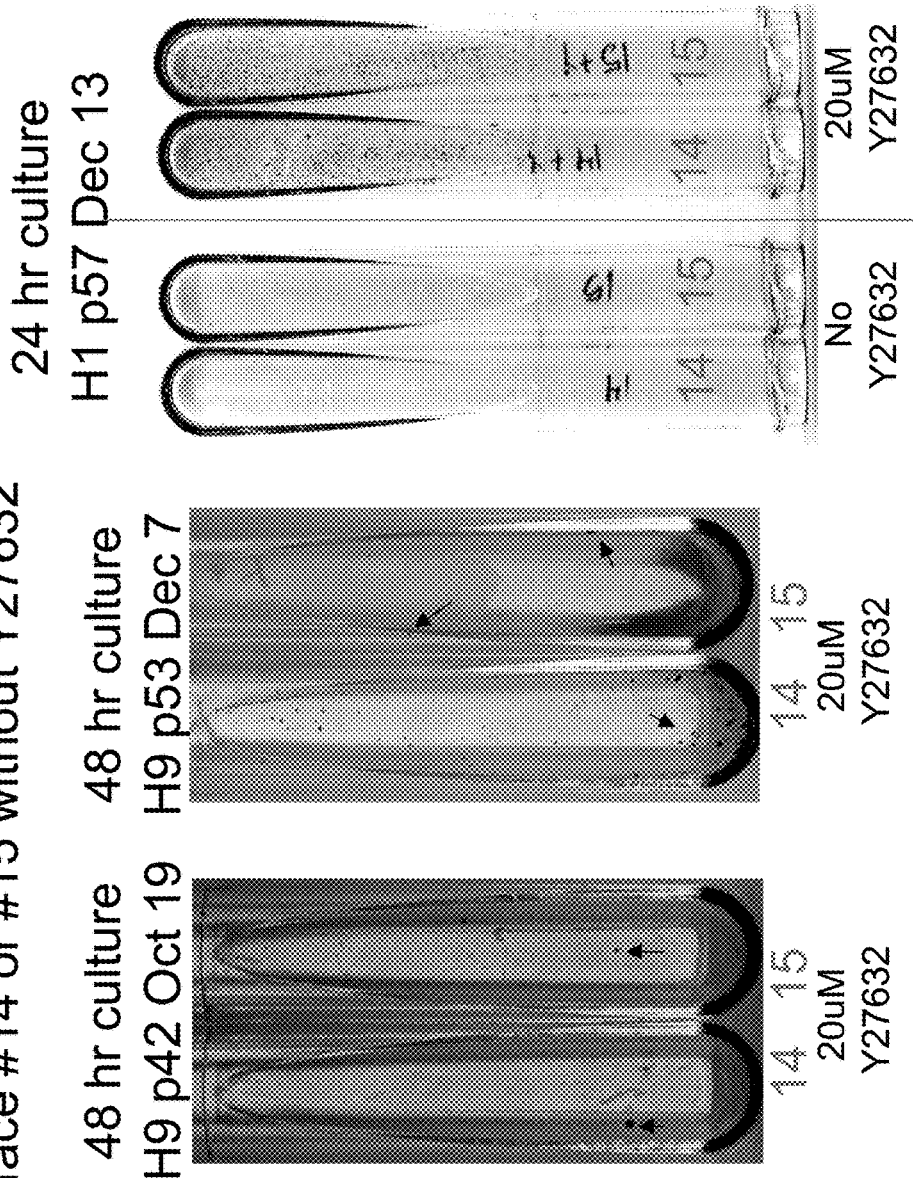
FIG. 27 shows the first attempt (October) and second attempt (December) to attach human H9 ES cells to surface modified plates 14 and 15 and an attempt to attach human H1 ES cells to surface modified plates 14 and 15. Passage 42 and passage 53 H9 human ES, and passage 57 H1 human ES cells were plated at a 1:2 or 1:3 dilution to the modified surfaces in the presence of 20 micromolar Y-27632. Media was removed from the plates 24-48 hours after plating and the cells were stained with 0.5% crystal violet, and images taken. Colonies are dark spots on the well. Arrows are used to highlight colonies on the plates.

H1 and H9 human ES cells previously plated to 1:30 Matrigel™-treated plasticware and grown in MEF conditioned media supplemented with 8 ng/ml of bFGF were LIBERASE treated and plated to surface modified plates in MEF conditioned media supplemented with 8 ng/ml of bFGF and not otherwise treated or supplemented with 20 micromolar Y-27632. Forty-eight hours after plating H9 human ES cells to surface modified plates 14 and 15, small colonies were observed when the media was supplemented with 20 micromolar Y-27632 (attachment and colony formation was variable from experiment to experiment) (FIG. 27). H1 human ES cells also attached to and formed colonies on both Surface 14 and 15 in media supplemented with 20 micromolar Y-27632, and this was more prevalent than the binding observed with H9 human ES cells. These data indicate that there is human ES cell line-to-line variability in attachment to and colony formation on solid substrate surfaces.

Example 14

Human ES Cell Attachment to Surface Modified Plates Using Defined Media

Figure 28:
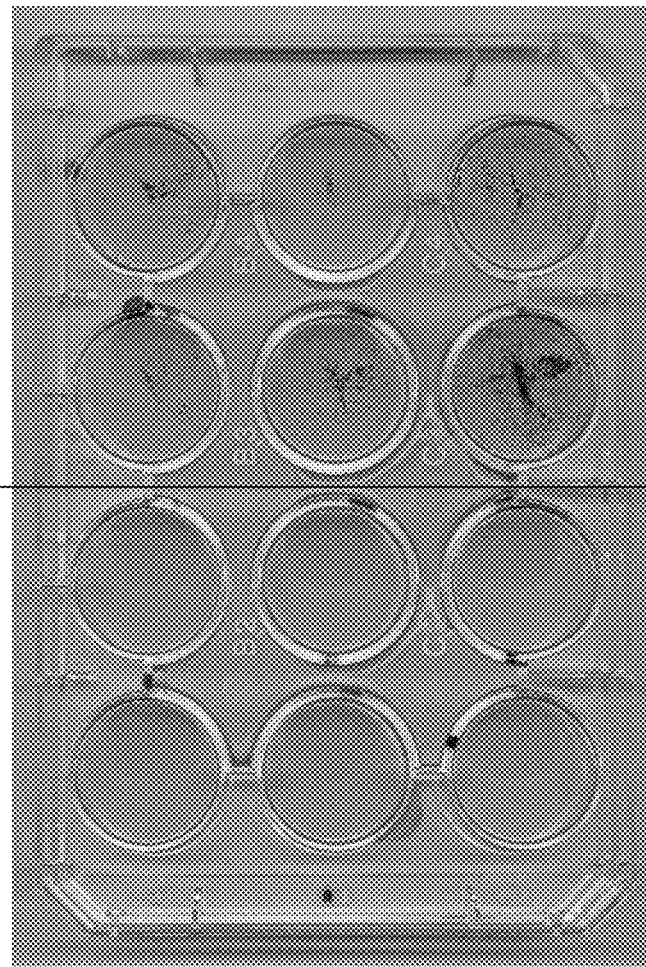
FIG. 28 shows the attachment of human ES cells to a surface modified plate 4 in defined media, mTeSR™. Passage 50 H9 human ES cells were plated at a 1:2 dilution to the modified surfaces in the absence or presence of Y-27632 (0 or 20 micromolar) in wells that were untreated or treated with proteins (0.1% gelatin, 2% BSA, 0.34 mg/ml rat Collagen I, 1:1000 diluted Matrigel™, or 1:5000 diluted Matrigel™). Media was removed from the plates 48 hours after plating and the cells were stained with 0.5% crystal violet, and images taken. Colonies are dark spots on the well.

Passage 49 H9 human ES cells were passaged twice in the define media, mTeSR™, on Matrigel™-treated plasticware. The cells were then LIBERASE treated and plated onto the surface modified plate Nunc4 in mTeSR™ media. Cells were either plated in media with or without 20 micromolar Y-27632. Wells were also treated with various proteins for 30 minutes prior to seeding cells (no treatment, 0.1% gelatin, 2% BSA, 0.34 mg/ml rat Collagen I, 1:1000 Matrigel™, or 1:5000 Matrigel™) to determine if these proteins could promote human ES cell adhesion in defined media with or without Y-27632 (FIG. 28). In the absence of Y-27632, human ES cells plated onto a surface modified plate in defined media did not attach—even in the presence of extracellular matrix proteins such as Collagen I or 1:1000 Matrigel™. However, when 20 micromolar Y-27632 was added to define mTeSR™ media, human ES cells adhered to surface Nunc4. Furthermore, this adherence was equivalent in untreated wells and wells treated with 0.1% gelatin, 2% BSA, and 0.34 mg/ml rat Collagen I. There was a modest increase in human ES cell attachment in wells with low concentrations of Matrigel™ (1:1000 and 1:5000 dilutions), however these concentrations of Matrigel™ were insufficient to promote adhesion in the absence of Y-27632. These results demonstrate that in the presence of the ROCK Inhibitor, Y-27632, human ES cells can be cultured on modified plastic substrates in defined media and that low concentrations of Matrigel™ of about 1:1000 or 1:5000 can improve this adhesion.

Example 15

Surface Modified Plates in a Flask Format can Promote Human ES Cell Attachment and Differentiation to Definitive Endoderm and Pancreatic Endoderm H1 and H9 human ES cells previously plated to 1:30 Matrigel™-treated plasticware and grown in MEF conditioned media supplemented with 8 ng/ml of bFGF were LIBERASE treated and plated to T25, T75, T150, and T175 flasks at a 1:2 or 1:3 seeding density onto various size flasks with modified surfaces. The cells were seeded in MEF conditioned media supplementedwith 8 ng/ml of bFGF and 20 micromolar Y-27632. Human ES cell colonies were then allowed to grow, with daily media changes of MEF conditioned media supplemented with 8 ng/ml of bFGF and 20 micromolar Y-27632, until the plates were approximately 50% confluent. At this time, the media was changed to DMEM/F12 media containing 2% BSA, 100 ng/ml Activin A, 20 ng/ml Wnt3a, and 20 micromolar Y-27632 and the cells were maintained in this media for 2 days with daily media changes. On day 3 and 4,the media was changed to DMEM/F12 media containing 2% BSA, 100 ng/ml Activin A, and 20 micromolar Y-27632. Cells were then released from the surface with TrypLE and assays by flow cytometry for expression of the definitive endoderm (DE) surface marker, CXCR4. It was observed that under these conditions, human ES cells differentiated to a highly CXCR4 positive population, that was as high as almost 90% CXCR4+, indicating that the cells were mostly differentiated to definitive endoderm (Table 5). Furthermore, the attachment of the cells to the culture surface during growth or during differentiation was dependent on maintaining ROCK inhibition, since withdrawal of Y-27632 from the culture media resulted in cell detachment from the plastic.

To determine if pancreatic endoderm could be formed from the definitive endoderm derived on surface modified plates in flask format, the cells for an additional four days with Y-27632 (20 micromolar), FGF-7 (50 ng/ml), KAAD cyclopamine (2.5 micromolar), and 1% B27 (Invitrogen) in DMEM-F12 and then an additional four days in this media supplemented with Retinoic Acid (1 micromolar; Sigma-Aldrich) to differentiate the cells to a pancreatic endoderm stage. RNA samples were then taken and analyzed by real-time PCR for the pancreatic marker Pdx1. Treated samples were normalized to untreated controls set to a fold change of 1. It was observed that samples had increased levels of PDX1 versus undifferentiated human ES cells, with mRNA levels at least 256 fold higher in the differentiated cells than that observed in undifferentiated human ES cells.

Example 16

Surface Treatment and Surface Modified Plates

Surface modified plates were prepared by treating injection molded items using a corona plasma treatment or a microwave plasma treatment (Table 6). The polymer materials used in injection molding were polystyrene, polycarbonate, a blend of polycarbonate and polystyrene, and cyclic olefin copolymer. The surface modified plates were individually packed in plastic bags, then sterilized by gamma irradiation (25 kGy), and finally stored at room temperature until used in cell culture or surface characterization experiments. Surface modified plates 18, 30 and 31-32 were molded using the same polymer materials as surface modified plates 19, 33 and 34, respectively, but were not plasma treated. Surfaces 14 and 31 were not gamma irradiated.

Corona plasma treatment was carried out in a metal vacuum chamber with only one electrode inside the chamber and electrically isolated from the inside of chamber (C-Lab Plasma; Vetaphone A/S, Denmark). The metal walls served as counter electrode (ground). A self-tuning corona generator generated the electrical field giving sufficient energy to generate plasma in the entire chamber. An item to be treated was placed at the bottom of the chamber. The chamber was closed and evacuated to a pressure of $10^{-2}$ mbar. At this pressure the valve to the vacuum pump was closed and the corona generator engaged. The generator was set to generate an output of 2000 W. The plasma was energized for 5 to 60 seconds. The gas inlet valve (air) was then opened, and the pressure in the chamber returned to atmospheric level.

The microwave plasma treatment was carried out in a quarts vacuum chambers (Model 300-E for surface modified plates 5-12 and Model 440 for surface modified plates 14 and 15; both from Technics Plasma GmbH, Germany). The energy to generate the plasma was supplied by a 2.43 GHz microwave generator outside the chamber. An item to be treated was placed on a glass plate inside the chamber. The chamber was closed and evacuated to a pressure between 0.3 and 0.5 mbar. The valve to the vacuum pump was kept open, and the pressure was maintained at the desired value by adjusting gas (air or oxygen) flow with the gas inlet valve. The microwave generator was then engaged. The generator was set to generate an output of 500 or 600 W. The pump valve was then closed, and the air inlet valve was opened, in order to bring the pressure in the chamber to atmospheric level.

Table 6 shows power, time, pressure, and gasses used in preparing surface modified plates by corona plasma or microwave plasma.

Example 17

Figure 29:
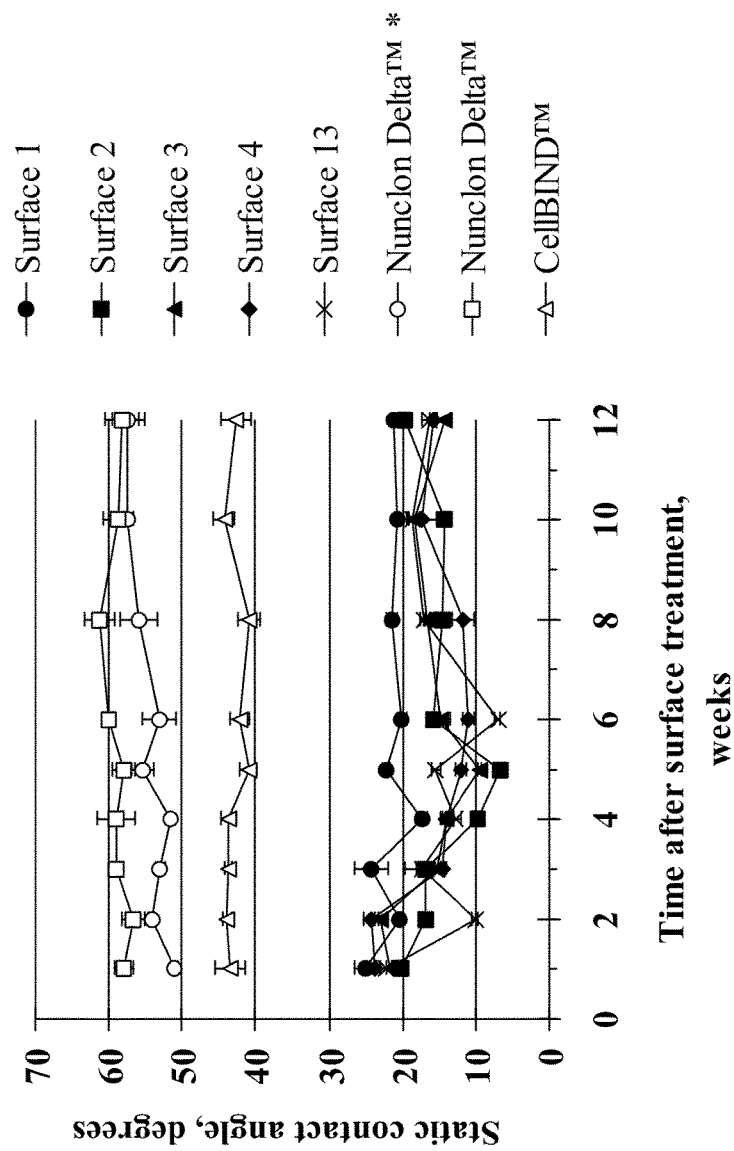
FIG. 29 shows the water contact angles of surface modified plates measured over 11 weeks using the static sessile drop method. The first measurement was done one week after surface treatment and sterilization. Each data point represents the mean contact angle (one measurement on each of 7 drops). The contact angles on Nuclon Delta™ and CellBIND™ plates were measured under the same experimental conditions as Surfaces 1-4 and 13, but the surface treatment and sterilization was done more than 12 weeks before the first measurement (Nuclon Delta™* was sterilized one week before the first measurement).

Surface Characterization of the Surface Modified Plates of the Present Invention Water Contact Angles Surface modified plates 1-4 and 13 were individually packed in plastic bags, sterilized, and stored at room temperature throughout the test period. Contact angles were first measured one week after surface treatment and sterilization, and then again at the time points given in FIG. 29. All contact angle measurements were done using the static sessile drop method and a PG-X measuring Head from FIBRO Systems AB, Sweden [goniometer consisting of video camera and computer software (v. 3.1)]. The tangent leaning method was used for calculation of the contact angles. props of 4.0 μL MilliQ water was applied using automatic drop application in static mode, according to the manufactures instructions. The contact angle of each drop was measured once (7 drops were applied to each sample per time point). For each time point, a new sample was used in order to avoid any influence from earlier measurements. Measurements on Nunclon Delta™ and CellBIND™ surfaces was performed under the same experimental conditions as measurements on Surface 1-4 and 13, but the surface treatment and sterilization was done more than 12 weeks before the first measurement (Nunclon Delta™* was sterilized one week before the first measurement). FIG. 29 shows that surface modified plates 1-4 and 13 were of similar hydrophilicity and more hydrophilic (lower water contact angles) than Nunclon Delta™ and CellBIND™ surfaces. The hydrophilicity of surface modified plates 1-4 and 13 was stable for at least 12 weeks after surface treatment and sterilization.

CellBIND™ has previously been described as having a contact angle of 13.4 degrees (standard deviation of 4 degrees) [Corning Technical Report (2005), Corning® CellBIND® Surface: An Improved Surface for Enhanced Cell Attachment (CLS-AN-057 REV1).

Negative Charge Density

The density of negative charges on surface modified plates 1-4 and 13, Nunclon Delta™ surface, CellBIND™ surface, Primaria™ surface, Falcon™ surface, and a non-treated (but sterilized) polystyrene surface (all in 3-cm dish format) was determined. Three ml of aqueous crystal violet solution (0.015% w/v) was dispensed in each dish, and dishes were incubated for 60 minutes at room temperature under gentle shaking (50 rpm). In order to remove crystal violet not bound to the surfaces, the dishes were washed three times with 3 ml MilliQ water, and then dried over night at 60° C. The crystal violet bound to the surface was desorbed by addition of 1.5 ml of 0.1 M HCl in EtOH solution (99%) and incubating the dishes for 2 minutes at room temperature under gentle shaking (50 rpm). Absorbance of the HCl:EtOH solution with desorbed crystal violet was measured at 590 nm using an EnVision 2100 microplate reader (Perkin Elmer; Waltham, Mass., USA). Absorbance values were corrected for background absorbance of HCl:EtOH solution. The negative charge density was measured on three dishes per surface, and absorbance measurement was performed in triplicate for each dish.

Figure 30:
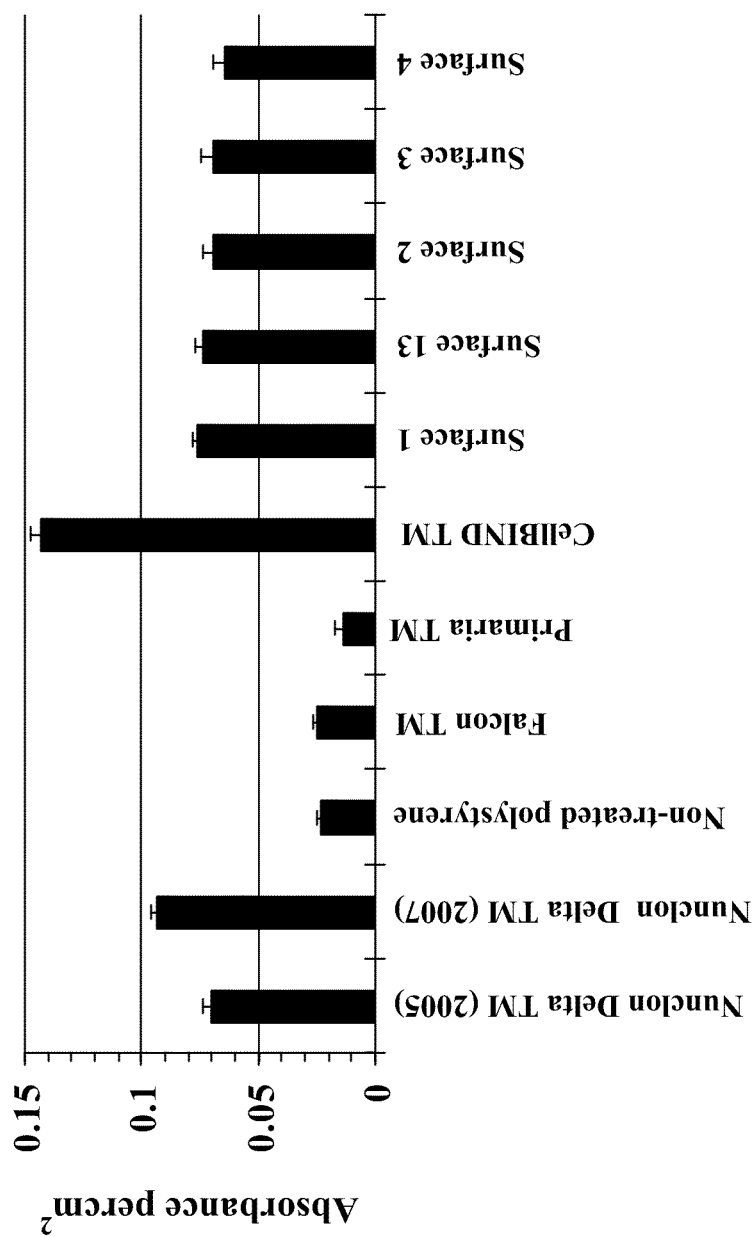
FIG. 30 shows the density of negative charges on surface modified plates measured as reactivity of surfaces with positively charged crystal violet. Three samples of each surface were tested, and absorbance measurements on desorbed crystal violet from each sample were performed in triplicate. Mean and standard deviation of nine measurements are given.

The negative charge density for surface modified plates is shown in FIG. 30. The negative charge densities of Surfaces 1-4 and 13 were similar, but longer surface treatment time in the interval of 5-60 seconds tended to result in a lower surface negative charge density. Surfaces 1-4 and 13 had significantly lower negative charge densities than CellBIND™ surface and a Nunclon Delta™ surface treated in 2007. Surfaces 1-4 and 13 had negative charge densities at the same level as a Nunclon Delta™ surface treated in 2005, and significantly higher negative charge densities than Primaria™ surface, Falcon™ surface, and a non-treated (but sterilized) polystyrene surface. The lower negative charge density of Nunclon Delta™ surface treated in 2005 than of Nunclon Delta™ surface treated in 2007, suggest that surface-treated polystyrene becomes slightly less negatively charged over time. The high level of negative charge density of CellBIND™ is not because of higher surface roughness and thus surface area (See AFM analysis in this Example).

X-Ray Photoelectron Spectroscopy (XPS)

Surface modified plates 1-4 and 13-15, and plates with Nunclon Delta™, Costar™, Falcon™, CellBIND™ and Primaria™ surfaces were analyzed using XPS. Sample was presented to the x-ray source by cutting sections from the plates and mounting them with spring clips onto a stainless steel sample holder. Samples were irradiated with Al kα radiation (1486 eV). The analysis was performed with an angle of 45° between the sample and analyzer. The spectra were curve fit using the software package provided by the instrument's vendor, Physical Electronics. The software utilized commercial Matlab routines for data processing. The instrument used for the analysis was a Physical Electronics Model 5400 X-Ray Photoelectron Spectrometer. The outermost two to five nanometers in depth in a region of about one millimeter in diameter from the surface treated part of the plates was analyzed in each of two plates per surface.

Surface elemental composition in units of atomic percent is shown in Table 7. All surface modified plates contained carbon, oxygen and nitrogen (hydrogen is not detected in XPS) in the surface. Surfaces 1-4, Surface 13 and Cell-BIND™ surface contained more oxygen than the other surfaces analyzed. Surfaces 1-4 and Surfaces 13-15 contained less nitrogen than Primaria™, but more nitrogen than the surfaces of Nunclon Delta™, Costar™, Falcon™, and CellBIND™ plates. Oxygen and nitrogen levels correlated positively with longer surface treatment time (Surfaces 1-4 and 13), and the highest levels of both of these elements were obtained using 30 or 60 seconds of corona plasma treatment (Surface 3 and Surface 4, respectively). Surfaces 3 and 4 were similar in elemental composition. Surfaces 2 and 13 were similar in elemental composition, and more like Surfaces 3 and 4 than Surface 1 in elemental composition.

C1s spectra peaks were curve fit (best chi-squared fit), in order to identify and quantify the bonding environments for carbon in the surfaces, by using peak widths and energy locations for species as found in the literature (Table 8). The concentrations are reported in units of atomic percent, which were obtained by multiplying the area percent by the atomic concentration. Surfaces 2-4 and 13 were similar in terms of the carbon bonding environments. The proportion of carbon in C*—C—O—C—C* bonding environment was lower in Surfaces 2-4 and 13 than in the other surfaces analyzed. The proportion of carbon in O—[C=O]-O bonding environment was higher in Surfaces 2-4 and 13 than in the other surfaces analyzed. Similarities between Surfaces 2-4 and 13 and Surface 1, CellBIND™ surface, and/or Primaria™ surface were also identified. The proportion of carbon in C—O—C or C—NH3$^+$ bonding environment (same energy location in spectra) was higher in Surfaces 1-4 and 13 than in the other surfaces analyzed. The proportion of carbon in C—O—C*=O bonding environment was higher in Surfaces 2-4, Surface 13, and Primaria™ surface than in the other surfaces analyzed. The proportion of carbon in $CO_3$-bonding environment was higher in Surfaces 2-4, Surface 13, and CellBIND™ surface than in the other surfaces analyzed. The proportion of carbon in C=O bonding environment was higher in Surfaces 1-4, Surface 13, and CellBIND™ surface than in the other surfaces analyzed. The proportion of carbon in C—[O]-C bonding environment was higher in Surfaces 1-4, Surface 13, CellBIND™ surface, and Primaria™ surface than in the other surfaces analyzed. The energy loss peak resulted from an aromatic π→π* transition, and is an indicator of surface aromaticity.

The O1s spectra peaks were almost Gaussian and could not be curve fit. N1s spectra peaks were curve fit (best chi-squared fit), in order to identify and quantify the bonding environments for nitrogen in the surfaces, by using peak widths and energy locations for species as found in the literature (Table 9). The concentrations are reported in units of atomic percent, which were obtained by multiplying the area percent by the atomic concentration. The N1s signals from Nunclon Delta™, CellBIND™, Costar™, and Falcon™ surfaces were weak, and it was, therefore, not possible to do identification of the bonding environments for nitrogen in these surfaces. N1s spectra were indistinguishable for surface modified plates 1-4 and 13, and data resulting from curve fitting of two representative N1s spectra is shown. The proportion of nitrogen in —$NH_3^+$ bonding environment was higher in Surfaces 1-4 and 13 than in Surfaces 14 and 15 and Primaria™ surface. Nitrogen in —$NH_2$ bonding environment was detected only in Surfaces 14 and 15 and Primaria™ surface. Nitrogen in —$NO_2$ bonding environment was detected only in Surfaces 1-4 and 13, and in a single sample of Surface 15. Nitrogen in —$NO_3$ bonding environment was detected only in Surface 15 and Primaria™ surface.

CellBIND™ has previously been described as having an elemental composition of 70.4% carbon, 29.0% oxygen, 0.6% nitrogen, and <0.01% other elements, and a relatively high concentration of C—[O]—C, C=O, and COOH/R groups, as analyzed by ESCA [Corning Technical Report (2005), Corning® CellBIND® Surface: An Improved Surface for Enhanced Cell Attachment (CLS-AN-057 REV1).

Primaria™ has previously been described as having an elemental composition of 74.6% carbon, 14.1% oxygen, 11.1% nitrogen, and 0.2% other elements, with mainly nitrile (C≡N) and urea [HN(C=O)NH]carbon-to-nitrogen bonding environments, as analyzed by ESCA.

Atomic Force Microscopy (AFM)

Surface modified plates 1-4 and 13, and plates with Nunclon Delta™ and CellBIND™ surfaces were analyzed using AFM. Samples were analyzed using a Digital Instruments Multimode Atomic Force Microscope in tapping mode. The tip used was a tapping mode tip, type TESP7. Samples were attached to the sample disks with double sticky tape. Regions of 10 μm×10 μm and 500 nm×500 nm of the surface-treated part of the plates were analyzed. Surface mean roughness (Ra) and maximum height (Rmax) in units of nanometers are shown in Table 10. Like the plates with Nunclon Delta™ and CellBIND™ surfaces, surface modified plates 1-4 and 13 were relatively smooth, and Ra and Rmax did not correlate with surface treatment time in either of the two scans. Analysis of non-treated polystyrene and oxidized polystyrene surfaces intended for cell culture, and Primaria™ surface has been described by Shen and Horbett (J. Biomed. Mater. Res. 57:336-345, 2001): surface roughness approximately 4 nm for all three surfaces.

Example 18

Surface Elemental Composition and Contact Angle in Relation to Human ES Cell Attachment and Colony Formation A summary of the results of the XPS analysis of surface elemental composition, the surface contact angle measurements, and human ES cell attachment and colony formation experiments is given in Table 11.

Human ES cell attachment to and colony formation (at least 15 colonies per 10 $cm^2$ surface) on a solid substrate surface in the absence of a compound capable of inhibiting Rho or Rho kinase was observed on only surface modified plates 2-4 and 13, CellBIND™ plates, and Primaria™ plates (cells were presented to the surfaces as a suspension of clusters of cells). Surface modified plates 2-4 and 13 supported cell attachment, colony formation and passaging. After about three passages, the growth rate of human ES cells on surface modified plates 2-4 and 13 declined spontaneously (only in the absence of Rho inhibition and Rho kinase inhibition), although cell morphology indicated that the cells were not differentiating. Furthermore, pluripotency marker expression was maintained in cells passaged four times on Surface 3. CellBIND™ plates supported human ES cell attachment and colony formation, but differentiation of the cells was observed prior to the first passage. Based upon cell morphology observations, Primaria™ plates supported human ES cell attachment and colony formation, without signs of differentiation (passaging was not tested). Both oxygen (for example, Surface 2 versus Surface 14) and nitrogen (for example, Primaria™ versus Costar™; and Surfaces 2 and 13 versus CellBIND™) content of surfaces had an effect on the ability of the surfaces to support human ES cell attachment and colony formation in the absence of Rho inhibition and Rho kinase inhibition. Surfaces with a nitrogen content of at least about 0.9%, a sum of nitrogen and oxygen content of at least about 22.3%, and a water contact angle of at least about 13.9 degrees supported human ES cell attachment and colony formation in the absence of Rho inhibition or Rho kinase inhibition.

Human ES cell attachment and colony formation (at least 15 colonies per 10 cm$^2$ surface) on a solid substrate surface in the presence of a compound capable of inhibiting Rho or Rho kinase was observed on surface modified plates 1-15, surface modified plate 19, surface modified plate 33, surface modified plate 34, CellBIND™ and Primaria™ (cells were presented to the surfaces as a suspension of clusters of cells). We noted that surfaces 2-4 and 13 and Primaria™ were better than surfaces 1, 19, 33 and 34 and CellBIND™, which again were better than surfaces 5-12, 14 and 15, at promoting human ES cell attachment and colony formation. On surface modified plates 3 and 4, and in the presence of a Rho kinase inhibitor, human ES cells attached and formed colonies that expanded and could be passaged at least 10 times, giving rise to pluripotent cells with normal karyotype (karyotype tested only in cells grown on Surface 4). Both oxygen (for example, CellBIND™ versus Nunclon Delta™) and nitrogen (for example, Primaria™ versus Costar™; and Surfaces 2 and 13 versus CellBIND™) content of surfaces had an effect on the ability of the surfaces to support human ES cell attachment and colony formation in the presence of Rho kinase inhibition. Surfaces with a nitrogen content of at least about 0.5%, a sum of nitrogen and oxygen content of at least about 17.2%, and a water contact angle of at least about 13.9 degrees supported human ES cell attachment and colony formation in the presence of Rho kinase inhibition. Surfaces with a nitrogen content of at least about 0.5%, a sum of nitrogen and oxygen content of at least about 17.3% but less than 19.9%, and a water contact angle of at least about 9.4 degrees supported human ES cell attachment and colony formation in the presence of Rho kinase inhibition in some cases (surface 14), but not in others (surfaces 22-24).

We noted that removal of Rho kinase inhibitor from human ES cell cultures cultured on surface modified plate 4 resulted in detachment of the human ES cells from the surface of the solid substrate. The cells could then be reattached to the surface by re-treatment with a Rho kinase inhibitor. Given that enzymatic passage of human ES cells is a potential stressor and may cause karyotypic instability, using temporary removal of Rho kinase inhibitor to passage human ES cells could eliminate the stresses of enzymatic passage.

Human ES cell attachment and colony formation was also demonstrated using animal-component-free medium, Rho kinase inhibition and surface modified plate 4. Pre-treatment of surface modified plate 4 with extracellular matrix proteins resulted in more colonies, but only in the presence of Rho kinase inhibition.

In addition to passaging human ES cells with enzymatic methods that maintain colony style culture conditions by passaging cells as clusters, human ES cells could also be passaged as single cells using enzymes like TrypLE™ or Accutase™. In the presence or in the absence of Rho kinase inhibitor, human ES cell colonies dissociated into a suspension of single cells using TrypLE™ attached to surface modified plates 3 and 4, and formed colonies that could be passaged at least five times and give rise to cells with pluripotency markers.

Removal of Rho kinase inhibitor from the human ES cell cultures prepared by passaging the cells as a suspension of single cells did not result in detachment of the human ES cells from the surface of the solid substrate, but resulted in colonies that grew faster than if the Rho kinase inhibitor was not removed.

Example 19

Treatment with Y-27632 Enhance HEK293 Cell Attachment to Surface Modified Plates Human embryonic kidney cells 293 (HEK293, ECACC no. 85120602) were maintained in Eagle's Minimum Essential Medium (EMEM; Lonza, Verviers, Belgium) containing 10% fetal bovine serum (FBS; Lonza). The cells were adapted to Pro293a-CDM medium (Lonza), a chemically defined, serum-free medium optimized for cultivation of adherent HEK293, by gradually and over several passages using the sequential ratios of 3:1, 1:1, 1:3, 1:7, and finally 0:1 of serum-supplemented EMEM and Pro293a-CDM medium. For maintenance and adaptation, HEK293 cells were seeded at $2.0 \times 10^4$ cells/cm$^2$ in 75-cm$^2$ flasks with Nunclon Delta™ surface (Thermo Fisher Scientific, Roskilde, Denmark) and passaged at 70-80% confluence using Trypsin/EDTA for dissociation.

Pro293a-CDM medium (100 µl) supplemented with Y-27632 (Sigma Chemical Co., St. Louis, Mo.) in concentrations of 1.0, 4.0 or 10 µM was dispensed in flat-bottomed, 96-well plates with Surface 4, Nunclon Delta™ surface, or CellBIND™ surface. Another 100 µl of Pro293a-CDM medium with HEK293 cells was added to the wells ($4.0 \times 10^4$ cells/cm$^2$). The cultures were then incubated at 37° C. in a humidified atmosphere of 5% $CO_2$ in air for: (i) 96 hours; or (ii) 48 hours, followed by washing cultures once with 200 µl Dulbecco's Phosphate Buffered Saline (DPBS; Lonza), then adding 200 µl of Pro293a-CDM medium without Y-27632, and finally incubating cultures for another 48 hours.

The number of viable cells in the wells was then determined using a lactate dehydrogenase (LDH) activity kit from Roche, Switzerland. Briefly, wells were washed with Pro293a-CDM medium, and adherent cells were lysed in 100 µl DPBS with 2% (v/v) Triton X-100 (Sigma Chemical Co.) during a 30-min incubation at 37° C. Lysate and 100-µl catalyst and dye reagent mixture were mixed and incubated in the dark at 25° C. for 30 min. The reaction was stopped by adding 50 µl of 1.0 M HCl, and the absorbance at 490 nm was measured in a microplate reader (Genios Pro; Tecan, Austria). The number of cells was calculated using the A490 values from these samples and from standards containing LDH from a known number of cells.

Figure 31A:
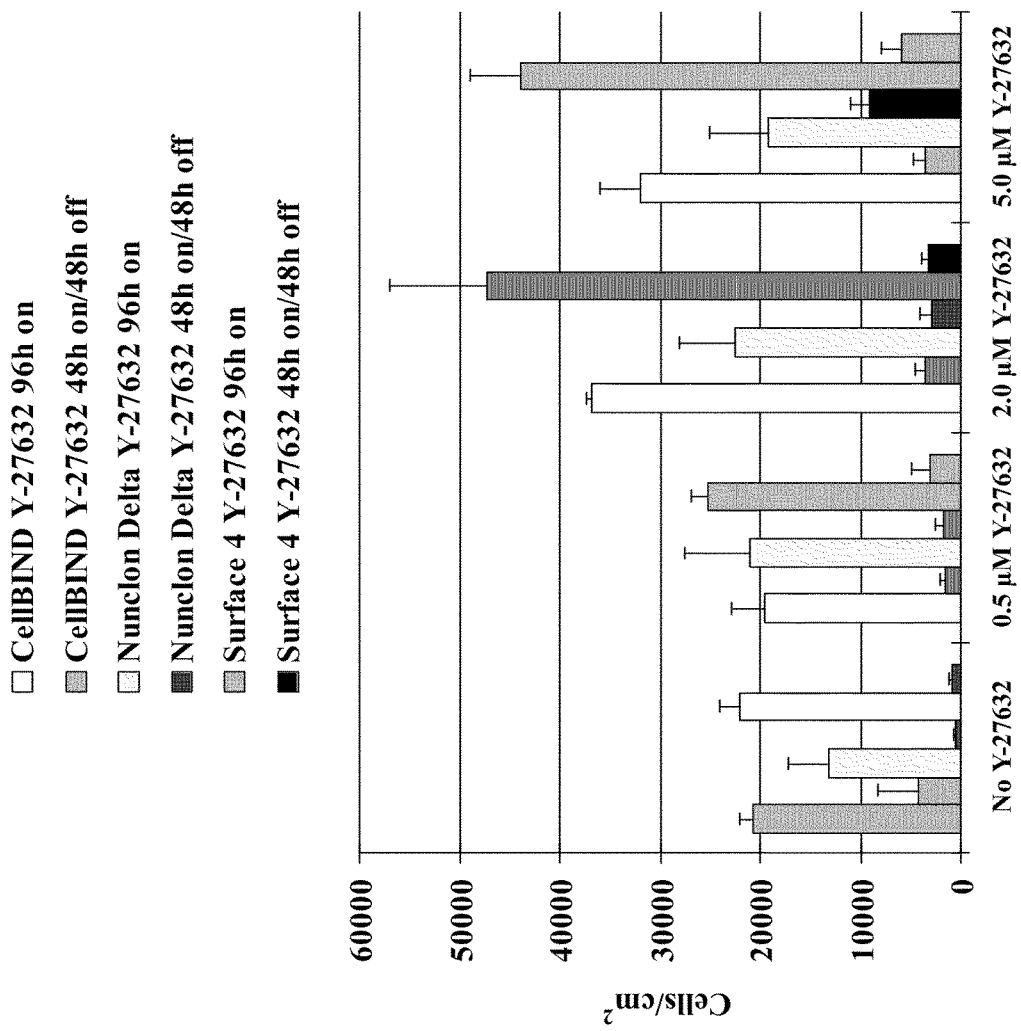
FIG. 31 shows the effect of solid substrate surfaces and Y-27632 on attachment and growth of HEK293 cells in chemically defined, serum-free Pro293a-CDM™ medium (A) or EMEM medium supplemented with 10% fetal bovine serum (B). HEK293 cells were seeded in 96-well plates with CellBIND™ surface, Nuclon Delta™ surface or Surface 4. The number of HEK293 cells attached to these surfaces is shown as a function of culture conditions and concentration of Y-27632. Cells received either: (i) 96 hours of constant treatment in culture with Y-27632 (Y-27632 96 h on); or (ii) 48 hours of constant treatment in culture with Y-27632 followed by a change of medium and then 48 hours in culture without Y-27632 (Y-27632 48 h on/48 h off). HEK293 cells cultured without Y-27632 in the medium (No Y-27632) were handled the same way as cells cultured with Y-27632, that is, for either 96-hours without a change of medium, or with a change of medium after 48 hours. Y-27632 enhanced attachment of HEK293 cells on Surface 4 and the CellBIND™ surface when applied at concentrations of 2.0 and 5.0 µM. Removing Y-27632 after 48 hours of incubation resulted in detachment of a significant number of cells from Surface 4 and the CellBIND™ surface. Mean and standard deviation of three measurements are shown.

The effect of the solid substrate surfaces and Y-27632 on attachment and growth of HEK293 cells in Pro293a-CDM medium is shown in FIG. 31a, where the 96-hour continuous exposure to Y-27632 is labeled "Y-27632 96 h on" and the 48-hour continuous exposure to Y-27632 followed by a change of medium and 48 hours of incubation in the absence of Y-27632 is labeled "Y-27632 48 h on/48 h off". In the absence of Y-27632, HEK293 cells attached to all three surfaces. A change of medium after 48 hours of incubation resulted in significantly fewer cells in the cultures, measured after 96 hours of incubation. Y-27632 enhanced attachment of HEK293 cells on Surface 4 and CellBIND™ surface when applied at concentrations of 2.0 and 5.0 µM. Removing Y-27632 after 48 hours of incubation resulted in significant detachment of cells from all three surfaces.

Figure 31B:
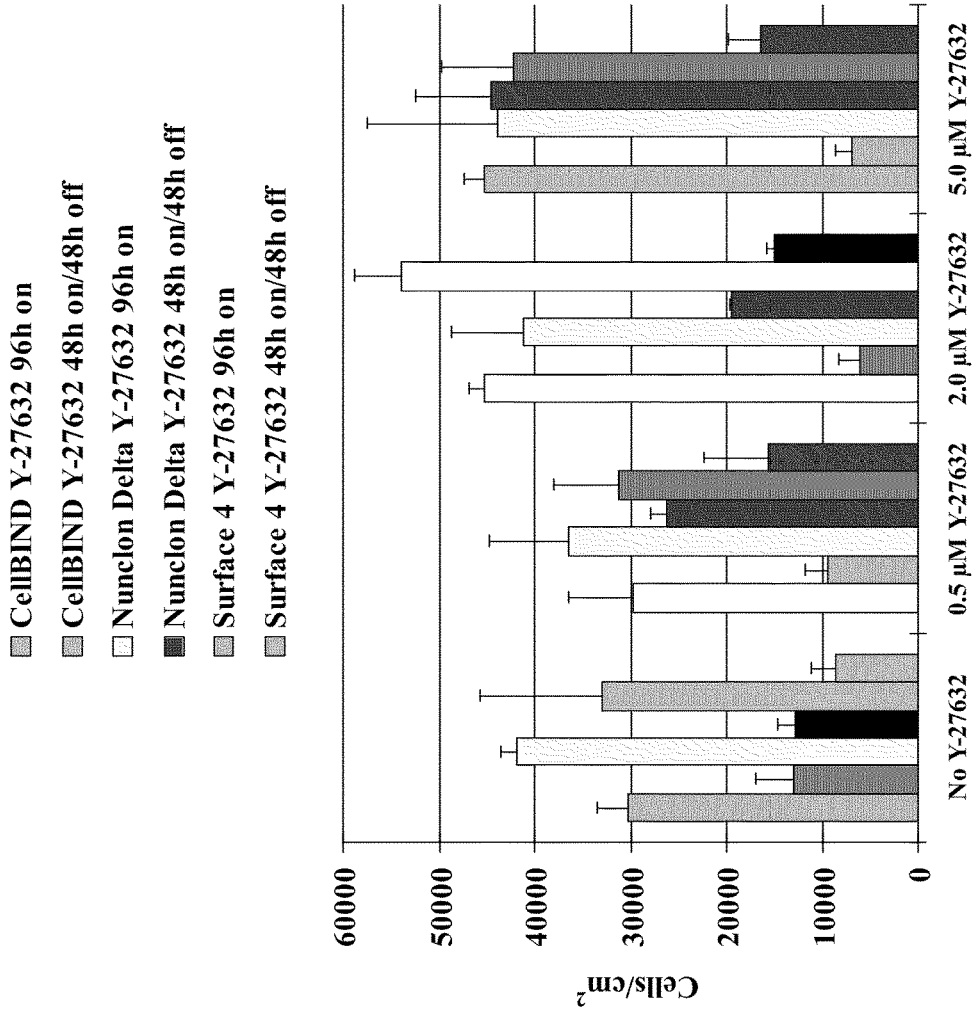

A similar experiment, but using $2.0 \times 10^4$ non-adapted HEK293 cells per $cm^2$ and EMEM supplemented with 10% FBS throughout, was performed. The effect of the solid substrate surfaces and Y-27632 on attachment and growth of HEK293 cells in EMEM supplemented with 10% FBS is shown in FIG. 31b, where the 96-hour continuous exposure to Y-27632 is labeled "Y-27632 96 h on" and the 48-hour continuous exposure to Y-27632 followed by a change of medium and 48 hours of incubation in the absence of Y-27632 is labeled "Y-27632 48 h on/48 h off". In the absence of Y-27632, HEK293 cells attached to all three surfaces. A change of medium after 48 hours of incubation resulted in significantly fewer cells in the cultures, measured after 96 hours of incubation. Y-27632 enhanced attachment of HEK293 cells on Surface 4 and CellBIND™ surface when applied at concentrations of 2.0 and 5.0 µM. Removing Y-27632 after 48 hours of incubation resulted in significant detachment of cells from Surface 4 and CellBIND™.

Example 20

Treatment with Y-27632 and H-1152 Enhance HEK293 Cell Growth on Surface Modified Plates HEK293 cells were maintained in EMEM (Lonza) containing 10% FBS (Lonza). Cells were passaged at 70-80% confluence using Trypsin/EDTA for dissociation, and seeded at c $2.0 \times 10^4$ cells/$cm^2$ in 75-$cm^2$ flasks with Nunclon Delta™ surface (Thermo Fisher Scientific, Roskilde, Denmark).

EMEM (500 µl) supplemented with 10% FBS containing 1.0, 5.0, 10, 15 or 20 µM Y-27632 (Sigma Chemical Co.), or 0.4, 1.2, 1.6, 2.4 or 2.8 µM H-1152 (Calbiochem, EMD Chemicals Inc., Darmstadt, Germany) was dispensed in Multidish 24-well plates with either Surface 4 or a non-treated (but gamma irradiated; 25 kGy) polystyrene surface. Another 500 µl of EMEM supplemented with 10% FBS and containing HEK293 cells were added to the wells ($2.0 \times 10^4$ cells/$cm^2$). The cultures were placed in an IncuCyte™ Plus (Essen Instruments, Michigan, USA) and incubated at 37° C. in a humidified atmosphere of 5% $CO_2$ in air. The IncuCyte™ Plus is an automated imaging platform, configured to fit inside a $CO_2$ incubator, and designed to provide kinetic, non-invasive live cell imaging by acquiring phase contrast images of the cells at user-defined times and locations within the cultures. The primary metric of the instrument is culture confluence, that is, the fraction of the surface that is covered by cells. The HEK293 cells were incubated for 72 hours without manipulations, and images were collected every two hours at 9 positions in triplicate cultures. Culture confluence was determined using the IncuCyte™ Plus software (v. 3.4.1.25966).

Figure 32A:
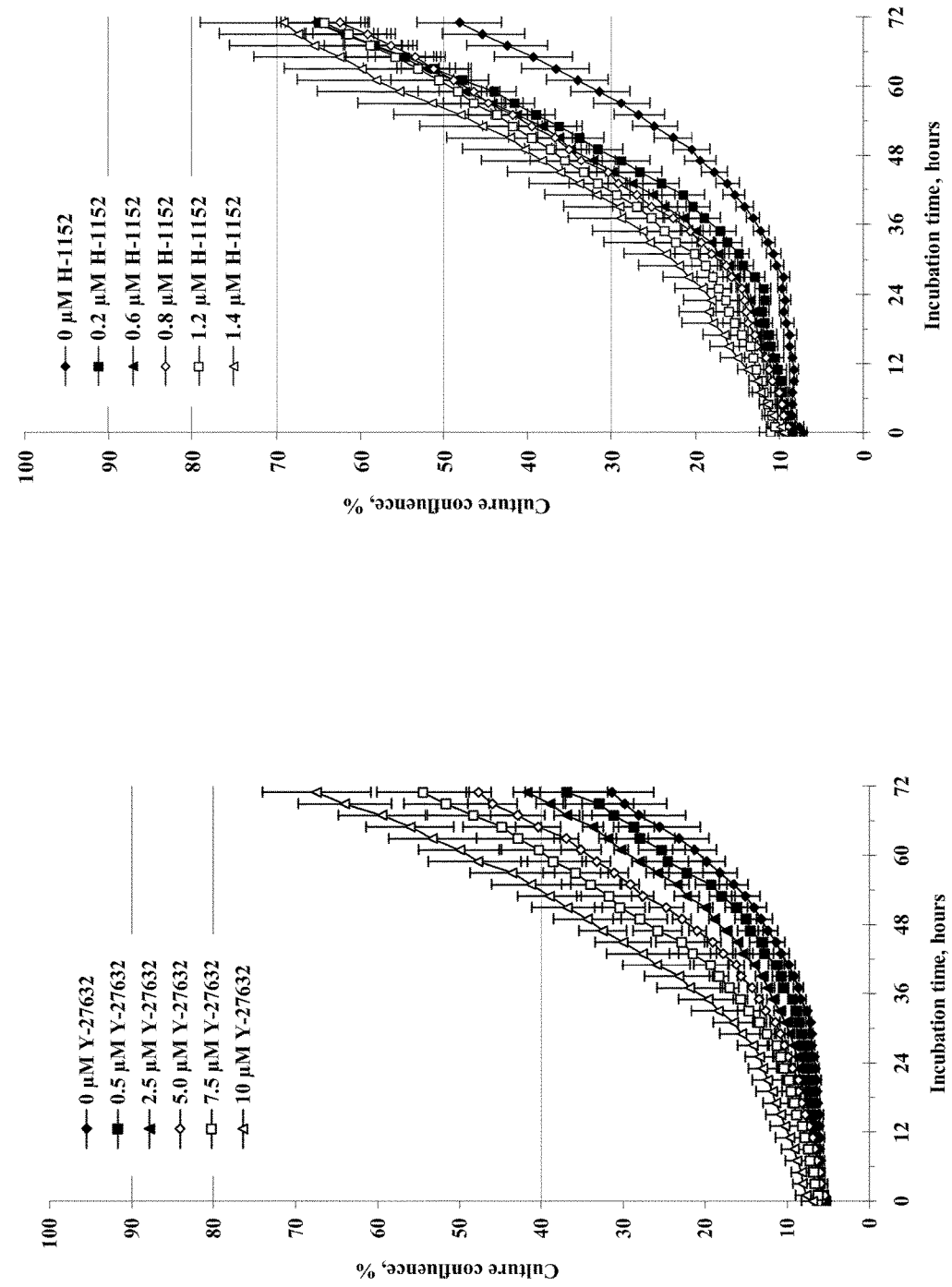
FIG. 32 shows the effect of solid substrate surfaces and Rho kinase inhibitors Y-27632 and H-1152 on growth of HEK293 cells in EMEM medium supplemented with 10% fetal bovine serum. HEK293 cells were seeded in Multidish 24-well plates with either Surface 4 (A) or a non-treated (but gamma irradiated; 25 kGy) polystyrene surface (B).
Figure 32B:
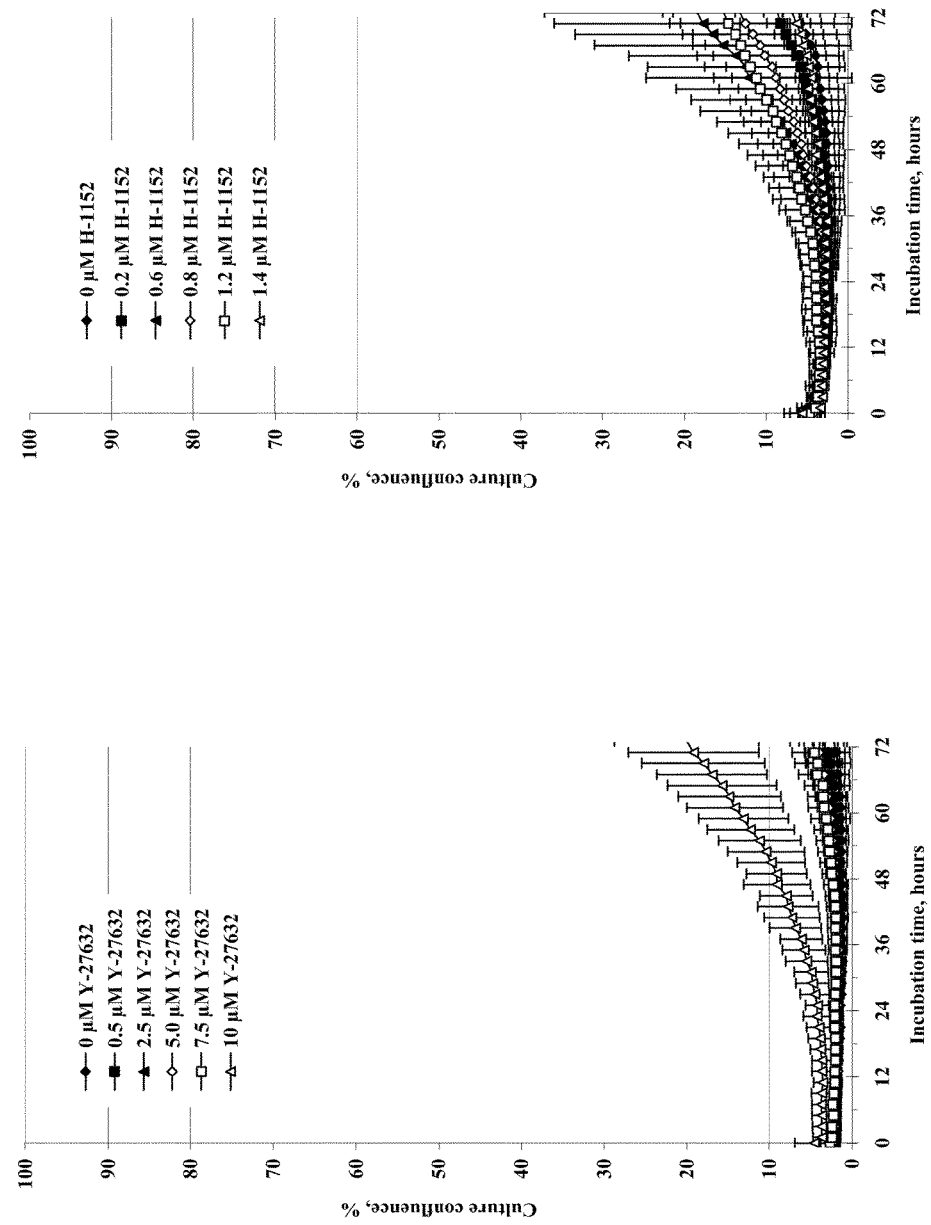

Increasing concentration of Y-27632 and H-1152 enhances attachment and growth of HEK293 cells on Surface 4 (FIG. 32a). The effect of a non-treated cell culture surface and Y-27632 or H-1152 on attachment and growth of HEK293 is shown in (FIG. 32b). Growth and attachment of HEK293 cells was slightly enhanced in the presence of 10 µM Y-27632 and 0.6-1.2 µM H-1152. However, the enhancement of growth and attachment of HEK293 cells on a non-treated cell culture surface is insignificant in comparison to Surface 4.

Example 21

Treatment with H-1152 Enhances HEK293 Cell Growth and Attachment to Surface Modified Plates HEK293 cells were maintained in EMEM (Lonza) containing 10% FBS (Lonza). Cells were passaged at 70-80% confluence using Trypsin/EDTA for dissociation, and seeded at c $2.0 \times 10^4$ cells/$cm^2$ in 75-$cm^2$ flasks with Nunclon Delta™ surface (Thermo Fisher Scientific, Roskilde, Denmark).

EMEM (1.0 ml) supplemented with 10% FBS containing 0.4, 0.8, 1.2, 1.6, 2.0, 2.4 or 2.8 µM H-1152 was dispensed in Multidish 12-well plates with Surface 4. Another 1.0 ml of EMEM supplemented with 10% FBS and containing HEK293 cells were added to the wells ($4.0 \times 10^4$ cells/$cm^2$). The cultures were placed in an IncuCyte™ Plus, and incubated at 37° C. in a humidified atmosphere of 5% $CO_2$ in air for 42 hours (images were collected every 6 hours). One ml of culture medium was then removed by pipetting, and 1.0 ml EMEM supplemented with 10% FBS containing 0.2, 0.4, 0.6, 0.8, 1.0, 1.2 and 1.4 µM H-1152 was added. The cultures were placed in the IncuCyte™ Plus again, and images were collected every hour over the following 25 hours. Images were collected at 9 positions in triplicate cultures, and culture confluence was determined using the IncuCyte™ Plus software. Images from the IncuCyte™ Plus collected at specific positions in HEK293 cell cultures grown in the absence or presence of H-1152 (0.6 µM) was retrieved and presented as phase-contrast micrographs for the comparison of HEK293 culture morphology at the following time points: start of incubation (0 hours), just before medium change (42 hours), 1 hour after the medium change (43 hours), and, finally, after 52 hours of incubation.

In the absence of H-1152 and in the presence of 0.2 µM or 0.4 µM H-1152, the change of 50% of the medium after 42 hours of incubation resulted in a significant reduction in culture confluence (FIG. 33a). In the presence of 0.6 µM, 0.8 µM or 1.4 µM H-1152, the effect of changing the medium was minimal. HEK293 cells grown on Surface 4 in the presence of H-1152 covered the solid substrate surfaces more evenly than HEK293 cells grown on Surface 4 in the absence of H-1152 (FIG. 33b). In the absence of H-1152, HEK293 cells formed large clusters, whereas, HEK293 cells in the presence of H-1152 formed smaller clusters with lower cell density.

Example 22

Figure 34:
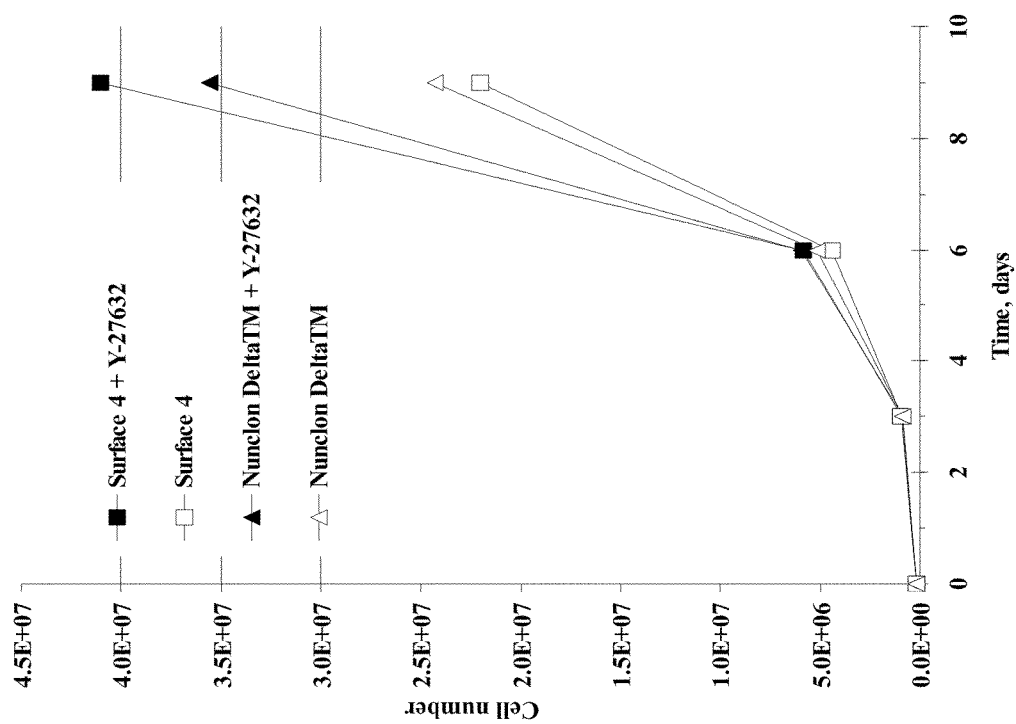
FIG. 34 shows growth curves over 3 passages for HEK293 cells grown on surface 4 and Nunclon Delta™ surface in the absence or presence of 2.5 µM Y-27632. HEK293 cells in EMEM medium supplemented with 10% fetal bovine serum were passaged 3 times by trypsinization.

Treatment with Y-27632 Enhances HEK293 Cell Growth Over Three Passages on Surface Modified Plates EMEM (500 µl) supplemented with 10% FBS containing 5.0 µM Y-27632 was dispensed in wells of Multidish 24-well plates with Surface 4 or Nunclon Delta™ surface. Another 500 µl of EMEM supplemented with 10% FBS and containing HEK293 cells was added to the wells ($2.0 \times 10^4$ cells/$cm^2$), and the cultures were incubated at 37° C. in a humidified atmosphere of 5% $CO_2$ in air for 3 days. Cells were passaged by treatment with Trypsin/EDTA (Lonza, Verviers, Belgium) for two minutes at 37° C., and the total cell number was determined using a NucleoCount Cell Counter (Chemometec A/S, Allerød, Denmark). For successive passages, HEK293 cells were seeded at $2.0 \times 10^4$ cells/$cm^2$. The growth of HEK293 cells on Surface 4 and Nunclon Delta™ surface was enhanced by the presence of 2.5 µM Y-27632 (FIG. 34).

Example 23

Attachment, Cultivation and Maintenance of Human Embryonic Stem Cells Using Surface Modified Plates 4, 18, and 19 that Lack Extracellular Matrix Protein/Components and Feeder Cells Passage 42 H1 hES cells maintained on 1:30 MATRIGEL coated plasticware in MEF conditioned media supplemented with 8 ng/ml of bFGF were lifted by LIBERASE™ enzymatic treatment and plated to surface modified 96 well format plates at a 1 to 2 dilution in MEF conditioned media supplemented with 8 ng/ml of bFGF. The cells were plated to modified surfaces 4, 18, or 19, or Primaria™. In order to determine the effect of Rho Kinase inhibition on binding to the modified surface we treated the cells with either 10 µM of the Rho Kinase inhibitor Y-27632, or 3 or 10M of the Rho Kinase inhibitor H-1152glycyl. Untreated cells served as controls. After 24 hours in culture the wells were aspirated, the cells were dried, and the wells were stained with Crystal violet.

Figure 35:
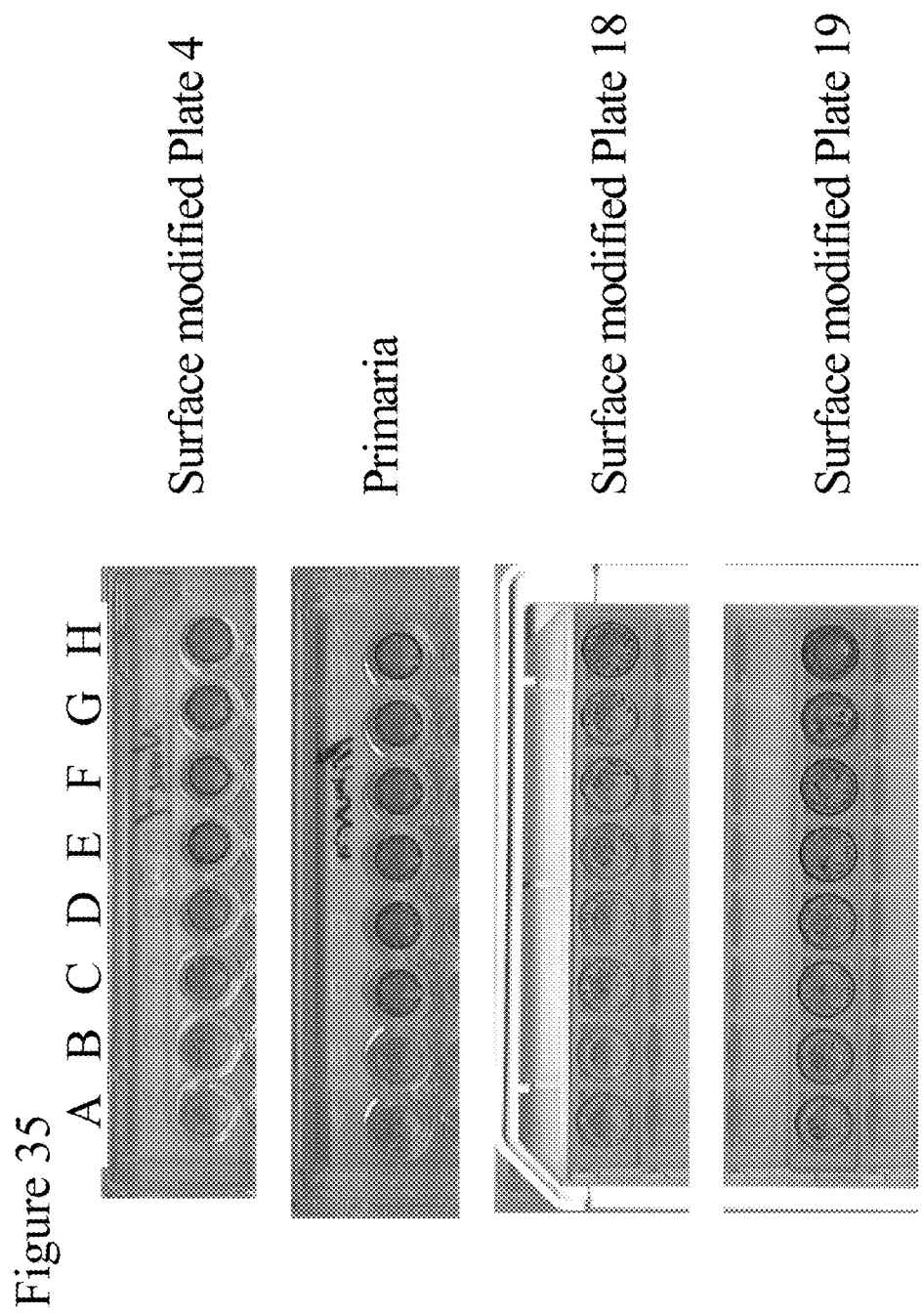
FIG. 35 shows the effect of Rho kinase inhibition on the attachment of cells of the human embryonic stem cell line H1 to surface modified plates 4, 18 and 19, and Primaria™. Wells A&B were control wells on all surfaces. Wells C&D contained 10 µM Y-27632. Wells E&F contained 3 µM H1152-glycyl. Wells G&H contained 10 µM H1152-glycyl.
Figure 36:
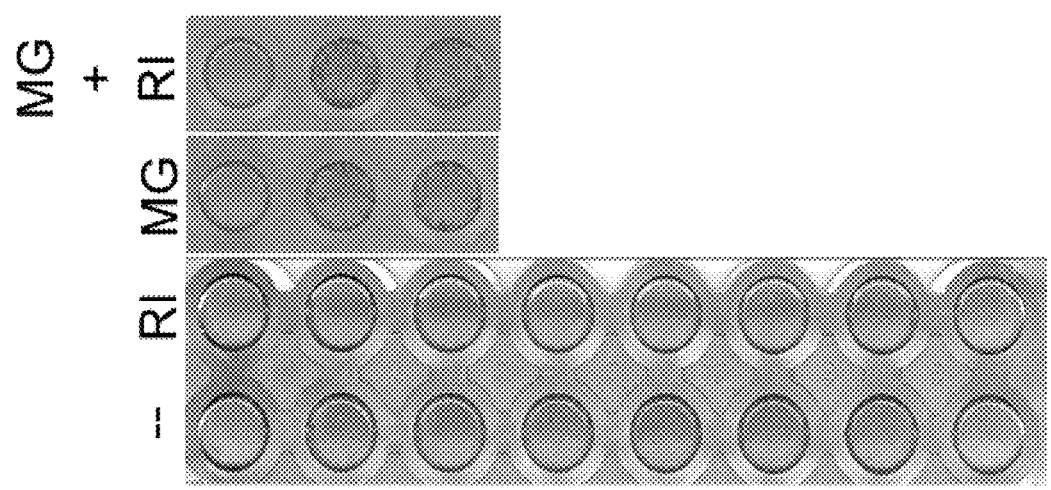
FIG. 36 shows the effect of Rho kinase inhibition on the attachment of cells of the human embryonic stem cell line H1 to surface modified plate 30. (--)=no treatment. (RI)=3 µM H1152-glycyl. (MG)=adlayer of 1:30 dilution of MATRIGEL. (MG+RI)=adlayer of 1:30 dilution of MATRIGEL+3 µM H1152-glycyl.
Figure 37:
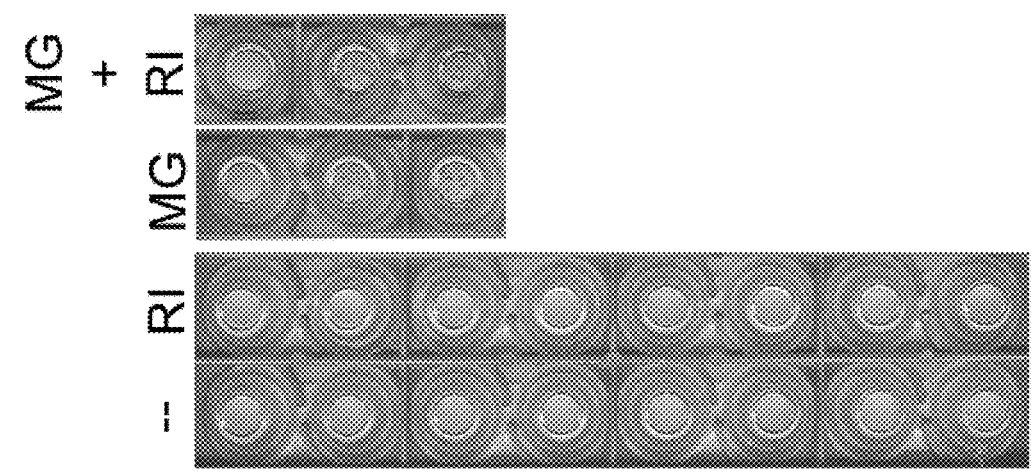
FIG. 37 shows the effect of Rho kinase inhibition on the attachment of cells of the human embryonic stem cell line H1 to surface modified plate 31. (--)=no treatment. (RI)=3 µM H1152-glycyl. (MG)=adlayer of 1:30 dilution of MATRIGEL. (MG+RI)=adlayer of 1:30 dilution of MATRIGEL+3 µM H1152-glycyl.
Figure 38:
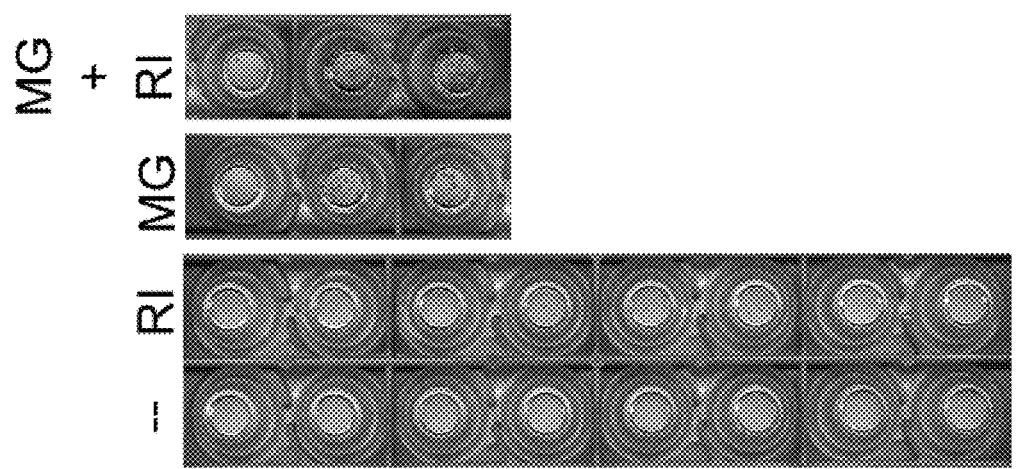
FIG. 38 shows the effect of Rho kinase inhibition on the attachment of cells of the human embryonic stem cell line H1 to surface modified plate 32. (--)=no treatment. (RI)=3 µM H1152-glycyl. (MG)=adlayer of 1:30 dilution of MATRIGEL. (MG+RI)=adlayer of 1:30 dilution of MATRIGEL+3 µM H1152-glycyl.
Figure 39:
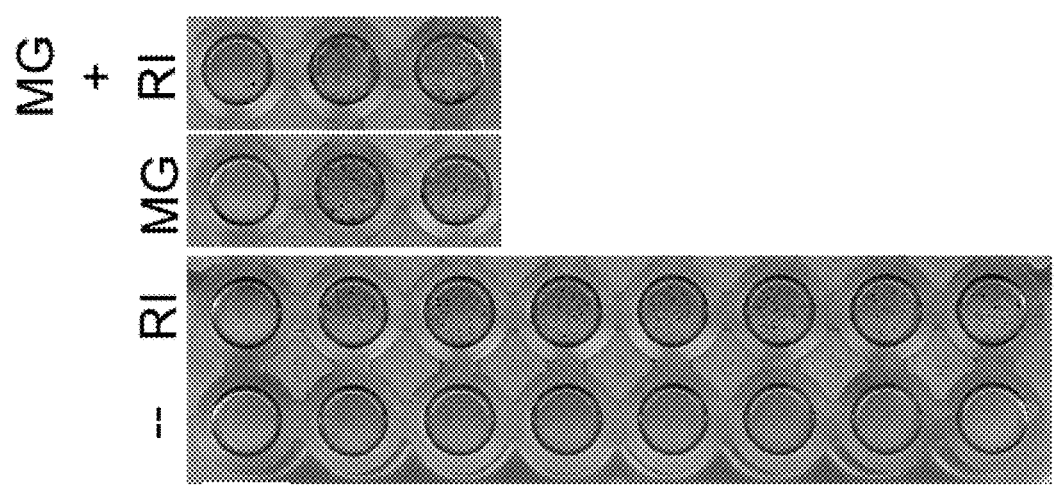
FIG. 39 shows the effect of Rho kinase inhibition on the attachment of cells of the human embryonic stem cell line H1 to surface modified plate 33. (--)=no treatment. (RI)=3 µM H1152-glycyl. (MG)=adlayer of 1:30 dilution of MATRIGEL. (MG+RI)=adlayer of 1:30 dilution of MATRIGEL+3 µM H1152-glycyl.
Figure 40:
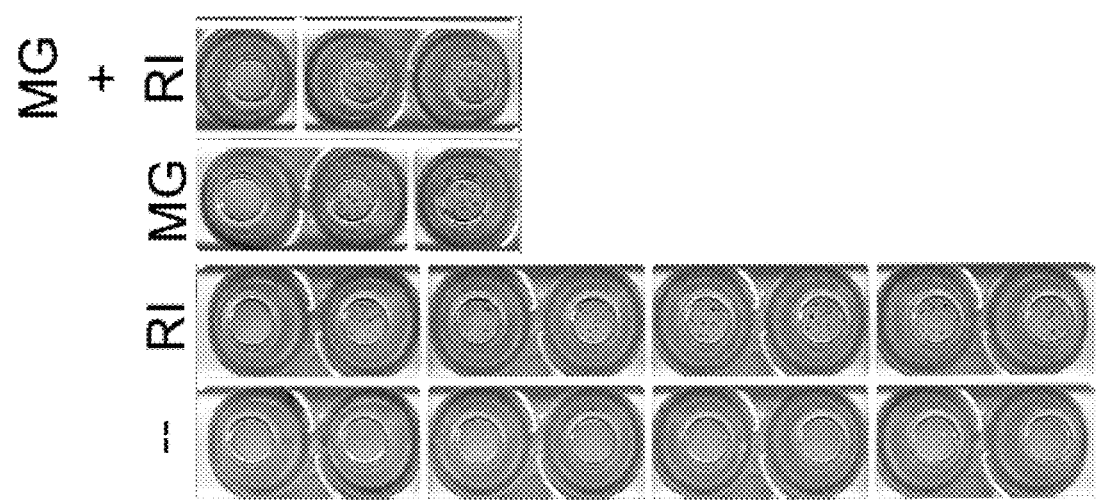
FIG. 40 shows the effect of Rho kinase inhibition on the attachment of cells of the human embryonic stem cell line H1 to surface modified plate 34. (--)=no treatment. (RI)=3 µM H1152-glycyl. (MG)=adlayer of 1:30 dilution of MATRIGEL. (MG+RI)=adlayer of 1:30 dilution of MATRIGEL+3 µM H1152-glycyl.

We observed that after 24 hours in culture, ES cell colonies had attached and spread when treated with Rho Kinase inhibitors on surface modified plates 4 and 19 and the Primaria™ plate, however the same effect was not observed on surface modified plate 18 (FIG. 35).

Example 24

Attachment, Cultivation and Maintenance of Human Embryonic Stem Cells Using Surface Modified Plates 30, 31, 32, 33, and 34 that Lack Extracellular Matrix Protein/Components and Feeder Cells Passage 47 H1 hES cells maintained on 1:30 MATRIGEL coated plasticware in MEF conditioned media supplemented with 8 ng/ml of bFGF were lifted by TrypLE™ enzymatic treatment and plated to surface modified 96 well format plates at a 1 to 3 dilution in MEF conditioned media supplemented with 8 ng/ml of bFGF. The cells were plated to modified surfaces 30, 31, 32, 33, or 34. In order to determine the effect of Rho Kinase inhibition on binding to the modified surface we treated the cells with 3 µM of the Rho Kinase inhibitor H-1152glycyl. Untreated cells served as controls. Additionally, cells were seeded to wells in the surface modified plate that were pre-treated with Matrigel™. 24 hours after plating the media was changed with fresh MEF conditioned media supplemented with 8 ng/ml of bFGF, and for cells seeded in the presence of the Rho Kinase inhibitor the media was supplemented with 3 µM H-1152glycyl. After 48 hours in culture the wells were aspirated, the cells were dried, and the wells stained with Crystal violet.

We observed that after 48 hours in culture, ES cell colonies had attached and spread when treated with Rho Kinase inhibitors on surface modified plates 33 and 34 (FIGS. 39 and 40 respectively), however the same effect was not observed on surface modified plates 30, 31 or 32 (FIGS. 36-40 respectively).

Example 25

Attachment, Cultivation and Maintenance of Human Embryonic Stem Cells Using Surface Modified Plates 22, 23, 24 or 29 that Lack Extracellular Matrix Protein/Components and Feeder Cells Passage 46 H1 hES cells maintained on 1:30 MATRIGEL coated plasticware in MEF conditioned media supplemented with 8 ng/ml of bFGF were lifted by Liberase™ enzymatic treatment and plated to surface modified 60 mm dishes at a 1 to 3 dilution in MEF conditioned media supplemented with 8 ng/ml of bFGF. The cells were plated to surface modified plates 3, 4, 22, 23, 24 and 29. In order to determine the effect of Rho Kinase inhibition on binding to the modified surface we treated the cells with 3 µM of the Rho Kinase inhibitor H-1152glycyl to plate the cells. The media was changed with fresh MEF conditioned media supplemented with 8 ng/ml of bFGF and 1 µM of the Rho Kinase inhibitor H-1152glycyl 24 hours after plating the cells. Cells seeded to modified surface 3, 4 or Matrigel™ coated plastic served as controls. The plates were observed by phase microscopy 24 and 48 hours after plating. We observed that after 48 hours in culture, ES cell colonies had not attached to surface modified plates 22, 23, 24 or 29 plated with or without Rho Kinase inhibitor, while cells plated to surface modified plate 3 or 4 in the presence of Rho Kinase inhibitor did attach and spread.

Example 26

Figure 41:
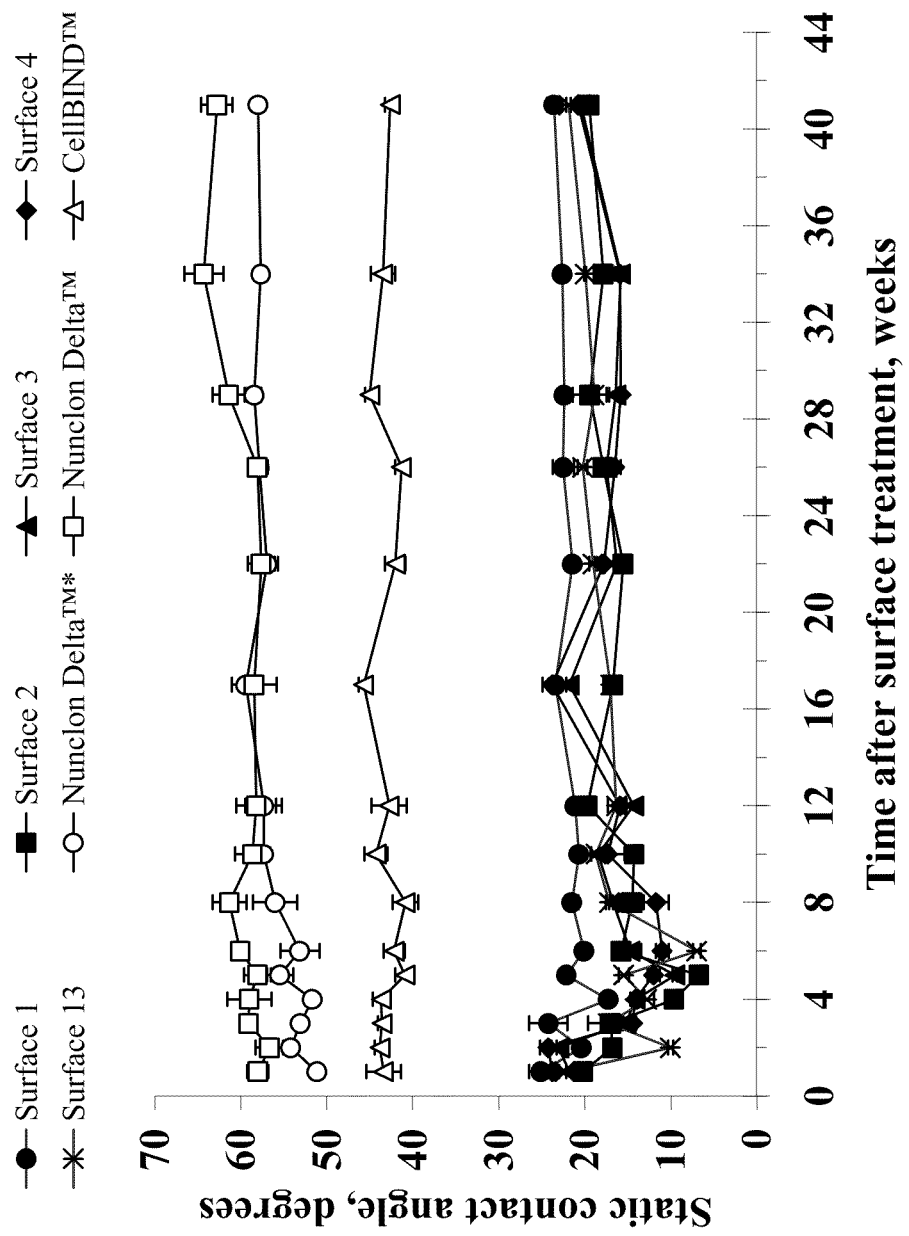
FIG. 41 shows the water contact angles of surface modified plates measured over 40 weeks using the static sessile drop method.

Further Surface Characterization of the Surface Modified Plates of the Present Invention Water Contact Angles Surface modified plates 1-4 and 13 were individually packed in plastic bags, sterilized, and stored at room temperature throughout a 40-week test period. Contact angles were first measured one week after surface treatment and sterilization, and then again at the time points given in FIG. 41. All contact angle measurements were done as described in Example 17. Measurements on Nunclon Delta™ and CellBIND™ surfaces was performed under the same experimental conditions as measurements on Surface 1-4 and 13, but the surface treatment and sterilization was done more than 12 weeks before the first measurement (Nuclon Delta™* was sterilized one week before the first measurement). FIG. 41 shows that surface modified plates 1-4 and 13 were of similar hydrophilicity and more hydrophilic (lower water contact angles) than Nunclon Delta™ and CellBIND™ surfaces. The hydrophilicity of surface modified plates 1-4 and 13 was stable for at least 41 weeks after surface treatment and sterilization.

Figure 42:
FIG. 42 shows the water contact angles of surface modified plates using the static sessile drop method.

Contact angles were also measured on surface modified plates 5-12, 22-24, 29, 30 and 33, which were packed in plastic bags, sterilized as described in Example 16, and stored at room temperature for 9 weeks (except for surface modified plate 29 which was stored for 28 weeks). Surface modified plates 18, 19, 32 and 34 were in single-microwell format and could, therefore, not be used for measurements of contact angles. Surface modified plates 30 and 33 were in a microwell plate format, and contact angle measurements were performed on the backside of the plate and not inside wells. Contact angles were measured as described in Example 17 (for the highly hydrophilic surface modified plate 29, a smaller drop of 2.5 µl MilliQ water was applied), but triplicate samples were analysed, with 7 drops being applied per sample. Measurements on plates with Costar™, Falcon™, Primaria™ and Nunclon Delta™ surfaces was performed under the same experimental conditions, but the surface treatment and sterilization was done more than 12 weeks before the first measurement. FIG. 42 shows that surface modified plates 5-12 were more hydrophilic (lower water contact angles) than Nunclon Delta™, Costar™ and Falcon™ surfaces. The hydrophilicity of surfaces 5-12 was comparable to the hydrophilicity of the Primaria™ surface, and higher than the hydrophilicity of surfaces 1-4 and 13 (shown in FIG. 41). The hydrophilicity of surface modified plates 22-24 and 33 was comparable to the hydrophilicity of surfaces 1-4 and 13 (shown in FIG. 41), whereas the hydrophilicity of surface 30 was comparable to the hydrophilicity of Nunclon Delta™, Costar™ and Falcon™ surfaces. Surface modified plate 29 was significantly more hydrophilic than the other surfaces analysed.

Negative Charge Density

The density of negative charges on surface modified plates 5-12 (all 5-cm dish format), 18, 19, 30, 32, 33 and 34 (all microwell format), surface modified plates 22-24 and 29 (all 6-cm dish format), and CellBIND™ surface (3-cm dish format), Primaria™ surface (multidish-6 format) and Nunclon Delta™ surface (3-cm dish format) was determined. Aqueous crystal violet solution (0.015% w/v) in excess was added to each format (0.34 ml/cm$^2$ for dish format and 0.13 ml/cm$^2$ for microwell format), and was incubated for 60 minutes at room temperature under gentle shaking (50 rpm). In order to remove crystal violet not bound to the surfaces, the dishes were washed three times with 3 ml MilliQ water for the dish formats and three times with 350 µl MilliQ water for microwell formats, and then dryed over night at 60° C. The crystal violet bound to the surface was desorbed by addition of 0.17 ml/cm$^2$ of 0.1 M HCl in EtOH solution (99%) and incubating the dishes for 2 minutes at room temperature under gentle shaking (50 rpm). Absorbance of the HCl:EtOH solution with desorbed crystal violet was measured at 590 nm using an EnVision 2100 microplate reader (Perkin Elmer; Waltham, Mass., USA). Absorbance values were corrected for background absorbance of HCl:EtOH solution. The negative charge density was measured on three dishes with surface modified plates 5-12, 22-24, 29, CellBIND™, Primaria™ and Nunclon Delta™, and absorbance measurements were performed in triplicate for each dish. For surface modified plates 18, 19, 30, 32, 33 and 34, one sample was tested with triplicate measurements.

Figure 43:
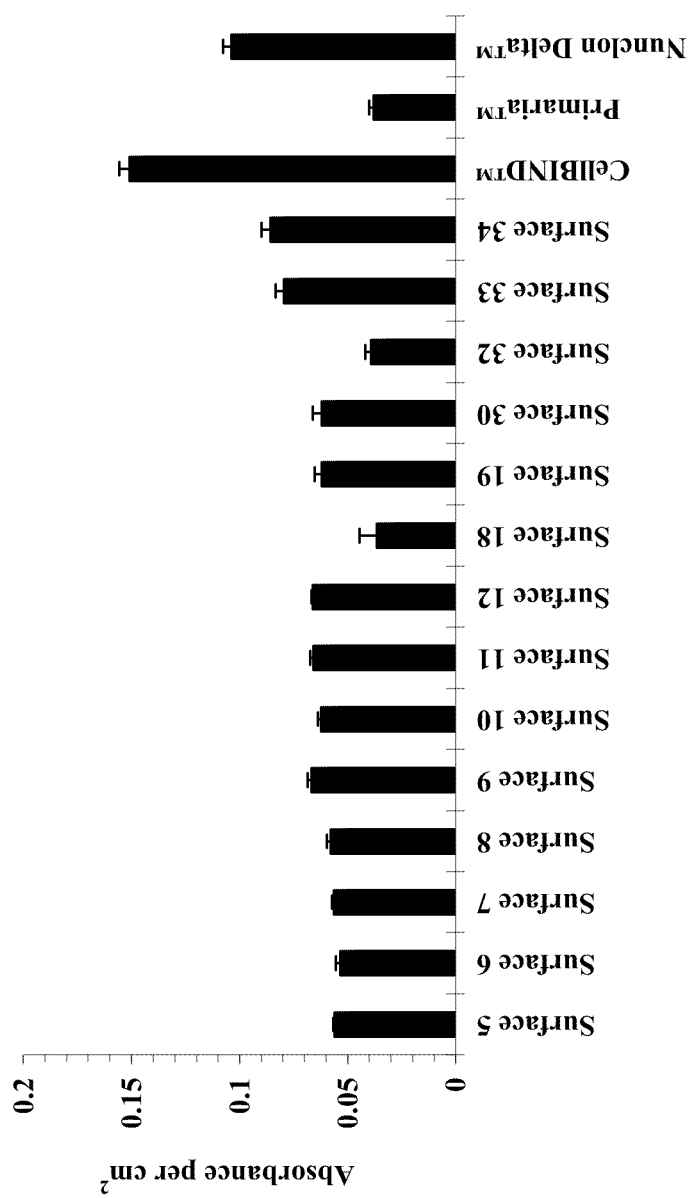
FIG. 43 shows the density of negative charges on surface modified plates measured as reactivity of surfaces with positively charged crystal violet.
Figure 44:
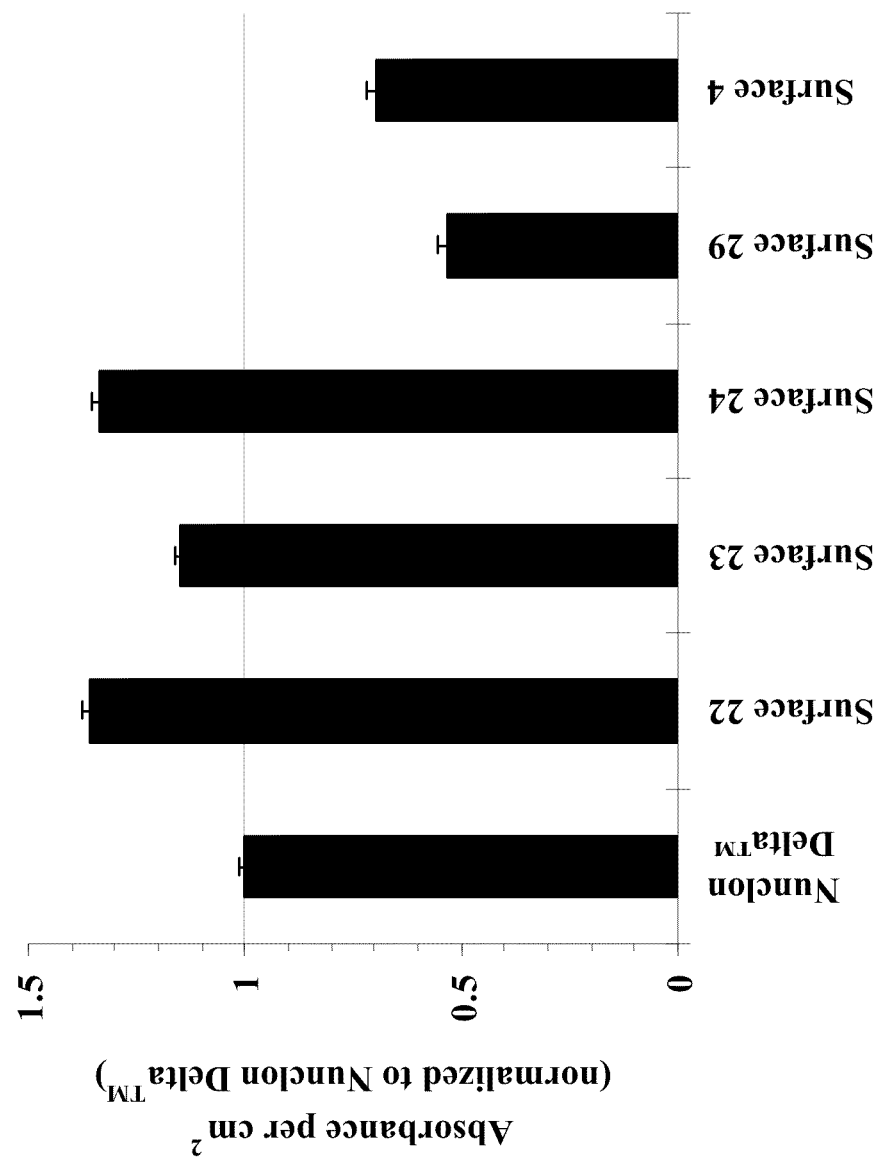
FIG. 44 shows the density of negative charges on surface modified plates 4, 22-24 and 29 measured as reactivity of surfaces with positively charged crystal violet. Three samples of each surface were tested, and absorbance measurements on desorbed crystal violet from each sample were performed in triplicate. The negative charge density for surfaces 4, 22-24 and 29 was normalized to the negative charge density of the Nunclon Delta™ surface. Mean and standard deviation of nine measurements are given.

The negative charge densities of surface modified plates 5-12 were similar, and these surfaces had significantly lower negative charge densities than CellBIND™ surface and Nunclon Delta™ surface, but significantly higher negative charge densities than the Primaria™ surface (FIG. 43). The negative charge densities of surface modified plates 19, 33 and 34 were significantly higher than the negative charge densities of surface modified plates 18, 30 and 32, the latter being the respective non-treated surfaces in the same polymer material. The negative charge densities of surface modified plates 22-24 and 29 were normalized to the negative charge density of the Nunclon Delta™ surface, and FIG. 44 shows that surface modified plates 22-24 had higher negative charge densities than the Nunclon Delta™ surface, whereas the negative charge density for surface modified plate 29 was significantly lower than the negative charge density of the Nunclon Delta™ surface (and surface 4).

X-Ray Photoelectron Spectroscopy (XPS)

Surface modified plates 5-12, 18, 19, 22-24, 29, 30, 31-34 were analyzed using XPS as described in Example 17. Surface elemental composition in units of atomic percent is shown in Table 12. All surfaces contained carbon, oxygen and nitrogen (hydrogen is not detected in XPS), except surface modified plates 31 and 32 (not plasma treated), which did not contain nitrogen. Surface modified plates 5-12 contained less oxygen than surface modified plates 1-4 and 13, but significantly more oxygen than Costar™, Falcon™ and Nunclon Delta™ surfaces (shown in Table 7). Surface modified plates 5-12, were prepared by microwave plasma treatment while surface modified plates 1-4 and 13 were produced by corona plasma treatment. Surface modified plates 19, 33 and 34, which were prepared by Corona plasma treatment, but injection molded from other polymers than polystyrene (which was used in the preparation of surface modified plates 1-4 and 13), contained oxygen levels comparable to those of surface modified plates 1-4 and 13. Surface modified plates 22-24 contained less oxygen than surface modified plates 1-4 and 13. Surface modified plate 29 contained oxygen at a level comparable to surface modified plates 1-4 and 13. Surface modified plates 5-12, 19, 33 and 34 contained less nitrogen than surface modified plates 1-4 and 13, but more nitrogen than Costar™, Falcon™ and Nunclon Delta™ surfaces (shown in Table 7). Surface modified plate 29 contained significantly more nitrogen than the other surfaces analysed, including the Primaria™ surface.

C1s spectra peaks were curve fit (best chi-squared fit), in order to identify and quantify the bonding environments for carbon in the surface modified plates, by using peak widths and energy locations for species as found in the literature (Table 13). The concentrations are reported in units of atomic percent, which were obtained by multiplying the area percent by the atomic concentration. All plasma-treated surfaces, except surfaces 10, 22-24 and 29, were similar in terms of the carbon bonding environments. The proportion of carbon in C—[O]—C was significantly higher in Surfaces 19, 33 and 34 than in surfaces 5-12, 18, 30 and 32 and surfaces 1-4 and 13 (shown in Table 8). The proportion of carbon in O—[C=O]—O bonding environment was lower in surfaces 5-12, 19, 33 and 34 than in surfaces 1-4 and 13. The proportion of carbon in C*—C—O—C—C* was significantly higher in surfaces 5-9, 11, 12, 19, 33 and 34 than in surfaces 1-4 and 13, but comparable to Nunclon Delta™ and CellBIND™ surfaces. The proportion of carbon in C—O—C or C—NH$_3^+$ bonding environment (same energy location in spectra) was lower in surfaces 5-12, 19, 33 and 34 than in surfaces 1-4 and 13, but was higher than in Costar™, Falcon™, CellBIND™ and Primaria™ surfaces. The proportion of carbon in C—O—C*=O bonding environment was higher in surfaces 19, 33 and 34 than in surfaces 5-12, and comparable to the level in surfaces 1-4 and 13. The proportion of carbon in C=O bonding environment was higher in surfaces 5-12 than in surfaces 19, 33 and 34, but lower than in surfaces 1-4 and 13. The proportion of carbon in CO$_3^-$ bonding environment was higher in surfaces 5-12 than in surfaces 19, 33 and 34, and comparable to the level in surfaces 1-4 and 13. Surfaces 22-24 were similar in terms of carbon bonding environments. The proportion of carbon in C—[O]—C, O—[C=O]—O, C—O—C or C—NH$_3^+$, C—O—C*=O and C=O for surfaces 22-24 was significant lower than for surfaces 1-4 and 13. The proportion of carbon in $CO_3$— and C*—C—O—C—C* bonding environments was higher for surfaces 22-24 than for surfaces 1-4 and 13. The carbon bonding environment of surface 29 was different from the carbon bonding environment of all other plasma-treated surfaces. The proportion of carbon in C—[O]—C was comparable to surfaces 1-4 and 13. The proportions of carbon in O—[C=O]—O, $CO_3^-$ and C*—C—O—C—C* bonding environments were lower for surface 29 than for surfaces 1-4 and 13. The proportions of carbon in C—O—C or C—$NH_3^+$, C—O—C*=O and C=O bonding environments were higher for surface 29 than for surfaces 1-4 and 13. The energy loss peak resulted from an aromatic π→π* transition, and is an indicator of surface aromaticity.

The O1s spectra peaks were almost Gaussian and could not be curve fit. N1s spectra peaks were curve fit (best chi-squared fit), in order to identify and quantify the bonding environments for nitrogen in the surfaces, by using peak widths and energy locations for species as found in the literature (Table 14). The concentrations are reported in units of atomic percent, which were obtained by multiplying the area percent by the atomic concentration. The proportion of nitrogen in —$NH_3^+$ bonding environment in all surfaces, except surface 9, was lower than in surfaces 1-4 and 13. Nitrogen in —$NH_2$ bonding environment in surfaces 5-12, 19, 33 and 34 varied, but was higher than in surfaces 1-4 and 13. Nitrogen in —$NO_2$ bonding environment in surfaces 5-12, 19, 33 and 34 varied, but was lower than in surfaces 1-4 and 13. Nitrogen in —$NO_3$ bonding environment in surfaces 5-12, 19, 33 and 34 varied, but was higher than in surfaces 1-4 and 13. The nitrogen bonding environments of surfaces 22-24 and 29 were different from the other plasma-treated surfaces. The proportion of nitrogen in —$NH_2$ bonding environment in surfaces 22-24 and 29 varied, but was significantly higher than in surfaces 1-4 and 13. The proportion of nitrogen in —$NO_2$ bonding environment was lower in surfaces 22-24 and 29 than in surfaces 1-4 and 13. The proportion of nitrogen in O=C—N—C=O bonding environment was comparable in surfaces 22-24 and 29 and surfaces 1-4 and 13.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLES

TABLE 1

Expression of Pluripotency Markers in Cells of the Human Embryonic Stem Cell Line H1 at Passage 50, Cultured on the Surface Modified Plates of the Present Invention

| Culture Condition | Marker | | | | | | | | | |
|---|---|---|---|---|---|---|---|---|---|---|
| | CFC1 | GATA2 | GJA7 | NANOG | OCT4 | SOX2 | SOX7 | TERT | TUBB3 | ZIC1 |
| Costar 1:30 MATRIGEL | 1.0 | 1.0 | 1.0 | 1.0 | 1.0 | 1.0 | 1.0 | 1.0 | 1.0 | 1.0 |
| Surface Modified Plate 2 Gelatin | 0.3 | 0.5 | 0.8 | 0.8 | 0.4 | 0.8 | 2.1 | 0.6 | 3.2 | 1.5 |
| Surface Modified Plate 2 No Coating | 1.0 | 0.4 | 0.9 | 0.9 | 0.7 | 1.1 | 1.9 | 0.7 | 2.8 | 1.5 |
| Surface Modified Plate 2 No Coating | 0.3 | 0.5 | 0.7 | 0.7 | 0.3 | 0.6 | 0.8 | 1.0 | 3.1 | |
| Surface Modified Plate 3 Gelatin | 0.5 | 0.6 | 0.7 | 0.8 | 0.5 | 0.8 | 1.4 | 0.9 | 3.0 | 3.0 |
| Surface Modified Plate 3 No Coating | 0.3 | 0.5 | 0.7 | 0.8 | 0.5 | 0.6 | 1.9 | 1.0 | 3.9 | 0.9 |
| Surface Modified Plate 3 No Coating | 0.3 | 0.7 | 0.8 | 1.3 | 0.5 | 0.8 | 1.4 | 1.2 | | 1.0 |
| Surface Modified Plate 4 Gelatin | 0.4 | 0.4 | 0.7 | 1.0 | 0.5 | 0.9 | 1.2 | 1.0 | 3.2 | 2.9 |
| Surface Modified Plate 4 No Coating | 0.5 | 0.6 | 1.1 | 1.2 | 0.9 | 1.4 | 2.3 | 1.3 | 4.1 | 1.5 |
| Surface Modified Plate 4 No Coating | 1.0 | 0.3 | 1.8 | 1.0 | 0.8 | 1.3 | 0.8 | 0.9 | 2.1 | 1.7 |

TABLE 2

Expression of Pluripotency Markers in Cells of the Human Embryonic Stem Cell Line H1 at Passage 53 Cultured on the Surface Modified Plates of the Present Invention

| Culture Condition | MARKER | | | | | | | | | |
|---|---|---|---|---|---|---|---|---|---|---|
| | CFC1 | GATA2 | GJA7 | MIXL1 | NANOG | OCT4 | SOX2 | SOX7 | TERT | TUBE |
| Costar 1:30 MATRIGEL | 1.0 | 1.0 | 1.0 | 1.0 | 1.0 | 1.0 | 1.0 | 1.0 | 1.0 | 1.0 |
| Surface Modified Plate 2 | 6.22 | 33.25 | 1.42 | 3.98 | 0.13 | 0.46 | 0.42 | 2.81 | 0.50 | 3.69 |
| Surface Modified Plate 3 | 15.80 | 16.78 | 1.11 | 20.64 | 0.75 | 1.90 | 1.25 | 1.89 | 1.83 | 1.37 |
| Surface Modified Plate 4 | 11.41 | 17.58 | 8.61 | 14.06 | 4.46 | 20.22 | 6.39 | 1.91 | 14.42 | 31.5$$ |

TABLE 3

Expression of Markers Characteristic of the Definitive Endoderm Lineage in Cells of the Human Embryonic Stem Cell Line H1 at Passage 51 (p2) and Passage 53 (p4) Cultured on the Surface Modified Plates of the Present Invention, Treated with Activin A % Expression of the surface marker CXCR4 following differentiation of H1 human ES cells to definitive endoderm

| | p2 | p4 |
|---|---|---|
| Surface #4 | 45.5 | 74.8 |

TABLE 4

Percent confluence (acquisition area occupied by objects) and total human H9 embryonic stem cell colonies greater than 50K sq.microns in the acquisition area after one passage on the Surface Modified Plates of the Present Invention

| NUNC MODIFIED SURFACE | RI EXPOSURE | PERCENT ACQUISITION AREA OCCUPIED BY OBJECTS [%] | ACQUISITION AREA OCCUPIED BY OBJECTS [sq.microns] | TOTAL OBJECTS IN ACQUISITION AREA | PERCENT ACQUISITION AREA OCCUPIED BY hES COLONIES >50K sq.microns [%] |
|---|---|---|---|---|---|
| 2 | 0 | 4.4 | 6.83E+06 | 942 | 3.6 |
| 2 | 1 | 0.4 | 6.89E+05 | 348 | 0.0 |
| 2 | 4 | 9.9 | 1.55E+07 | 2,433 | 8.1 |
| 2 | 10 | 79.4 | 1.24E+08 | 1,146 | 79.2 |
| 3 | 0 | 2.2 | 3.39E+06 | 1,601 | 1.2 |
| 3 | 1 | 4.1 | 6.45E+06 | 1,347 | 3.0 |
| 3 | 4 | 37.5 | 5.85E+07 | 3,230 | 33.9 |
| 3 | 10 | 69.4 | 1.08E+08 | 1,587 | 67.8 |
| 4 | 0 | 15.8 | 2.47E+07 | 1,131 | 26.0 |
| 4 | 1 | 6.9 | 1.07E+07 | 1,507 | 5.7 |
| 4 | 4 | 39.1 | 6.10E+07 | 2,180 | 36.8 |
| 4 | 10 | 92.1 | 1.44E+08 | 449 | 91.8 |
| 13 | 0 | 1.4 | 2.11E+06 | 254 | 0.9 |
| 13 | 1 | 0.2 | 2.97E+05 | 301 | 0.0 |
| 13 | 4 | 10.5 | 1.64E+07 | 6,200 | 5.2 |
| 13 | 10 | 69.4 | 1.08E+08 | 1,587 | 67.8 |

TABLE 4-continued

Percent confluence (acquisition area occupied by objects) and total human H9 embryonic stem cell colonies greater than 50K sq.microns in the acquisition area after one passage on the Surface Modified Plates of the Present Invention

| NUNC MODIFIED SURFACE | ACQUISITION AREA OCCUPIED BY hES COLONIES >50K Sq.microns [sq.microns] | TOTAL hES COLONIES >50K sq.microns IN ACQUISITION AREA | ACQUISITION AERA [sq.micron] | 10X FIELD AREA [sq micron] |
|---|---|---|---|---|
| 2 | 5.61E+06 | 22 | 1.56E+08 | 6.02E+05 |
| 2 | 5.33E+04 | 1 | 1.56E+08 | 6.02E+05 |
| 2 | 1.26E+07 | 47 | 1.56E+08 | 6.02E+05 |
| 2 | 1.24E+08 | 262 | 1.56E+08 | 6.02E+05 |
| 3 | 1.82E+06 | 10 | 1.56E+08 | 6.02E+05 |
| 3 | 4.74E+06 | 21 | 1.56E+08 | 6.02E+05 |
| 3 | 5.29E+07 | 151 | 1.56E+08 | 6.02E+05 |
| 3 | 1.06E+08 | 270 | 1.56E+08 | 6.02E+05 |
| 4 | 4.05E+07 | 96 | 1.56E+08 | 6.02E+05 |
| 4 | 8.96E+06 | 29 | 1.56E+08 | 6.02E+05 |
| 4 | 5.74E+07 | 149 | 1.56E+08 | 6.02E+05 |
| 4 | 1.43E+08 | 264 | 1.56E+08 | 6.02E+05 |
| 13 | 1.45E+06 | 5 | 1.56E+08 | 6.02E+05 |
| 13 | 0.00E+00 | 0 | 1.56E+08 | 6.02E+05 |
| 13 | 8.17E+06 | 30 | 1.56E+08 | 6.02E+05 |
| 13 | 1.06E+08 | 270 | 1.56E+08 | 6.02E+05 |

μM concentration of Y-27632 for 96 hour

RI exposure: culture

TABLE 5

Expression of Markers Characteristic of the Definitive Endoderm Lineage in Cells of the Human Embryonic Stem Cell Line H1 at Passage 51 Cultured on the Surface Modified Plates of the Present Invention, Treated with Activin A
% Expression of the surface marker CXCR4 following differentiation of H1 human ES cells to definitive endoderm

|  | p8 | p10-11 |
|---|---|---|
| Surface #4 (1s) | 62.7 | 55.5 |
| Surface #4 (3s) | 68.4 | 41.4 |
| Surface #3 (5s) | N/A | 55.6 |
| Surface #3 (7s) | 62.5 | 52 |

TABLE 6

Preparation of the Surface Modified Plates of the Present Invention
Preparation of Surface Modified Plates

| Surface | Polymer | Power (W) | Time (s) | P (mbar) | Gas |
|---|---|---|---|---|---|
| Corona Plasma | | | | | |
| 1 | Polystyrene | 2000 | 5 | 1E−02 | Air |
| 13 | Polystyrene | 2000 | 10 | 1E−02 | Air |
| 2 | Polystyrene | 2000 | 15 | 1E−02 | Air |
| 3 | Polystyrene | 2000 | 30 | 1E−02 | Air |
| 4 | Polystyrene | 2000 | 60 | 1E−02 | Air |
| 19 | Cyclic olefin copolymer | 2000 | 60 | 1E−02 | Air |
| 33 | Polycarbonate/polystyrene | 2000 | 60 | 1E−02 | Air |
| 34 | Polycarbonate | 2000 | 60 | 1E−02 | Air |
| Microwave Plasma | | | | | |
| 5 | Polystyrene | 600 | 6 | 0.3-0.4 | Air |
| 6 | Polystyrene | 600 | 12 | 0.3-0.4 | Air |
| 7 | Polystyrene | 600 | 18 | 0.3-0.4 | Air |
| 8 | Polystyrene | 600 | 24 | 0.3-0.4 | Air |
| 9 | Polystyrene | 600 | 6 | 0.3-0.4 | Oxygen |
| 10 | Polystyrene | 600 | 12 | 0.3-0.4 | Oxygen |
| 11 | Polystyrene | 600 | 18 | 0.3-0.4 | Oxygen |
| 12 | Polystyrene | 600 | 24 | 0.3-0.4 | Oxygen |
| 14* | Polystyrene | 500 | 60 | 0.4-0.5 | Air |
| 15 | Polystyrene | 500 | 60 | 0.4-0.5 | Air |

*Not sterilized by gamma irradiation

TABLE 7

Surface Elemental Composition of Surface Modified Plates as Determined by XPS
Surface Elemental Composition of Surface Modified Plates as Determined by XPS
Measurements on two samples and mean ± standard deviation (SD) is given in units of atomic percent

| Surface | % Carbon | | | % Oxygen | | | % Nitrogen | | |
|---|---|---|---|---|---|---|---|---|---|
| | 1 | 2 | Mean ± SD | 1 | 2 | Mean ± SD | 1 | 2 | Mean ± SD |
| Surface 1 | 74.2 | 76.1 | 75.1 ± 0.3 | 24.6 | 22.6 | 23.6 ± 1.4 | 1.3 | 1.3 | 1.3 ± 0.0 |
| Surface 2 | 69.0 | 72.0 | 70.5 ± 2.1 | 29.3 | 26.5 | 27.9 ± 2.0 | 1.8 | 1.6 | 1.7 ± 0.1 |
| Surface 3 | 68.5 | 70.2 | 69.4 ± 1.2 | 29.3 | 28.0 | 28.7 ± 0.9 | 2.2 | 1.8 | 2.0 ± 0.3 |
| Surface 4 | 69.2 | 70.5 | 69.9 ± 0.9 | 28.8 | 27.5 | 28.2 ± 0.9 | 2.1 | 2.0 | 2.1 ± 0.1 |
| Surface 13* | 69.9 | 73.5 | 71.7 ± 2.5 | 27.9 | 24.9 | 26.4 ± 2.1 | 1.9 | 1.6 | 1.8 ± 0.2 |
| Surface 14 | 82.8 | 82.5 | 82.7 ± 0.2 | 15.6 | 15.6 | 15.6 ± 0.0 | 1.6 | 1.8 | 1.7 ± 0.1 |
| Surface 15 | 78.6 | 78.7 | 78.7 ± 0.1 | 20.0 | 20.0 | 20.0 ± 0.0 | 1.4 | 1.3 | 1.4 ± 0.1 |
| Nunclon Delta™ | 84.8 | 84.6 | 84.7 ± 0.1 | 14.7 | 14.7 | 14.7 ± 0.0 | 0.5 | 0.6 | 0.6 ± 0.1 |
| CellBIND™ | 72.3 | 72.2 | 72.2 ± 0.1 | 26.7 | 26.9 | 26.8 ± 0.1 | 1.0 | 0.9 | 1.0 ± 0.1 |
| Falcon™ | 95.2 | 94.7 | 94.9 ± 0.4 | 4.7 | 5.1 | 4.9 ± 0.3 | 0.1 | 0.3 | 0.2 ± 0.1 |
| Costar™ | 85.8 | 85.4 | 85.6 ± 0.3 | 13.8 | 14.4 | 14.1 ± 0.4 | 0.4 | 0.2 | 0.3 ± 0.1 |
| Primaria™ | 77.7 | 76.5 | 77.0 ± 0.8 | 12.7 | 12.9 | 12.8 ± 0.1 | 9.7 | 10.6 | 10.2 ± 0.6 |

*Other elements were detected at a concentration of 0.4%

TABLE 8

Carbon Bonding Environment by C1s Spectra Curve Fitting
Carbon Bonding Environment by C1s Spectra Curve Fitting
Atomic percent of each functional group is given as mean ± standard deviation (n = 2)

| Surface | C—C (284.6 eV) | C*—C—O—C—C* (285.2 eV) | C—O—C, C—$NH_3^+$ (286.1 eV) | C—[O]—C (287.0 eV) | C=O (287.9 eV) | C—O—C*=O (288.9 eV) | $CO_3^-$ (289.8 eV) | O—[C=O]—O (291.0 eV) | Energy loss peak (292 eV) |
|---|---|---|---|---|---|---|---|---|---|
| Surface 1 | 34.5 ± 0.6 | 11.4 ± 0.7 | 14.1 ± 0.7 | 4.2 ± 0.5 | 4.5 ± 0.1 | 1.7 ± 0.1 | 1.7 ± 0.1 | 1.9 ± 0.1 | 0.55 ± 0.1 |
| Surface 2 | 31.7 ± 1.3 | 7.9 ± 1.5 | 13.4 ± 0.8 | 5.4 ± 0.3 | 4.3 ± 0.6 | 2.2 ± 0.1 | 2.7 ± 0.4 | 2.5 ± 0.4 | 0.45 ± 0.1 |
| Surface 3 | 31.5 ± 1.5 | 7.4 ± 2.0 | 12.7 ± 2.1 | 4.8 ± 0.1 | 4.8 ± 0.1 | 2.0 ± 0.1 | 2.8 ± 0.2 | 2.7 ± 0.0 | 0.35 ± 0.2 |
| Surface 4 | 31.6 ± 0.5 | 6.5 ± 2.7 | 14.1 ± 1.3 | 4.1 ± 0.0 | 4.7 ± 0.5 | 3.0 ± 0.5 | 2.6 ± 0.1 | 2.8 ± 0.3 | 0.40 ± 0.3 |
| Surface 13 | 33.6 ± 0.6 | 6.7 ± 3.2 | 13.2 ± 0.5 | 4.9 ± 0.4 | 4.9 ± 0.3 | 2.2 ± 0.2 | 3.0 ± 0.1 | 2.7 ± 0.4 | 0.45 ± 0.2 |
| Surface 14 | 49.7 ± 2.6 | 17.2 ± 3.5 | 8.1 ± 1.7 | 3.2 ± 0.3 | 2.2 ± 0.6 | 1.0 ± 0.1 | 0.8 ± 0.1 | 0.2 ± 0.1 | 0.15 ± 0.1 |
| Surface 15 | 46.7 ± 0.1 | 20.0 ± 0.0 | 11.2 ± 4.0 | 4.0 ± 0.9 | 2.9* | 1.9 ± 0.7 | 1.5 ± 1.0 | 0.3* | 0.10* |
| Nunclon Delta™ | 36.2 ± 1.3 | 28.2 ± 1.3 | 7.9 ± 0.5 | 3.9 ± 0.6 | 3.5 ± 0.1 | 0.8 ± 0.0 | 1.0 ± 0.0 | 1.9 ± 0.1 | 1.1 ± 0.1 |
| CellBIND™ | 27.6 ± 1.1 | 19.2 ± 0.6 | 5.7 ± 0.0 | 6.5 ± 2.0 | 5.7 ± 0.0 | 1.3 ± 1.0 | 3.0 ± 0.1 | 1.6 ± 2.0 | 0.60 ± 0.0 |
| Falcon™ | 76.2 ± 3.2 | 12.0 ± 3.5 | 5.7 ± 1.0 | 0.1 ± 0.2 | 0.0 ± 0.0 | 0.0 ± 0.0 | 0.0 ± 0.1 | 0.6 ± 0.1 | 0.30 ± 0.4 |
| Costar™ | 60.8 ± 6.0 | 12.5 ± 5.4 | 7.0 ± 2.0 | 2.1 ± 0.4 | 0.5 ± 0.3 | 0.2 ± 0.0 | 1.0 ± 0.2 | 0.8 ± 0.0 | 0.60 ± 0.1 |
| Primaria™ | 50.1 ± 1.8 | 11.1 ± 0.2 | 1.9 ± 2.3 | 4.8 ± 0.2 | 3.1 ± 0.1 | 3.0 ± 0.1 | 0.5 ± 0.1 | 0.5 ± 0.0 | 0.30 ± 0.0 |

*The functional group was identified in only one sample.

TABLE 9

Nitrogen Bonding Environment by N1s Spectra Curve Fitting
Nitrogen Bonding Environment by N1s Spectra Curve Fitting
Atomic percent of each functional group is given as mean ± standard deviation (n = 2)

| Surface | —$NH_2$ (398.8 eV) | O=C—N—C=O (400.8 eV) | —$NH_3^+$ (401.8 eV) | —$NO_2$ (406.5 eV) | —$NO_3$ (407.0 eV) |
|---|---|---|---|---|---|
| Surface 1-4 and 13* | 0.0 | 46.9 ± 2.2 | 43.0 ± 0.4 | 10.2 ± 1.8 | 0.0 |
| Surface 14 | 4.0 ± 1.4 | 75.0 ± 1.4 | 21.0 ± 2.8 | 0.0 | 0.0 |
| Surface 15 | 6.0 ± 1.4 | 76.5 ± 3.5 | 14.0 ± 7.1 | 3.0** | 2.0 ± 0.0 |
| Primaria™ | 11.0 ± 0.0 | 81.0 ± 0.0 | 4.0 ± 0.0 | 0.0 | 4.0 ± 0.0 |

*N1s spectra were indistinguishable for Surface modified plates 1-4 and 13, and data resulting from curve fit of two representative N1s spectra is given.
**The functional group was identified in only one sample.

TABLE 10

Surface Roughness of the Surface Modified Plates of the Present Invention as Determined by AFM

| Surface | 10 μm × 10 μm scan | | 500 nm × 500 nm scan | |
|---|---|---|---|---|
| | $R_a$ (nm) | $R_{max}$ (nm) | $R_a$ (nm) | $R_{max}$ (nm) |
| Surface modified plate 1 | 2.40 | 20.97 | 0.13 | 2.35 |
| Surface modified plate 2 | 2.27 | 17.38 | 0.42 | 4.40 |
| Surface modified plate 3 | 2.49 | 22.44 | 0.17 | 2.00 |
| Surface modified plate 4 | 1.77 | 13.83 | 0.32 | 5.20 |
| Surface modified plate 13 | 2.14 | 17.99 | 0.18 | 2.30 |
| Nunclon Delta ™ | 1.75 | 15.22 | 0.17 | 1.67 |
| Cellbind ™ | 1.63 | 13.04 | 0.17 | 2.10 |

TABLE 11

Summary of the Results of the XPS Analysis of Surface Elemental Composition and Human Embryonic Stem Cell Attachment and Colony Formation Experiments on the Surface Modified Plates of the Present Invention

| | | Polymer Material | Surface Treatment | hESC Attachment and Colony Formation (visual inspection) | | | hESC Attachment and Colony Formation (automated microscopy, % confluence) | | % Nitrogen | | % Oxygen | | Sum of % Nitrogen and % Oxygen | Water contact angle (degrees) | |
|---|---|---|---|---|---|---|---|---|---|---|---|---|---|---|---|
| | | | | No RI | Y-27632 | H-1152 | Y-27632 | H-1152 | Mean | SD | Mean | SD | | Mean | SD |
| Surface | 1 | PS | CP | − | ++ | ND | 31.4 | ND | 1.3 | 0.0 | 23.6 | 1.4 | 24.9 | 20.7 | 0.3 |
| | 13 | PS | CP | +* | +++ | +++ | 82.7 | ND | 1.8 | 0.2 | 26.4 | 2.1 | 28.2 | 18.8 | 0.5 |
| | 2 | PS | CP | +* | +++ | +++ | 48.6 | ND | 1.7 | 0.1 | 27.9 | 2.0 | 29.6 | 14.3 | 0.4 |
| | 3 | PS | CP | +* | +++ | +++ | 67.5 | ND | 2.0 | 0.3 | 28.7 | 0.9 | 30.7 | 18.4 | 0.8 |
| | 4 | PS | CP | +* | +++ | +++ | 75.3 | ND | 2.1 | 0.1 | 28.2 | 0.9 | 30.2 | 17.4 | 2.0 |
| | 5 | PS | MP | − | + | ND | 2.9 | ND | 1.3 | 0.2 | 19.6 | 0.2 | 20.9 | 38.7 | 1.1 |
| | 6 | PS | MP | − | + | ND | 6.6 | ND | 1.3 | 0.2 | 19.1 | 0.5 | 20.4 | 39.4 | 1.5 |
| | 7 | PS | MP | − | + | ND | 4.3 | ND | 1.3 | 0.1 | 20.1 | 1.9 | 21.4 | 38.1 | 1.3 |
| | 8 | PS | MP | − | + | ND | 5.7 | ND | 1.5 | 0.1 | 20.0 | 1.0 | 21.5 | 39.0 | 1.5 |
| | 9 | PS | MP | − | + | ND | 18.3 | ND | 1.0 | 0.1 | 19.3 | 0.8 | 20.3 | 42.0 | 0.8 |
| | 10 | PS | MP | − | + | ND | 11.5 | ND | 0.8 | 0.2 | 19.1 | 0.2 | 19.9 | 41.0 | 1.1 |
| | 11 | PS | MP | − | + | ND | 10.7 | ND | 0.9 | 0.1 | 20.3 | 0.1 | 21.2 | 40.0 | 0.7 |
| | 12 | PS | MP | − | + | ND | 19.3 | ND | 0.9 | 0.1 | 21.2 | 0.7 | 22.1 | 40.0 | 0.6 |
| | 14 | PS | MP | − | + | ND | ND | ND | 1.7 | 0.1 | 15.6 | 0.0 | 17.3 | ND | |
| | 15 | PS | MP | − | + | ND | ND | ND | 1.4 | 0.1 | 20.0 | 0.0 | 21.4 | ND | |
| | 18 | COC | None | − | − | − | ND | ND | 0.0 | 0.0 | 2.3 | 0.1 | 2.3 | ND | |
| | 19 | COC | CP | − | ++ | ++ | ND | ND | 1.3 | 0.1 | 25.4 | 1.0 | 26.7 | ND | |
| | 22 | PS | | − | ND | − | ND | ND | 1.6 | **** | 15.9 | **** | 17.5 | 21.4 | 0.7 |
| | 23 | PS | | − | ND | − | ND | ND | 1.1 | 0.1 | 17.1 | 1.2 | 18.2 | 30.0 | 2.1 |
| | 24 | PS | | − | ND | − | ND | ND | 1.3 | 0.4 | 16.7 | 2.7 | 18.0 | 27.7 | 3.3 |
| | 29 | PS | | − | ND | − | ND | ND | 17.9 | 2.1 | 28.7 | 0.8 | 46.6 | 7.9 | 0.6 |
| | 30 | PS/PC | None | − | ND | − | ND | ND | 0.2 | 0.1 | 3.9 | 0.6 | 4.1 | 70.2 | 0.5 |
| | 33 | PS/PC | CP | − | ND | ++ | ND | ND | 1.0 | 0.1 | 25.0 | 0.2 | 26.0 | 21.8 | 0.5 |
| | 31 | PC | None | − | ND | − | ND | ND | 0.0 | 0.0 | 16.7 | 0.4 | 16.7 | ND | |
| | 32 | PC | None | − | ND | − | ND | ND | 0.0 | 0.0 | 17.0 | 0.4 | 17.0 | ND | |
| | 34 | PC | CP | − | ND | ++ | ND | ND | 1.1 | 0.1 | 23.9 | 0.6 | 25.0 | ND | |
| CellBIND ™ | | PS | | +** | ++ | ++ | ND | ND | 1.0 | 0.1 | 26.8 | 0.1 | 27.8 | 44.3 | 1.3 |
| Nunclon Delta ™ | | PS | | − | − | − | ND | ND | 0.6 | 0.1 | 14.7 | 0.0 | 15.3 | 63.1 | 2.0 |
| Falcon ™ | | PS | | − | − | − | ND | ND | 0.2 | 0.1 | 4.9 | 0.3 | 5.1 | 75.1 | 2.9 |

TABLE 11-continued

Summary of the Results of the XPS Analysis of Surface Elemental Composition and Human Embryonic Stem Cell Attachment and Colony Formation Experiments on the Surface Modified Plates of the Present Invention

| | Polymer Material | Surface Treatment | hESC Attachment and Colony Formation (visual inspection) | | | hESC Attachment and Colony Formation (automated microscopy, % confluence) | | % Nitrogen | | % Oxygen | | Sum of % Nitrogen and % Oxygen | Water contact angle (degrees) | |
|---|---|---|---|---|---|---|---|---|---|---|---|---|---|---|
| | | | No RI | Y-27632 | H-1152 | Y-27632 | H-1152 | Mean | SD | Mean | SD | | Mean | SD |
| Costar ™ | PS | | − | − | − | ND | ND | 0.3 | 0.1 | 14.1 | 0.4 | 14.4 | 61.4 | 2.4 |
| Primaria ™ | PS | | +*** | +++ | +++ | ND | ND | 10.2 | 0.6 | 12.8 | 0.1 | 23.0 | 39.5 | 2.0 |

"−" means formation of less than 15 colonies per 10 cm$^2$
"+", "++", and "+++" means some (15 or more colonies per 10 cm$^2$), more, and most human ES cell attachment and colony formation, respectively
"RI" means Rho kinase inhibitor;
"ND" means experiment not done
"PS" means polystyrene;
"PC" means polycarbonate;
"PS/PC" means blend of polystyrene and polycarbonate;
"COC" means cyclic olefin copolymer;
"CP" means corona plasma;
"MP" means microwave plasma
*Human ES cells attach and grow into colonies that can be passaged about 3 times (then growth rate declines spontaneously)
**Human ES cells attach and grow into colonies that spontaneously differentiate before the first passaging
***Human ES cells attach and grow into colonies (passaging not tested)
**** Only one sample available for analysis

TABLE 12

Surface Elemental Composition as Determined by XPS
Surface Elemental Composition as Determined by XPS
Measurements on two samples (except Surface 22) and mean ± standard deviation (SD) is given in units of atomic percent

| | % Carbon | | | % Oxygen | | | % Nitrogen | | |
|---|---|---|---|---|---|---|---|---|---|
| Surface | 1 | 2 | Mean ± SD | 1 | 2 | Mean ± SD | 1 | 2 | Mean ± SD |
| Surface 5 | 79.1 | 79.1 | 79.1 ± 0.0 | 19.5 | 19.8 | 19.6 ± 0.2 | 1.4 | 1.1 | 1.3 ± 0.2 |
| Surface 6 | 79.4 | 79.2 | 79.3 ± 0.1 | 19.5 | 18.8 | 19.1 ± 0.5 | 1.1 | 1.4 | 1.3 ± 0.2 |
| Surface 7 | 76.2 | 80.0 | 78.1 ± 2.7 | 21.5 | 18.8 | 20.1 ± 1.9 | 1.3 | 1.2 | 1.3 ± 0.1 |
| Surface 8 | 77.8 | 78.7 | 78.2 ± 0.6 | 20.8 | 19.3 | 20.0 ± 1.0 | 1.4 | 1.5 | 1.5 ± 0.1 |
| Surface 9 | 79.2 | 80.3 | 79.7 ± 0.8 | 19.9 | 18.7 | 19.3 ± 0.8 | 0.9 | 1.0 | 1.0 ± 0.1 |
| Surface 10 | 80.4 | 79.2 | 79.8 ± 0.8 | 19.0 | 19.3 | 19.1 ± 0.2 | 0.6 | 0.9 | 0.8 ± 0.2 |
| Surface 11 | 78.7 | 78.6 | 78.6 ± 0.1 | 20.4 | 20.3 | 20.3 ± 0.1 | 0.9 | 0.8 | 0.9 ± 0.1 |
| Surface 12 | 77.2 | 78.5 | 77.8 ± 0.9 | 21.8 | 20.7 | 21.2 ± 0.7 | 1.0 | 0.8 | 0.9 ± 0.1 |
| Surface 18* | 97.6 | 97.8 | 97.7 ± 0.1 | 2.4 | 2.2 | 2.3 ± 0.1 | 0.0 | 0.0 | 0.0 ± 0.0 |
| Surface 19 | 74.1 | 72.5 | 73.3 ± 1.1 | 24.7 | 26.2 | 25.4 ± 1.0 | 1.2 | 1.3 | 1.3 ± 0.1 |
| Surface 22 | 82.5 | | | 15.9 | | | 1.6 | | |
| Surface 23** | 82.2 | 79.1 | 80.7 ± 2.2 | 16.2 | 17.9 | 17.1 ± 1.2 | 1.0 | 1.1 | 1.1 ± 0.1 |
| Surface 24** | 84.0 | 79.6 | 81.8 ± 3.1 | 14.8 | 18.6 | 16.7 ± 2.7 | 1.0 | 1.6 | 1.3 ± 0.4 |
| Surface 29 | 52.5 | 54.5 | 53.5 ± 1.4 | 28.1 | 29.2 | 28.7 ± 0.8 | 19.4 | 16.4 | 17.9 ± 2.1 |
| Surface 30* | 96.3 | 95.5 | 95.9 ± 0.6 | 3.5 | 4.4 | 3.9 ± 0.6 | 0.2 | 0.1 | 0.2 ± 0.1 |
| Surface 31*,** | 83.0 | 81.3 | 82.2 ± 1.2 | 16.4 | 17.0 | 16.7 ± 0.4 | 0.0 | 0.0 | 0.0 ± 0.0 |
| Surface 32* | 83.3 | 82.7 | 83.0 ± 0.4 | 16.7 | 17.3 | 17.0 ± 0.4 | 0.0 | 0.0 | 0.0 ± 0.0 |
| Surface 33 | 74.2 | 73.7 | 73.9 ± 0.3 | 24.9 | 25.2 | 25.0 ± 0.2 | 0.9 | 1.0 | 1.0 ± 0.1 |
| Surface 34 | 74.7 | 75.5 | 75.1 ± 0.6 | 24.3 | 23.5 | 23.9 ± 0.6 | 1.1 | 1.0 | 1.1 ± 0.1 |

*Not plasma treated.
**Other elements were detected at a concentration of 0.2-2.0%.

TABLE 13

Carbon Bonding Environment by C1s Spectra Curve Fitting
Carbon Bonding Environment by C1s Spectra Curve Fitting
Atomic percent of each functional group is given based on one measurement on Surfaces 5-
12 and 22, and as mean ± standard deviation for the other surfaces (n = 2)

Functional groups and C1s binding energies (eV)

| Surface | C—C (284.6 eV) | C*—C—O—C—C* (285.2 eV) | C—O—C, C—NH$_3^+$ (286.1 eV) | C—[O]—C (287.0 eV) | C=O (287.9 eV) | C—O—C*=O (288.9 eV) | CO$_3^-$ (289.8 eV) | O—[C=O]—O (291.0 eV) | Energy loss peak (292 eV) |
|---|---|---|---|---|---|---|---|---|---|
| Surface 5 | 38.0 | 22.1 | 8.2 | 4.6 | 0.6 | 1.4 | 2.8 | 0.8 | 0.0 |
| Surface 6 | 34.3 | 26.0 | 10.6 | 5.2 | 1.1 | 1.3 | 1.0 | 0.1 | 0.0 |
| Surface 7 | 31.2 | 23.7 | 9.6 | 5.7 | 0.8 | 1.4 | 2.7 | 0.5 | 0.5 |
| Surface 8 | 31.7 | 25.2 | 9.6 | 5.0 | 0.7 | 1.6 | 2.8 | 0.7 | 0.5 |
| Surface 9 | 37.3 | 22.6 | 8.4 | 4.5 | 0.6 | 1.2 | 3.2 | 0.8 | 0.6 |
| Surface 10 | 51.5 | 9.6 | 11.3 | 4.0 | 0.0 | 0.8 | 1.6 | 0.0 | 1.6 |
| Surface 11 | 34.7 | 23.0 | 8.5 | 4.7 | 2.3 | 0.4 | 1.1 | 0.6 | 0.6 |
| Surface 12 | 36.3 | 21.0 | 8.1 | 4.8 | 1.2 | 1.2 | 3.4 | 0.7 | 0.5 |
| Surface 18* | 86.4 ± 1.9 | 0.0 | 9.8 ± 1.4 | 0.0 | 0.0 | 1.5 ± 0.7 | 0.0 | 0.0 | 0.0 |
| Surface 19 | 31.5 ± 1.5 | 18.7 ± 0.3 | 11 ± 0.8 | 10.3 ± 0.1 | 0.0 | 1.8 ± 0.5 | 0.0 | 0.0 | 0.0 |
| Surface 22 | 61.5 | 10.4 | 4.9 | 0.0 | 1.2 | 0.9 | 2.3 | 1.5 | 0.0 |
| Surface 23 | 62.5 ± 4.1 | 9.0 ± 0.7 | 4.2 ± 0.3 | 0.0 | 1.5 ± 0.6 | 0.8 ± 0.1 | 1.9 ± 0.0 | 0.9 ± 0.5 | 0.0 |
| Surface 24 | 66.2 ± 6.1 | 8.8 ± 0.4 | 2.4 ± 0.9 | 0.0 | 1.0 ± 0.6 | 1.2 ± 0.6 | 1.3 ± 0.6 | 1.1 ± 0.1 | 0.0 |
| Surface 29 | 17.8 ± 4.9 | 0.0 | 18.9 ± 1.3 | 5.4 ± 0.9 | 7.4 ± 5.0 | 4.2 ± 0.6 | 0.0 | 0.0 | 0.0 |
| Surface 30* | 84.3 ± 0.5 | 0.0 | 5.7 ± 0.1 | 1.9 ± 0.0 | 0.0 | 0.0 | 0.0 | 0.0 | 3.9 ± 0.1 |
| Surface 31* | 55.3 ± 0.6 | 9.3 ± 0.3 | 9.0 ± 0.1 | 3.5 ± 0.2 | 0.0 | 0.0 | 0.0 | 0.0 | 2.4 ± 0.1 |
| Surface 32* | 51.5 ± 8.5 | 11.2 ± 2.8 | 10.7 ± 3.5 | 3.3 ± 1.1 | 0.0 | 0.0 | 0.0 | 3.3 ± 0.0 | 2.9 ± 0.6 |
| Surface 33 | 27.7 ± 1.7 | 19.9 ± 0.9 | 11.1 ± 0.0 | 11.1 ± 0.0 | 0.0 | 4.1 ± 0.4 | 0.0 | 0.0 | 0.0 |
| Surface 34 | 29.2 ± 0.2 | 21.0 ± 0.1 | 10.9 ± 0.6 | 10.1 ± 0.5 | 0.0 | 3.7 ± 0.1 | 0.0 | 0.0 | 0.0 |

*Not plasma treated.

TABLE 14

Nitrogen Bonding Environment by N1s Spectra Curve Fitting
Nitrogen Bonding Environment by N1s Spectra Curve Fitting
Atomic percent of each functional group is given based on one measurement
on Surfaces 5-12 and 22, and as mean ± standard deviation
for the other surfaces (n = 2)

Functional groups and N1s binding energies in eV

| Surface | —NH$_2$ (398.8 eV) | O=C—N—C=O (400.8 eV) | —NH$_3^+$ (401.8 eV) | —NO$_2$ (406.5 eV) | —NO$_3$ (407.0 eV) |
|---|---|---|---|---|---|
| Surface 5 | 3.0 | 50.0 | 36.0 | 2.0 | 9.0 |
| Surface 6 | 46.0 | 26.0 | 11.0 | 5.0 | 12.0 |
| Surface 7 | 25.0 | 47.0 | 22.0 | 2.0 | 4.0 |
| Surface 8 | 13.0 | 56.0 | 26.0 | 1.0 | 4.0 |
| Surface 9 | 2.0 | 44.0 | 45.0 | 4.0 | 5.0 |
| Surface 10 | 8.0 | 71.0 | 17.0 | 2.0 | 2.0 |
| Surface 11 | 13.0 | 37.0 | 35.0 | 4.0 | 11.0 |
| Surface 12 | 6.0 | 52.0 | 31.0 | 2.0 | 9.0 |
| Surface 18* | ND** | ND | ND | ND | ND |
| Surface 19 | 19.0 ± 8.4 | 51.5 ± 6.3 | 24.0 ± 2.8 | 1.5 ± 0.7 | 4.0 ± 0.0 |
| Surface 22 | 22.0 | 24.0 | 54.0 | 0.0 | 0.0 |
| Surface 23 | 26.0 ± 1.4 | 51.0 ± 4.2 | 23.0 ± 5.7 | 0.0 | 0.0 |
| Surface 24 | 23.0 ± 17.0 | 47.0 ± 5.7 | 30.0 ± 11.3 | 0.0 | 0.0 |
| Surface 29 | 52.0 ± 9.9 | 35.0 ± 15.6 | 6.0 ± 2.8 | 3.5 ± 2.1 | 3.0 ± 1.4 |
| Surface 30* | ND | ND | ND | ND | ND |
| Surface 31* | ND | ND | ND | ND | ND |
| Surface 32* | ND | ND | ND | ND | ND |
| Surface 33 | 7.5 ± 0.7 | 53.5 ± 2.1 | 29.5 ± 0.7 | 5.0 ± 0.0 | 4.5 ± 2.1 |
| Surface 34 | 11.5 ± 2.1 | 55.5 ± 6.4 | 28.0 ± 7.1 | 4.0 ± 1.4 | 1.0 ± 0.0 |

*Not plasma treated.
**ND: analyzed, but not detected.

What is claimed is:

1. A method to enhance the attachment of human pluripotent stem cells to a surface lacking a feeder cell layer and lacking an adlayer, comprising the steps of:
   a. obtaining a suspension of human pluripotent stem cells;
   b. treating the suspension of cells of step (a) with at least one compound selected from the group consisting of: a compound capable of inhibiting Rho kinase activity, and a compound capable of inhibiting Rho activity;
   c. adding the suspension of cells of step (b) to a surface having a static sessile contact angle of at least about 14.3 degrees, and wherein the surface comprises polystyrene and contains from 1.6% N to 1.8% N, a sum of O and N of greater than or equal to 29.6%;

d. allowing the cells of step (c) to attach to the surface; wherein attachment is enhanced compared to cells not treated with the at least one compound, and wherein the pluripotency of the attached cells is maintained; and
e. culturing the attached cells without differentiating the cells.

2. The method of claim 1, wherein the cells are maintained in culture after the cells attach to the surface.

3. The method of claim 2, wherein the at least one compound is removed after the cells attach to the surface.

4. The method of claim 1, wherein the cells are detached from the surface by removing the at least one compound.

5. The method of claim 1, wherein the suspension of cells is a suspension of clusters of cells.

6. The method of claim 1, wherein the suspension of cells is a suspension of single cells.

7. The method of claim 1, wherein the surface is part of a vessel or matrix.

8. A method to enhance the attachment of human pluripotent stem cells to a surface lacking a feeder cell layer and lacking an adlayer, and comprising the steps of:
   a. obtaining a suspension of human pluripotent stem cells;
   b. treating the suspension of cells of step (a) with at least one compound selected from the group consisting of: a compound capable of inhibiting Rho kinase activity, and a compound capable of inhibiting Rho activity;
   c. adding the suspension of cells of step (b) to a surface having a static sessile contact angle of at least about 14.3 degrees, and wherein the surface comprises polystyrene and contains from 1.6% N to 1.8% N, a sum of O and N of greater than or equal to 29.6%;
   d. allowing the cells of step (c) to attach to the surface; and wherein attachment is enhanced compared to cells not treated with the at least one compound;
   e. maintaining the cells of step (d) in culture after the cells attach to the surface without differentiating the cells, and wherein the pluripotency of the attached cells is maintained; and
   f. removing the at least one compound from the culture after the cells attach to the surface without differentiating the cells and cells remain attached.

9. The method of claim 1, wherein the method comprises treating the suspension of cells with a compound capable of inhibiting Rho kinase activity.

10. The method of claim 1, wherein the method comprises treating the suspension of cells with a compound capable of inhibiting Rho activity.

11. The method of claim 8, wherein the suspension of cells is a suspension of clusters of cells.

12. The method of claim 8, wherein the suspension of cells is a suspension of single cells.

13. The method of claim 8, wherein the surface is part of a vessel or matrix.

14. The method of claim 8, wherein the method comprises treating the suspension of cells with a compound capable of inhibiting Rho kinase activity.

15. The method of claim 8, wherein the method comprises treating the suspension of cells with a compound capable of inhibiting Rho activity.

16. A method to enhance the attachment of human pluripotent stem cells to a surface lacking a feeder cell layer and comprising:
   a. adding a suspension of human pluripotent cells treated with a compound capable of inhibiting Rho kinase activity or compound capable of inhibiting Rho activity to a surface having a static sessile contact angle of at least about 14.3 degrees, wherein the surface comprises polystyrene and contains from 1.6% N to 1.8% N, a sum of O and N of greater than or equal to 29.6%, and wherein attachment is enhanced compared to cells not treated with the at least one compound; and allowing the cells to attach; and
   b. culturing the attached cells of step (a) without differentiating the cells.

17. The method of claim 1, wherein the surface is corona plasma treated.

18. The method of claim 8, wherein the surface is corona plasma treated.

19. The method of claim 16, wherein the surface is corona plasma treated.

20. The method of claim 1, wherein the surface has a static sessile contact angle from about 14.3 degrees to about 18.8 degrees.

21. The method of claim 8, wherein the surface has a static sessile contact angle from about 14.3 degrees to about 18.8 degrees.

22. The method of claim 16, wherein the surface has a static sessile contact angle from about 14.3 degrees to about 18.8 degrees.

* * * * *